US010265404B2

(12) United States Patent
Tamarkin et al.

(10) Patent No.: US 10,265,404 B2
(45) Date of Patent: *Apr. 23, 2019

(54) COMPOSITIONS, GELS AND FOAMS WITH RHEOLOGY MODULATORS AND USES THEREOF

(71) Applicant: Foamix Pharmaceuticals Ltd., Rehovot (IL)

(72) Inventors: Dov Tamarkin, Maccabim (IL); Elana Gazal, Rehovot (IL); Yohan Hazot, Rehovot (IL); David Schuz, Gimzu (IL); Irakliy Papiashvili, Ashkelon (IL)

(73) Assignee: Foamix Pharmaceuticals Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/078,746

(22) Filed: Nov. 13, 2013

(65) Prior Publication Data

US 2014/0066524 A1 Mar. 6, 2014

Related U.S. Application Data

(63) Continuation of application No. 13/100,724, filed on May 4, 2011, now Pat. No. 8,618,081, which is a continuation-in-part of application No. PCT/IB2010/002612, filed on Oct. 1, 2010, and application No. 13/100,724, May 4, 2011, which is a continuation-in-part of application No. PCT/IB2010/002617, filed on Oct. 1, 2010, and application No. 13/100,724, May 4, 2011, which is a
(Continued)

(51) Int. Cl.
| | |
|---|---|
| A61K 31/65 | (2006.01) |
| A61K 47/44 | (2017.01) |
| A61K 9/12 | (2006.01) |
| A61P 31/04 | (2006.01) |
| A61P 17/00 | (2006.01) |
| A61P 17/06 | (2006.01) |
| A61P 17/10 | (2006.01) |
| A61K 47/06 | (2006.01) |
| A61K 9/00 | (2006.01) |
| A61K 31/4164 | (2006.01) |
| A61K 31/57 | (2006.01) |
| A61K 31/573 | (2006.01) |
| A61K 31/593 | (2006.01) |
| A61K 8/34 | (2006.01) |
| A61K 8/36 | (2006.01) |
| A61K 47/10 | (2017.01) |
| A61K 47/12 | (2006.01) |
| A61K 31/137 | (2006.01) |
| A61K 31/192 | (2006.01) |
| A61K 45/06 | (2006.01) |
| A61K 47/02 | (2006.01) |
| A61K 47/24 | (2006.01) |
| A61K 8/31 | (2006.01) |
| A61Q 17/04 | (2006.01) |
| A61Q 19/00 | (2006.01) |
| A61Q 19/10 | (2006.01) |

(52) U.S. Cl.
CPC ........... *A61K 47/44* (2013.01); *A61K 8/31* (2013.01); *A61K 8/342* (2013.01); *A61K 8/361* (2013.01); *A61K 9/0014* (2013.01); *A61K 9/0048* (2013.01); *A61K 9/12* (2013.01); *A61K 9/122* (2013.01); *A61K 9/124* (2013.01); *A61K 31/137* (2013.01); *A61K 31/192* (2013.01); *A61K 31/4164* (2013.01); *A61K 31/57* (2013.01); *A61K 31/573* (2013.01); *A61K 31/593* (2013.01); *A61K 31/65* (2013.01); *A61K 45/06* (2013.01); *A61K 47/02* (2013.01); *A61K 47/06* (2013.01); *A61K 47/10* (2013.01); *A61K 47/12* (2013.01); *A61K 47/24* (2013.01); *A61Q 17/04* (2013.01); *A61Q 19/00* (2013.01); *A61Q 19/10* (2013.01); *A61K 2800/31* (2013.01); *A61K 2800/33* (2013.01)

(58) Field of Classification Search
CPC .......... A61K 47/44; A61K 8/31; A61K 8/342; A61K 8/361; A61K 9/0014; A61K 9/0048; A61K 9/12; A61K 9/122; A61K 9/124; A61K 31/137; A61K 31/192; A61K 31/4164; A61K 31/57; A61K 31/573; A61K 31/593; A61K 31/65; A61K 47/02; A61K 47/06; A61K 47/10; A61K 47/12; A61K 47/24
USPC ......... 514/152; 424/400, 401, 502, 731, 727
See application file for complete search history.

(56) References Cited

U.S. PATENT DOCUMENTS

| | | |
|---|---|---|
| 1,159,250 A | 11/1915 | Moulton |
| 1,666,684 A | 4/1928 | Carstens |

(Continued)

FOREIGN PATENT DOCUMENTS

| | | |
|---|---|---|
| AU | 198780257 | 9/1986 |
| AU | 782515 | 12/2005 |

(Continued)

OTHER PUBLICATIONS

U.S. Appl. No. 60/789,186, filed Apr. 4, 2006, Tamarkin.
U.S. Appl. No. 60/815,948, filed Jun. 23, 2006, Tamarkin.
U.S. Appl. No. 60/818,634, filed Jul. 5, 2006, Friedman.
U.S. Appl. No. 60/843,140, filed Sep. 8, 2006, Tamarkin.
U.S. Appl. No. 61/248,144, filed Oct. 2, 2009, Tamarkin.
(Continued)

*Primary Examiner* — Irina Neagu
(74) *Attorney, Agent, or Firm* — Finnegan, Henderson, Farabow, Garrett & Dunner, L.L.P.

(57) ABSTRACT

The present disclosure relates generally to compositions for cosmetic or pharmaceutical application. The compositions include a carrier and rheology modulators.

18 Claims, 2 Drawing Sheets

Related U.S. Application Data continuation-in-part of application No. PCT/IB2010/002613, filed on Oct. 1, 2010.

(60) Provisional application No. 61/248,144, filed on Oct. 2, 2009, provisional application No. 61/322,148, filed on Apr. 8, 2010, provisional application No. 61/349,911, filed on May 31, 2010, provisional application No. 61/385,385, filed on Sep. 22, 2010, provisional application No. 61/331,126, filed on May 4, 2010, provisional application No. 61/388,884, filed on Oct. 1, 2010, provisional application No. 61/380,568, filed on Sep. 7, 2010.

(56) References Cited

U.S. PATENT DOCUMENTS

| | | | |
|---|---|---|---|
| 1,924,972 | A | 8/1933 | Beckert |
| 2,085,733 | A | 7/1937 | Bird |
| 2,390,921 | A | 12/1945 | Clark |
| 2,524,590 | A | 10/1950 | Boe |
| 2,586,287 | A | 2/1952 | Apperson |
| 2,617,754 | A | 11/1952 | Neely |
| 2,767,712 | A | 10/1956 | Waterman |
| 2,968,628 | A | 1/1961 | Reed |
| 3,004,894 | A | 10/1961 | Johnson et al. |
| 3,062,715 | A | 11/1962 | Reese et al. |
| 3,067,784 | A | 12/1962 | Gorman |
| 3,092,255 | A | 6/1963 | Hohman |
| 3,092,555 | A | 6/1963 | Horn |
| 3,141,821 | A | 7/1964 | Compeau |
| 3,142,420 | A | 7/1964 | Gawthrop |
| 3,144,386 | A | 8/1964 | Brightenback |
| 3,149,543 | A | 9/1964 | Naab |
| 3,154,075 | A | 10/1964 | Weckesser |
| 3,178,352 | A | 4/1965 | Erickson |
| 3,236,457 | A | 2/1966 | Kennedy et al. |
| 3,244,589 | A | 4/1966 | Sunnen |
| 3,252,859 | A | 5/1966 | Silver |
| 3,261,695 | A | 7/1966 | Sienkiewicz |
| 3,263,867 | A | 8/1966 | Lehmann |
| 3,263,869 | A | 8/1966 | Corsette |
| 3,298,919 | A | 1/1967 | Bishop et al. |
| 3,301,444 | A | 1/1967 | Wittke |
| 3,303,970 | A | 2/1967 | Breslau et al. |
| 3,330,730 | A | 7/1967 | Hernandez |
| 3,333,333 | A | 8/1967 | Noack |
| 3,334,147 | A | 8/1967 | Brunelle et al. |
| 3,342,845 | A | 9/1967 | Sayigh et al. |
| 3,346,451 | A | 10/1967 | Collins et al. |
| 3,366,494 | A | 1/1968 | Bower et al. |
| 3,369,034 | A | 2/1968 | Chalmers |
| 3,377,004 | A | 4/1968 | Wittke |
| 3,383,280 | A | 5/1968 | Kuehns |
| 3,384,541 | A | 5/1968 | Clark et al. |
| 3,395,214 | A | 7/1968 | Mummert |
| 3,395,215 | A | 7/1968 | Schubert |
| 3,401,849 | A | 9/1968 | Weber, III |
| 3,419,658 | A | 12/1968 | Sanders |
| 3,456,052 | A | 7/1969 | Gordon |
| 3,527,559 | A | 9/1970 | Sliwinski |
| 3,540,448 | A | 11/1970 | Sunnen |
| 3,559,890 | A | 2/1971 | Brooks et al. |
| 3,561,262 | A | 2/1971 | Borucki |
| 3,563,098 | A | 2/1971 | Weber, III |
| 3,574,821 | A | 4/1971 | Pfirrmann |
| 3,577,518 | A | 5/1971 | Shepherd |
| 3,667,461 | A | 6/1972 | Zamarra |
| 3,751,562 | A | 8/1973 | Nichols |
| 3,770,648 | A | 11/1973 | Mackles |
| 3,787,566 | A | 1/1974 | Gauvreau |
| 3,819,524 | A | 6/1974 | Schubert et al. |
| 3,824,303 | A | 7/1974 | Lanzet et al. |
| 3,841,525 | A | 10/1974 | Siegel |
| 3,849,569 | A * | 11/1974 | Mead ............ 514/199 |
| 3,849,580 | A | 11/1974 | Weinstein et al. |
| 3,865,275 | A | 2/1975 | De Nunzio |
| 3,866,800 | A | 2/1975 | Schmitt |
| 3,878,118 | A | 4/1975 | Watson |
| 3,882,228 | A | 5/1975 | Boncey et al. |
| 3,886,084 | A | 5/1975 | Vassiliades |
| 3,890,305 | A | 6/1975 | Weber et al. |
| 3,912,665 | A | 10/1975 | Spitzer et al. |
| 3,912,667 | A | 10/1975 | Spitzer et al. |
| 3,923,970 | A | 12/1975 | Breuer |
| 3,929,985 | A | 12/1975 | Webb, Jr. |
| 3,952,916 | A | 4/1976 | Phillips |
| 3,953,591 | A | 4/1976 | Snyder |
| 3,959,160 | A | 5/1976 | Horsler et al. |
| 3,962,150 | A | 6/1976 | Viola |
| 3,963,833 | A | 6/1976 | DeSalva et al. |
| 3,966,090 | A | 6/1976 | Prussin et al. |
| 3,966,632 | A | 6/1976 | Colliopoulos et al. |
| 3,970,219 | A | 7/1976 | Spitzer et al. |
| 3,970,584 | A | 7/1976 | Hart et al. |
| 3,993,224 | A | 11/1976 | Harrison |
| 3,997,467 | A | 12/1976 | Jederstrom |
| 4,001,391 | A | 1/1977 | Feinstone et al. |
| 4,001,442 | A | 1/1977 | Stahlberger et al. |
| 4,018,396 | A | 4/1977 | Showmaker et al. |
| 4,019,657 | A | 4/1977 | Spitzer et al. |
| 4,052,513 | A | 10/1977 | Kaplan |
| 4,083,974 | A | 4/1978 | Turi |
| 4,102,995 | A | 7/1978 | Hebborn |
| 4,100,426 | A | 8/1978 | Barnhurst et al. |
| 4,110,426 | A | 8/1978 | Barnhurst et al. |
| 4,124,149 | A | 11/1978 | Spitzer et al. |
| 4,145,411 | A | 3/1979 | Mende |
| 4,151,272 | A | 4/1979 | Geary et al. |
| 4,160,827 | A | 7/1979 | Cho et al. |
| 4,178,373 | A | 12/1979 | Klein et al. |
| 4,213,979 | A | 7/1980 | Levine |
| 4,214,000 | A | 7/1980 | Papa |
| 4,226,344 | A | 10/1980 | Booth et al. |
| 4,229,432 | A | 10/1980 | Geria |
| 4,230,701 | A | 10/1980 | Holick et al. |
| 4,241,048 | A | 12/1980 | Durbak et al. |
| 4,241,149 | A | 12/1980 | Labes et al. |
| 4,252,787 | A | 2/1981 | Sherman et al. |
| 4,254,104 | A | 3/1981 | Suzuki et al. |
| 4,268,499 | A | 5/1981 | Keil |
| 4,271,149 | A | 6/1981 | Winicov et al. |
| 4,292,250 | A | 9/1981 | DeLuca et al. |
| 4,292,326 | A | 9/1981 | Nazzaro-Porro et al. |
| 4,299,826 | A | 11/1981 | Luedders |
| 4,305,936 | A | 12/1981 | Klein |
| 4,309,995 | A | 1/1982 | Sacco |
| 4,310,510 | A | 1/1982 | Sherman et al. |
| 4,323,582 | A | 4/1982 | Siegel et al. |
| 4,323,694 | A | 4/1982 | Scala, Jr. |
| 4,325,939 | A | 4/1982 | Shah |
| 4,329,990 | A | 5/1982 | Sneider |
| 4,335,120 | A | 6/1982 | Holick et al. |
| 4,338,211 | A | 7/1982 | Stiros |
| 4,352,808 | A | 10/1982 | Rane et al. |
| 4,363,806 | A | 12/1982 | Bergström et al. |
| 4,385,161 | A | 5/1983 | Caunt et al. |
| 4,386,104 | A | 5/1983 | Nazzaro-Porro |
| 4,393,066 | A | 7/1983 | Garrett et al. |
| 4,427,670 | A | 1/1984 | Ofuchi et al. |
| 4,439,416 | A | 3/1984 | Cordon et al. |
| 4,439,441 | A | 3/1984 | Hallesy et al. |
| 4,440,320 | A | 4/1984 | Wernicke |
| 4,447,486 | A | 5/1984 | Hoppe et al. |
| 4,469,674 | A | 9/1984 | Shah et al. |
| 4,508,705 | A | 4/1985 | Chaudhuri et al. |
| 4,522,948 | A | 6/1985 | Walker |
| 4,529,601 | A | 7/1985 | Broberg et al. |
| 4,529,605 | A | 7/1985 | Lynch et al. |
| 4,552,872 | A | 11/1985 | Cooper et al. |
| 4,574,052 | A | 3/1986 | Gupte et al. |
| 4,576,961 | A | 3/1986 | Lorck et al. |
| 4,595,526 | A | 6/1986 | Lai |
| 4,603,812 | A | 8/1986 | Stoesser et al. |

(56) References Cited

U.S. PATENT DOCUMENTS

| | | |
|---|---|---|
| 4,607,101 A | 8/1986 | Bernstein |
| 4,612,193 A | 9/1986 | Gordon et al. |
| 4,627,973 A | 12/1986 | Moran et al. |
| 4,628,063 A | 12/1986 | Haines et al. |
| 4,661,340 A | 4/1987 | Nagy née Kricsfalussy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,849,211 A | 7/1989 | Schrauzer |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,877,805 A | 10/1989 | Kligman |
| 4,876,083 A | 11/1989 | Knudson et al. |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,530 A | 6/1993 | Janchitraponvej et al. |
| 5,221,534 A | 6/1993 | DesLauriers et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,305 A | 2/1995 | Repinec et al. |
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |

(56) References Cited

U.S. PATENT DOCUMENTS

| | | |
|---|---|---|
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,854,246 A | 12/1998 | Francois et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,017,912 A | 1/2000 | Bussell |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Resile et al. |
| 6,042,848 A | 3/2000 | Lawyer et al. |
| 6,045,779 A | 4/2000 | Mueller et al. |
| 6,060,041 A | 5/2000 | Candau et al. |
| 6,071,536 A | 6/2000 | Suzuki et al. |
| 6,071,541 A | 6/2000 | Murad |
| 6,075,056 A | 6/2000 | Quigley, Jr. et al. |
| 6,080,394 A | 6/2000 | Lin et al. |
| 6,087,310 A | 7/2000 | Heinkel |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret |
| 6,121,210 A | 9/2000 | Taylor |
| 6,126,920 A | 10/2000 | Jones et al. |
| 6,133,327 A | 10/2000 | Kimura et al. |
| 6,140,355 A | 10/2000 | Egidio et al. |
| 6,146,645 A | 11/2000 | Deckers et al. |

(56) References Cited

U.S. PATENT DOCUMENTS

| | | |
|---|---|---|
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,662 B1 | 1/2001 | Lanzendorfer et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,217,887 B1 | 4/2001 | Beerse et al. |
| 6,221,381 B1 | 4/2001 | Shelford et al. |
| 6,221,823 B1 | 4/2001 | Crisanti et al. |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,241,971 B1 | 6/2001 | Fox et al. |
| 6,251,369 B1 | 6/2001 | Stoltz |
| 6,258,374 B1 | 7/2001 | Friess et al. |
| 6,261,544 B1 | 7/2001 | Coury et al. |
| 6,264,964 B1 | 7/2001 | Mohammadi |
| 6,270,781 B1 | 8/2001 | Gehlsen |
| 6,271,295 B1 | 8/2001 | Powell et al. |
| 6,274,150 B1 | 8/2001 | Simonnet et al. |
| 6,283,336 B1 | 9/2001 | Dwyer et al. |
| 6,284,802 B1 | 9/2001 | Bissett et al. |
| 6,287,546 B1 | 9/2001 | Reich et al. |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,352,727 B1 | 3/2002 | Takahashi |
| 6,355,230 B2 | 3/2002 | Gers-Barlag et al. |
| 6,358,541 B1 | 3/2002 | Goodman |
| 6,358,924 B1 | 3/2002 | Hoffmann |
| 6,364,854 B1 | 4/2002 | Ferrer et al. |
| 6,372,234 B1 | 4/2002 | Deckers et al. |
| 6,375,936 B1 | 4/2002 | Allard et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 | 5/2002 | Straub et al. |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,423,329 B1 | 7/2002 | Sine et al. |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,433,068 B1 | 8/2002 | Morrison et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,451,777 B1 | 9/2002 | Bradbury et al. |
| 6,455,076 B1 | 9/2002 | Hahn et al. |
| 6,468,989 B1 | 10/2002 | Chang et al. |
| 6,479,058 B1 | 11/2002 | McCadden |
| 6,479,060 B1 | 11/2002 | Jones et al. |
| 6,479,532 B1 | 11/2002 | Kamimura et al. |
| 6,482,810 B1 | 11/2002 | Brem et al. |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,551,604 B1 | 4/2003 | Beck et al. |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,607,716 B1 | 8/2003 | Smith et al. |
| 6,610,315 B2 | 8/2003 | Scholz et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy |
| 6,682,726 B2 | 1/2004 | Marchesi et al. |
| 6,682,750 B2 | 1/2004 | Loeffler et al. |
| 6,691,898 B2 | 2/2004 | Hurray et al. |
| 6,706,290 B1 | 3/2004 | Kajander et al. |
| 6,709,663 B2 | 3/2004 | Espinoza |
| 6,723,309 B1 | 4/2004 | Deane |
| 6,730,288 B1 | 5/2004 | Abram |
| 6,736,860 B2 | 5/2004 | Patel et al. |
| 6,753,000 B2 | 6/2004 | Breton et al. |
| 6,753,013 B1 | 6/2004 | Didriksen et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,841,547 B2 | 1/2005 | Brown et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,897,195 B2 | 5/2005 | Su et al. |
| 6,902,737 B2 | 6/2005 | Quemin et al. |
| 6,911,211 B2 | 6/2005 | Eini et al. |
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,986,883 B2 | 1/2006 | Pellico |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |

(56) References Cited

U.S. PATENT DOCUMENTS

| | | |
|---|---|---|
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 * | 6/2011 | Sato et al. |
| 8,114,385 B2 | 2/2012 | Tamarkin et al. |
| 8,119,106 B2 | 2/2012 | Tamarkin et al. |
| 8,119,109 B2 | 2/2012 | Tamarkin et al. |
| 8,158,109 B2 | 4/2012 | Abram et al. |
| 8,192,749 B2 | 6/2012 | Ashley |
| 8,211,874 B2 | 7/2012 | Theobald et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,374 B2 | 7/2013 | Tamarkin et al. |
| 8,486,375 B2 | 7/2013 | Tamarkin et al. |
| 8,486,376 B2 | 7/2013 | Friedman et al. |
| 8,512,718 B2 | 8/2013 | Eini et al. |
| 8,518,376 B2 | 8/2013 | Tamarkin et al. |
| 8,592,380 B2 | 11/2013 | Trumbore et al. |
| 8,617,100 B2 | 12/2013 | Eini et al. |
| 8,618,081 B2 | 12/2013 | Tamarkin et al. |
| 8,623,330 B2 | 1/2014 | Gurge et al. |
| 8,636,982 B2 | 1/2014 | Tamarkin et al. |
| 8,652,443 B2 | 2/2014 | Varanasi et al. |
| 8,709,385 B2 | 4/2014 | Tamarkin et al. |
| 8,722,021 B2 | 5/2014 | Friedman et al. |
| 8,735,377 B1 | 5/2014 | Sipos |
| 8,741,265 B2 | 6/2014 | Tamarkin et al. |
| 8,778,365 B1 | 7/2014 | Hardas et al. |
| 8,784,780 B2 | 7/2014 | Gurge et al. |
| 8,795,693 B2 | 8/2014 | Tamarkin et al. |
| 8,846,039 B2 | 9/2014 | Chung et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 8,945,516 B2 * | 2/2015 | Tamarkin et al. .............. 424/43 |
| 8,992,896 B2 | 3/2015 | Tamarkin et al. |
| 9,050,253 B2 | 6/2015 | Tamarkin et al. |
| 9,101,662 B2 | 8/2015 | Tamarkin et al. |
| 9,192,558 B2 | 11/2015 | Chen et al. |
| 9,265,740 B2 | 2/2016 | Johnston et al. |
| 9,271,930 B2 | 3/2016 | At |
| 9,439,857 B2 | 9/2016 | Tamarkin et al. |
| 9,474,720 B2 | 10/2016 | Yamamoto |
| 9,492,412 B2 | 11/2016 | Tamarkin et al. |
| 9,539,208 B2 | 1/2017 | Tamarkin et al. |
| 9,539,266 B2 | 1/2017 | Mansouri |
| 9,549,898 B2 | 1/2017 | Tamarkin et al. |
| 9,572,775 B2 | 2/2017 | Tamarkin et al. |
| 9,592,246 B2 | 3/2017 | Salman et al. |
| 9,622,947 B2 | 4/2017 | Tamarkin et al. |
| 9,636,405 B2 | 5/2017 | Tamarkin et al. |
| 9,662,298 B2 | 5/2017 | Tamarkin et al. |
| 9,668,972 B2 | 6/2017 | Tamarkin et al. |
| 9,675,700 B2 | 6/2017 | Tamarkin et al. |
| 9,682,021 B2 | 6/2017 | Tamarkin et al. |
| 9,713,643 B2 | 7/2017 | Friedman et al. |
| 9,795,564 B2 | 10/2017 | Tamarkin et al. |
| 9,849,142 B2 | 12/2017 | Tamarkin et al. |
| 9,884,017 B2 | 2/2018 | Tamarkin et al. |
| 9,931,328 B2 | 4/2018 | Kandavilli et al. |
| 10,029,013 B2 | 7/2018 | Tamarkin et al. |
| 2001/0006654 A1 | 7/2001 | Cannell et al. |
| 2001/0026790 A1 | 10/2001 | Gers-Barlag et al. |
| 2001/0027218 A1 | 10/2001 | Stern et al. |
| 2001/0027981 A1 | 10/2001 | Yquel |
| 2001/0033838 A1 | 10/2001 | Farmer |
| 2001/0036450 A1 | 11/2001 | Verite et al. |
| 2001/0054574 A1 | 12/2001 | Navarro |
| 2002/0002151 A1 | 1/2002 | Ono et al. |
| 2002/0004063 A1 | 1/2002 | Zhang |
| 2002/0013481 A1 | 1/2002 | Schonrock et al. |
| 2002/0015721 A1 | 2/2002 | Simonnet et al. |
| 2002/0031478 A1 | 3/2002 | Keller et al. |
| 2002/0032171 A1 | 3/2002 | Chen et al. |
| 2002/0035046 A1 | 3/2002 | Lukenbach et al. |
| 2002/0035070 A1 | 3/2002 | Gardlik et al. |
| 2002/0035087 A1 | 3/2002 | Barclay |
| 2002/0035182 A1 | 3/2002 | L'Alloret et al. |
| 2002/0039591 A1 | 4/2002 | Dahle |
| 2002/0044659 A1 | 4/2002 | Ohta |
| 2002/0045659 A1 | 4/2002 | Michelet et al. |
| 2002/0048798 A1 | 4/2002 | Avery et al. |
| 2002/0058010 A1 | 5/2002 | Picard-Lesboueyries et al. |
| 2002/0072544 A1 | 6/2002 | Miller et al. |
| 2002/0090386 A1 | 7/2002 | Haslwanter et al. |
| 2002/0098215 A1 | 7/2002 | Douin et al. |
| 2002/0111281 A1 | 8/2002 | Vishnupad |
| 2002/0117516 A1 | 8/2002 | Lasserre et al. |
| 2002/0134376 A1 | 9/2002 | Castro et al. |
| 2002/0136755 A1 | 9/2002 | Tyrrell et al. |
| 2002/0143188 A1 | 10/2002 | Garvey et al. |
| 2002/0153390 A1 | 10/2002 | Vlodek |
| 2002/0165170 A1 | 11/2002 | Wilson et al. |
| 2002/0182162 A1 | 12/2002 | Shahinpoor et al. |
| 2002/0182234 A1 | 12/2002 | Riedel et al. |
| 2002/0187181 A1 | 12/2002 | Godbey et al. |
| 2002/0198136 A1 | 12/2002 | Mak et al. |
| 2003/0006193 A1 | 1/2003 | Ikeda et al. |
| 2003/0013692 A1 | 1/2003 | Gullans et al. |
| 2003/0017181 A1 | 1/2003 | Rood et al. |
| 2003/0031693 A1 | 2/2003 | Breton et al. |
| 2003/0053961 A1 | 3/2003 | Eccard |
| 2003/0077297 A1 | 4/2003 | Chen et al. |
| 2003/0077301 A1 | 4/2003 | Maibach et al. |
| 2003/0078172 A1 | 4/2003 | Guiramand et al. |
| 2003/0082120 A1 | 5/2003 | Milstein |
| 2003/0108502 A1 | 6/2003 | Uchida et al. |
| 2003/0114520 A1 | 6/2003 | Pereira et al. |
| 2003/0118515 A1 | 6/2003 | Jew et al. |
| 2003/0118527 A1 | 6/2003 | Jager et al. |
| 2003/0129259 A1 | 7/2003 | Mahalingam et al. |
| 2003/0130247 A1 | 7/2003 | Gans et al. |
| 2003/0148949 A1 | 8/2003 | Podolsky |
| 2003/0175232 A1 | 9/2003 | Elliott et al. |
| 2003/0175315 A1 | 9/2003 | Yoo et al. |
| 2003/0180347 A1 | 9/2003 | Young et al. |
| 2003/0185839 A1 | 10/2003 | Podolsky |
| 2003/0185861 A1 | 10/2003 | Hori et al. |
| 2003/0194379 A1 | 10/2003 | Brugger et al. |
| 2003/0195128 A1 | 10/2003 | Deckman et al. |
| 2003/0206955 A1 | 11/2003 | Sonneville-Aubrun et al. |
| 2003/0215418 A1 | 11/2003 | Asmus et al. |
| 2003/0215472 A1 | 11/2003 | Bonda et al. |
| 2003/0235597 A1 | 12/2003 | Withiam et al. |
| 2004/0002550 A1 | 1/2004 | Mercurio |
| 2004/0018228 A1 | 1/2004 | Fischell et al. |
| 2004/0028752 A1 | 2/2004 | Kamm et al. |
| 2004/0038912 A1 | 2/2004 | Michelet et al. |
| 2004/0053797 A1 | 3/2004 | Chen et al. |
| 2004/0058878 A1 | 3/2004 | Walker |
| 2004/0063787 A1 | 4/2004 | Villanueva |
| 2004/0067970 A1 | 4/2004 | Foster et al. |
| 2004/0072638 A1 | 4/2004 | Enos et al. |
| 2004/0076651 A1 | 4/2004 | Brocks et al. |
| 2004/0078896 A1 | 4/2004 | Hellyer et al. |

(56) References Cited

U.S. PATENT DOCUMENTS

| | | |
|---|---|---|
| 2004/0079361 A1 | 4/2004 | Clayton et al. |
| 2004/0105825 A1 | 6/2004 | Henning |
| 2004/0106688 A1 | 6/2004 | Koike et al. |
| 2004/0120917 A1 | 6/2004 | Perrier et al. |
| 2004/0127554 A1 | 7/2004 | Ghisalberti |
| 2004/0138179 A1 | 7/2004 | Goldstein et al. |
| 2004/0151671 A1 | 8/2004 | Abram et al. |
| 2004/0151756 A1 | 8/2004 | Richards et al. |
| 2004/0161447 A1 | 8/2004 | Paul |
| 2004/0184992 A1 | 9/2004 | Abram |
| 2004/0185123 A1 | 9/2004 | Mazzio et al. |
| 2004/0191196 A1 | 9/2004 | Tamarkin |
| 2004/0192754 A1 | 9/2004 | Shapira et al. |
| 2004/0195276 A1 | 10/2004 | Fuchs |
| 2004/0197276 A1 | 10/2004 | Takase et al. |
| 2004/0197295 A1 | 10/2004 | Riedel et al. |
| 2004/0198706 A1 | 10/2004 | Carrara |
| 2004/0219122 A1 | 11/2004 | Masuda et al. |
| 2004/0219176 A1 | 11/2004 | Dominguez |
| 2004/0220187 A1 | 11/2004 | Stephenson et al. |
| 2004/0229813 A1 | 11/2004 | DiPiano et al. |
| 2004/0234475 A1 | 11/2004 | Lannibois-Drean et al. |
| 2004/0241099 A1 | 12/2004 | Popp et al. |
| 2004/0247531 A1 | 12/2004 | Riedel et al. |
| 2004/0253275 A1 | 12/2004 | Eini et al. |
| 2004/0258627 A1 | 12/2004 | Riedel et al. |
| 2004/0258628 A1 | 12/2004 | Riedel et al. |
| 2004/0258643 A1 | 12/2004 | Yaqub et al. |
| 2004/0265240 A1 | 12/2004 | Tamarkin et al. |
| 2005/0002976 A1 | 1/2005 | Wu |
| 2005/0013853 A1 | 1/2005 | Gil-Ad et al. |
| 2005/0031547 A1 | 2/2005 | Tamarkin et al. |
| 2005/0042182 A1 | 2/2005 | Arkin et al. |
| 2005/0054991 A1 | 3/2005 | Tobyn et al. |
| 2005/0069566 A1 | 3/2005 | Tamarkin et al. |
| 2005/0074414 A1 | 4/2005 | Tamarkin et al. |
| 2005/0075407 A1 | 4/2005 | Tamarkin et al. |
| 2005/0079139 A1 | 4/2005 | Jacques et al. |
| 2005/0079228 A1 | 4/2005 | Jaiswal et al. |
| 2005/0084551 A1 | 4/2005 | Jensen et al. |
| 2005/0085843 A1 | 4/2005 | Opolski et al. |
| 2005/0100517 A1 | 5/2005 | Sanzgiri et al. |
| 2005/0101936 A1 | 5/2005 | Gonzales et al. |
| 2005/0106197 A1 | 5/2005 | Blin et al. |
| 2005/0123494 A1 | 6/2005 | Swaile et al. |
| 2005/0123496 A1 | 6/2005 | Shah et al. |
| 2005/0148552 A1 | 7/2005 | Ryan et al. |
| 2005/0153943 A1 | 7/2005 | Ashley |
| 2005/0164993 A1 | 7/2005 | Ashley |
| 2005/0186142 A1 | 8/2005 | Tamarkin et al. |
| 2005/0186147 A1* | 8/2005 | Tamarkin et al. ............... 424/47 |
| 2005/0189377 A1 | 9/2005 | Lanzendorfer et al. |
| 2005/0196414 A1 | 9/2005 | Dake et al. |
| 2005/0205086 A1 | 9/2005 | Tamarkin et al. |
| 2005/0207837 A1 | 9/2005 | Kosh et al. |
| 2005/0222090 A1 | 10/2005 | Cheng et al. |
| 2005/0232869 A1 | 10/2005 | Tamarkin et al. |
| 2005/0244342 A1 | 11/2005 | Friedman et al. |
| 2005/0244354 A1 | 11/2005 | Speron |
| 2005/0245902 A1 | 11/2005 | Cornish et al. |
| 2005/0252995 A1 | 11/2005 | Westphal et al. |
| 2005/0255048 A1 | 11/2005 | Hirsh et al. |
| 2005/0258189 A1 | 11/2005 | Peterson et al. |
| 2005/0266035 A1 | 12/2005 | Healy et al. |
| 2005/0268416 A1 | 12/2005 | Sommers |
| 2005/0271596 A1 | 12/2005 | Friedman et al. |
| 2005/0271598 A1 | 12/2005 | Friedman et al. |
| 2005/0276836 A1 | 12/2005 | Wilson et al. |
| 2005/0281749 A1 | 12/2005 | Willcox et al. |
| 2005/0281755 A1 | 12/2005 | Zarif et al. |
| 2005/0281766 A1 | 12/2005 | Martin et al. |
| 2005/0285912 A1 | 12/2005 | Delametter et al. |
| 2005/0287081 A1 | 12/2005 | Aust et al. |
| 2006/0008432 A1 | 1/2006 | Scarampi et al. |
| 2006/0018937 A1 | 1/2006 | Friedman et al. |
| 2006/0018938 A1 | 1/2006 | Neubourg |
| 2006/0029565 A1 | 2/2006 | Xu et al. |
| 2006/0051301 A1 | 3/2006 | Galopin et al. |
| 2006/0054634 A1 | 3/2006 | Mekata |
| 2006/0057168 A1 | 3/2006 | Larm et al. |
| 2006/0088561 A1 | 4/2006 | Eini et al. |
| 2006/0099151 A1 | 5/2006 | Neubourg |
| 2006/0108377 A1 | 5/2006 | Glynn et al. |
| 2006/0110415 A1 | 5/2006 | Gupta |
| 2006/0110418 A1 | 5/2006 | Johnson |
| 2006/0114745 A1 | 6/2006 | Ollmann et al. |
| 2006/0121073 A1 | 6/2006 | Goyal et al. |
| 2006/0140984 A1 | 6/2006 | Tamarkin et al. |
| 2006/0140990 A1 | 6/2006 | Bortz et al. |
| 2006/0160713 A1 | 7/2006 | Sekine et al. |
| 2006/0165616 A1 | 7/2006 | Brock et al. |
| 2006/0177392 A1 | 8/2006 | Walden |
| 2006/0193789 A1 | 8/2006 | Tamarkin et al. |
| 2006/0193813 A1 | 8/2006 | Simonnet |
| 2006/0204446 A1 | 9/2006 | Lulla et al. |
| 2006/0222675 A1 | 10/2006 | Sabnis et al. |
| 2006/0233721 A1 | 10/2006 | Tamarkin et al. |
| 2006/0239937 A2 | 10/2006 | Neubourg |
| 2006/0251684 A1 | 11/2006 | Annis et al. |
| 2006/0254597 A1 | 11/2006 | Thompson |
| 2006/0263323 A1 | 11/2006 | Hoang et al. |
| 2006/0269485 A1 | 11/2006 | Friedman et al. |
| 2006/0272199 A1 | 12/2006 | Licciardello et al. |
| 2006/0275218 A1 | 12/2006 | Tamarkin et al. |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0010580 A1 | 1/2007 | De Paoli Ambrosi |
| 2007/0015739 A1 | 1/2007 | Walker et al. |
| 2007/0017696 A1 | 1/2007 | Lin et al. |
| 2007/0020213 A1 | 1/2007 | Tamarkin et al. |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0053943 A1 | 3/2007 | Wang et al. |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0111956 A1 | 5/2007 | Matsushima et al. |
| 2007/0134174 A1 | 6/2007 | Irwin et al. |
| 2007/0140998 A1 | 6/2007 | Kato et al. |
| 2007/0140999 A1 | 6/2007 | Puglia et al. |
| 2007/0141086 A1 | 6/2007 | Ohara et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0166274 A1 | 7/2007 | Mazur et al. |
| 2007/0224143 A1 | 9/2007 | Konis |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0050317 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |

(56) References Cited

U.S. PATENT DOCUMENTS

| | | |
|---|---|---|
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0017147 A1 | 1/2009 | Lintner et al. |
| 2009/0041680 A1 | 2/2009 | Tamarkin et al. |
| 2009/0053290 A1 | 2/2009 | Sand et al. |
| 2009/0061001 A1 | 3/2009 | Hougaz |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0214628 A1 | 8/2009 | De Rijk |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0128598 A1 | 5/2010 | Gandhewar et al. |
| 2010/0137198 A1 | 6/2010 | Eini et al. |
| 2010/0221194 A1 | 9/2010 | Loupenok |
| 2010/0221195 A1 | 9/2010 | Tamarkin et al. |
| 2010/0247449 A1 | 9/2010 | Graupe et al. |
| 2010/0266510 A1 | 10/2010 | Tamarkin et al. |
| 2010/0286417 A1 | 11/2010 | Mendes et al. |
| 2011/0002857 A1 | 1/2011 | Tamarkin et al. |
| 2011/0002969 A1 | 1/2011 | Serraima et al. |
| 2011/0008266 A1 | 1/2011 | Tamarkin et al. |
| 2011/0045037 A1 | 2/2011 | Tamarkin et al. |
| 2011/0097279 A1 | 4/2011 | Tamarkin et al. |
| 2011/0207765 A1 | 8/2011 | Van Den Bussche et al. |
| 2011/0212033 A1 | 9/2011 | Tamarkin et al. |
| 2011/0262542 A1 | 10/2011 | Ashley |
| 2011/0268665 A1 | 11/2011 | Tamarkin et al. |
| 2011/0281827 A1 | 11/2011 | Tamarkin et al. |
| 2012/0064136 A1 | 3/2012 | Baker, Jr. et al. |
| 2012/0082632 A1 | 4/2012 | Phillips et al. |
| 2012/0087872 A1 | 4/2012 | Tamarkin et al. |
| 2012/0128598 A1 | 5/2012 | Trumbore et al. |
| 2012/0141384 A1 | 6/2012 | Tamarkin |
| 2012/0148503 A1 | 6/2012 | Tamarkin et al. |
| 2012/0156144 A1 | 6/2012 | Tamarkin et al. |
| 2012/0164087 A1 | 6/2012 | Carter |
| 2012/0181201 A1 | 7/2012 | Heggie |
| 2012/0195836 A1 | 8/2012 | Tamarkin et al. |
| 2012/0213709 A1 | 8/2012 | Tamarkin et al. |
| 2012/0213710 A1 | 8/2012 | Tamarkin et al. |
| 2012/0237453 A1 | 9/2012 | Tamarkin et al. |
| 2013/0011342 A1 | 1/2013 | Tamarkin et al. |
| 2013/0028850 A1 | 1/2013 | Tamarkin et al. |
| 2013/0053353 A1 | 2/2013 | Tamarkin et al. |
| 2013/0064777 A1 | 3/2013 | Tamarkin et al. |
| 2013/0115173 A1 | 5/2013 | Trumbore et al. |
| 2013/0161351 A1 | 6/2013 | Eini et al. |
| 2013/0164225 A1 | 6/2013 | Tamarkin et al. |
| 2013/0183250 A1 | 7/2013 | Friedman et al. |
| 2013/0183251 A1 | 7/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0189196 A1 | 7/2013 | Tamarkin et al. |
| 2013/0195769 A1 | 8/2013 | Tamarkin et al. |
| 2013/0225536 A1 | 8/2013 | Tamarkin et al. |
| 2013/0251644 A1 | 9/2013 | Majhi et al. |
| 2013/0261565 A1 | 10/2013 | Wong et al. |
| 2013/0295022 A1 | 11/2013 | Friedman et al. |
| 2013/0296387 A1 | 11/2013 | Saad |
| 2014/0050673 A1 | 2/2014 | Tamarkin et al. |
| 2014/0086848 A1 | 3/2014 | Tamarkin et al. |
| 2014/0121188 A1 | 5/2014 | Tamarkin et al. |
| 2014/0140937 A1 | 5/2014 | Gurge et al. |
| 2014/0147504 A1 | 5/2014 | Salman et al. |
| 2014/0182585 A1 | 7/2014 | Tamarkin et al. |
| 2014/0186269 A1 | 7/2014 | Tamarkin et al. |
| 2014/0186442 A1 | 7/2014 | Mansouri |
| 2014/0193502 A1 | 7/2014 | Tamarkin et al. |
| 2014/0221320 A1 | 8/2014 | Joks et al. |
| 2014/0227199 A1 | 8/2014 | Tamarkin et al. |
| 2014/0228355 A1 | 8/2014 | Kortagere et al. |
| 2014/0242016 A1 | 8/2014 | Binks et al. |
| 2014/0248219 A1 | 9/2014 | Tamarkin et al. |
| 2014/0271494 A1 | 9/2014 | Tamarkin et al. |
| 2015/0025060 A1 | 1/2015 | Tamarkin et al. |
| 2015/0098907 A1 | 4/2015 | Tamarkin et al. |
| 2015/0118164 A1 | 4/2015 | Tamarkin et al. |
| 2015/0125496 A1 | 5/2015 | Yamamoto |
| 2015/0141381 A1 | 5/2015 | Levy et al. |
| 2015/0157586 A1 | 6/2015 | Tamarkin et al. |
| 2015/0164922 A1 | 6/2015 | Tamarkin et al. |
| 2015/0174144 A1 | 6/2015 | Bowser et al. |
| 2015/0190409 A1 | 7/2015 | Tamarkin et al. |
| 2015/0196570 A1 | 7/2015 | Tamarkin et al. |
| 2015/0209296 A1 | 7/2015 | Yamamoto |
| 2015/0374625 A1 | 12/2015 | Tamarkin et al. |
| 2016/0101051 A1 | 4/2016 | Tamarkin et al. |
| 2016/0101184 A1 | 4/2016 | Tamarkin et al. |
| 2016/0128944 A1 | 5/2016 | Chawrai et al. |
| 2016/0158261 A1 | 6/2016 | Friedman et al. |
| 2016/0213757 A1 | 7/2016 | Edelson et al. |
| 2016/0279152 A1 | 9/2016 | Chen et al. |
| 2016/0287615 A1 | 10/2016 | Chan et al. |
| 2016/0354473 A1 | 12/2016 | Tamarkin et al. |
| 2016/0361252 A1 | 12/2016 | Franke |
| 2016/0361320 A1 | 12/2016 | Zhao et al. |
| 2017/0014517 A1 | 1/2017 | Tamarkin |
| 2017/0049712 A1 | 2/2017 | Bhalani et al. |
| 2017/0119665 A1 | 5/2017 | Tamarkin et al. |
| 2017/0157175 A1 | 6/2017 | Tamarkin et al. |
| 2017/0172857 A1 | 6/2017 | Tamarkin et al. |
| 2017/0181970 A1 | 6/2017 | Tamarkin et al. |
| 2017/0216334 A1 | 8/2017 | Tamarkin et al. |
| 2017/0231909 A1 | 8/2017 | Tamarkin et al. |
| 2017/0274084 A1 | 9/2017 | Friedman et al. |
| 2017/0340743 A1 | 11/2017 | Tamarkin et al. |
| 2017/0348418 A1 | 12/2017 | Tamarkin et al. |
| 2017/0354597 A1 | 12/2017 | Tamarkin et al. |
| 2017/0360705 A1 | 12/2017 | Tamarkin et al. |
| 2018/0000734 A1 | 1/2018 | Tamarkin et al. |
| 2018/0064638 A1 | 3/2018 | Tamarkin et al. |
| 2018/0147218 A1 | 5/2018 | Tamarkin et al. |
| 2018/0153804 A1 | 6/2018 | Tamarkin et al. |
| 2018/0193468 A1 | 7/2018 | Tamarkin et al. |
| 2018/0193469 A1 | 7/2018 | Tamarkin et al. |
| 2018/0214558 A1 | 8/2018 | Tamarkin et al. |
| 2018/0235984 A1 | 8/2018 | Eini et al. |

FOREIGN PATENT DOCUMENTS

| | | |
|---|---|---|
| AU | 2010219295 | 9/2012 |
| CA | 2114537 | 2/1993 |
| CA | 2154438 | 1/1996 |
| CA | 2422244 | 9/2003 |
| CA | 2502986 | 8/2011 |
| CA | 2534372 | 1/2012 |
| CA | 2536482 | 7/2012 |
| CH | 639913 | 12/1983 |
| DE | 1 882 100 | 11/1963 |
| DE | 1926796 | 11/1965 |

(56) References Cited

FOREIGN PATENT DOCUMENTS

| | | |
|---|---|---|
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 52404 | 5/1982 |
| EP | 0 156 507 | 10/1985 |
| EP | 0 186 453 | 7/1986 |
| EP | 0 211 550 | 2/1987 |
| EP | 0 213 827 | 3/1987 |
| EP | 0 214 865 | 3/1987 |
| EP | 0 216 856 | 4/1987 |
| EP | 0 270 316 | 6/1988 |
| EP | 0 297 436 | 1/1989 |
| EP | 0 326 196 | 8/1989 |
| EP | 0 336 812 | 10/1989 |
| EP | 0 391 124 | 10/1990 |
| EP | 0 404 376 | 12/1990 |
| EP | 0 414 920 | 3/1991 |
| EP | 0 454 102 A2 | 10/1991 |
| EP | 0 484 530 | 5/1992 |
| EP | 0 485 299 | 5/1992 |
| EP | 0 488 089 | 6/1992 |
| EP | 0 504 301 | 9/1992 |
| EP | 0 528 190 | 2/1993 |
| EP | 0 535 327 | 4/1993 |
| EP | 0 552 612 | 7/1993 |
| EP | 0 569 773 | 11/1993 |
| EP | 0 598 412 | 5/1994 |
| EP | 0 662 431 | 7/1995 |
| EP | 0 676 198 | 10/1995 |
| EP | 0 738 516 | 10/1996 |
| EP | 0 757 959 | 2/1997 |
| EP | 0 824 911 | 2/1998 |
| EP | 0 829 259 | 3/1998 |
| EP | 0 928 608 | 7/1999 |
| EP | 0 979 654 | 2/2000 |
| EP | 0 993 827 | 4/2000 |
| EP | 1 025 836 | 8/2000 |
| EP | 1 055 425 | 11/2000 |
| EP | 0 506 197 | 7/2001 |
| EP | 1 215 258 | 6/2002 |
| EP | 1 287 813 | 3/2003 |
| EP | 1 308 169 | 5/2003 |
| EP | 1 375 386 | 1/2004 |
| EP | 1 428 521 | 6/2004 |
| EP | 1 438 946 | 7/2004 |
| EP | 1 189 579 | 9/2004 |
| EP | 1 475 381 | 11/2004 |
| EP | 1 483 001 | 12/2004 |
| EP | 1 500 385 | 1/2005 |
| EP | 1 537 916 | 6/2005 |
| EP | 1 600 185 | 11/2005 |
| EP | 1 653 932 | 5/2006 |
| EP | 1 734 927 | 12/2006 |
| EP | 1 758 547 | 3/2007 |
| EP | 1 584 324 | 11/2007 |
| EP | 1 889 609 | 2/2008 |
| EP | 1 902 706 | 3/2008 |
| EP | 2 129 383 | 12/2009 |
| EP | 2422768 | 2/2012 |
| EP | 2494959 | 9/2012 |
| FR | 2 456 522 | 12/1980 |
| FR | 2 591 331 | 6/1987 |
| FR | 2 640 942 | 6/1990 |
| FR | 2 736 824 | 1/1997 |
| FR | 2 774 595 | 8/1999 |
| FR | 2 789 371 | 8/2000 |
| FR | 2 793 479 | 11/2000 |
| FR | 2 814 959 | 4/2002 |
| FR | 2 833 246 | 6/2003 |
| FR | 2 840 903 | 12/2003 |
| FR | 2 843 373 | 2/2004 |
| FR | 2 845 672 | 4/2004 |
| FR | 2 848 998 | 6/2004 |
| FR | 2 860 976 | 4/2005 |
| FR | 2 915 891 | 11/2008 |
| GB | 808 104 | 1/1959 |
| GB | 808 105 | 1/1959 |
| GB | 922 930 | 4/1963 |
| GB | 933 486 | 8/1963 |
| GB | 998 490 | 7/1965 |
| GB | 1 026 831 | 4/1966 |
| GB | 1 033 299 | 6/1966 |
| GB | 1 081 949 | 9/1967 |
| GB | 1 121 358 | 7/1968 |
| GB | 1 162 684 | 8/1969 |
| GB | 1 170 152 | 11/1969 |
| GB | 1 201 918 | 8/1970 |
| GB | 1 347 950 | 2/1974 |
| GB | 1 351 761 | 5/1974 |
| GB | 1 351 762 | 5/1974 |
| GB | 1 353 381 | 5/1974 |
| GB | 1 376 649 | 12/1974 |
| GB | 1 397 285 | 6/1975 |
| GB | 1 408 036 | 10/1975 |
| GB | 1 457 671 | 12/1976 |
| GB | 1 489 672 | 10/1977 |
| GB | 2 004 746 | 4/1979 |
| GB | 1 561 423 | 2/1980 |
| GB | 2 114 580 | 8/1983 |
| GB | 2 153 686 | 8/1985 |
| GB | 2 172 298 | 9/1986 |
| GB | 2 206 099 | 12/1988 |
| GB | 2 166 651 | 5/1996 |
| GB | 2 337 461 | 11/1999 |
| GB | 2 367 809 | 4/2002 |
| GB | 2 406 330 | 3/2005 |
| GB | 2 406 791 | 4/2005 |
| GB | 2 474 930 | 7/2012 |
| IL | 49491 | 9/1979 |
| IL | 152 486 | 5/2003 |
| JP | 60001113 | 4/1978 |
| JP | 55069682 | 5/1980 |
| JP | 57044429 | 3/1982 |
| JP | 56039815 | 4/1984 |
| JP | 61275395 | 12/1986 |
| JP | 62241701 | 10/1987 |
| JP | 63119420 | 5/1988 |
| JP | 1100111 | 4/1989 |
| JP | 1156906 | 6/1989 |
| JP | 2184614 | 7/1990 |
| JP | 2255890 | 10/1990 |
| JP | 4-51958 | 2/1992 |
| JP | 4282311 | 10/1992 |
| JP | 4312521 | 11/1992 |
| JP | 5070340 | 3/1993 |
| JP | 5213734 | 8/1993 |
| JP | 6100414 | 4/1994 |
| JP | H06-263630 | 6/1994 |
| JP | 6329532 | 11/1994 |
| JP | 2007/155667 | 6/1995 |
| JP | 7215835 | 8/1995 |
| JP | 2008/040899 | 2/1996 |
| JP | 8501529 | 2/1996 |
| JP | 8119831 | 5/1996 |
| JP | 8165218 | 6/1996 |
| JP | 8277209 | 10/1996 |
| JP | 09 084855 | 3/1997 |
| JP | 9099553 | 4/1997 |
| JP | 9110636 | 4/1997 |
| JP | 10114619 | 5/1998 |
| JP | 3050289 | 9/1998 |
| JP | 2010/332456 | 12/1998 |
| JP | 11501045 | 1/1999 |
| JP | 11250543 | 9/1999 |
| JP | 2000/017174 | 1/2000 |
| JP | 2000/080017 | 3/2000 |
| JP | 2000/128734 | 5/2000 |
| JP | 2000/191429 | 7/2000 |
| JP | 2000/239140 | 9/2000 |
| JP | 2000/351726 | 12/2000 |
| JP | 2000/354623 | 12/2000 |
| JP | 2001/002526 | 1/2001 |

(56) References Cited

FOREIGN PATENT DOCUMENTS

| | | |
|---|---|---|
| JP | 2001/019606 | 1/2001 |
| JP | 2001/072963 | 3/2001 |
| JP | 2002/012513 | 1/2002 |
| JP | 2002/047136 | 2/2002 |
| JP | 2002/524490 | 8/2002 |
| JP | 2002/302419 | 10/2002 |
| JP | 2003/012511 | 1/2003 |
| JP | 2003/055146 | 2/2003 |
| JP | 2004/047136 | 2/2004 |
| JP | 2004/250435 | 9/2004 |
| JP | 2004/348277 | 12/2004 |
| JP | 2005/314323 | 11/2005 |
| JP | 2005/350378 | 12/2005 |
| JP | 2006/008574 | 1/2006 |
| JP | 2006/036317 | 2/2006 |
| JP | 2006/103799 | 4/2006 |
| JP | 2006525145 | 11/2006 |
| JP | 2007/131539 | 5/2007 |
| JP | 2007326996 | 12/2007 |
| KR | 143232 | 7/1998 |
| KR | 2001/003063 | 1/2001 |
| NZ | 520014 | 5/2005 |
| NZ | 540166 | 6/2007 |
| RU | 2277501 | 6/2006 |
| UA | 66796 | 6/2004 |
| WO | 82/001821 | 6/1982 |
| WO | 86/05389 | 9/1986 |
| WO | 88/01502 | 3/1988 |
| WO | 88/01863 | 3/1988 |
| WO | 88/08316 | 11/1988 |
| WO | 89/06537 | 7/1989 |
| WO | 90/05774 | 5/1990 |
| WO | 91/11991 | 8/1991 |
| WO | 92/00077 | 1/1992 |
| WO | 92/005142 | 4/1992 |
| WO | 92/05763 | 4/1992 |
| WO | 92/11839 | 7/1992 |
| WO | WO 92/13602 | 8/1992 |
| WO | 93/025189 | 12/1993 |
| WO | 94/006440 | 3/1994 |
| WO | 96/03115 | 2/1996 |
| WO | 96/19921 | 7/1996 |
| WO | 96/24325 | 8/1996 |
| WO | 96/26711 | 9/1996 |
| WO | 96/27376 | 9/1996 |
| WO | 96/39119 | 12/1996 |
| WO | 97/03638 | 2/1997 |
| WO | 97/39745 | 10/1997 |
| WO | 98/017282 | 4/1998 |
| WO | 98/18472 | 5/1998 |
| WO | 98/19654 | 5/1998 |
| WO | 98/21955 | 5/1998 |
| WO | 98/23291 | 6/1998 |
| WO | WO 98/31339 | 7/1998 |
| WO | 98/36733 | 8/1998 |
| WO | 98/52536 | 11/1998 |
| WO | 99/08649 | 2/1999 |
| WO | 99/20250 | 4/1999 |
| WO | 99/37282 | 7/1999 |
| WO | 99/53923 | 10/1999 |
| WO | 00/09082 | 2/2000 |
| WO | 00/15193 | 3/2000 |
| WO | 00/023051 | 4/2000 |
| WO | WO 00/62776 | 4/2000 |
| WO | 00/33825 | 6/2000 |
| WO | 00/38731 | 7/2000 |
| WO | 00/61076 | 10/2000 |
| WO | 00/76461 | 12/2000 |
| WO | WO 00/72805 | 12/2000 |
| WO | 01/05366 | 1/2001 |
| WO | WO 01/001949 | 1/2001 |
| WO | 01/08681 | 2/2001 |
| WO | 01/010961 | 2/2001 |
| WO | 01/053198 | 7/2001 |
| WO | 01/054212 | 7/2001 |
| WO | 01/54679 | 8/2001 |
| WO | 01/62209 | 8/2001 |
| WO | 01/70242 | 9/2001 |
| WO | WO 2001/76579 A1 | 10/2001 |
| WO | 01/82880 | 11/2001 |
| WO | 01/82890 | 11/2001 |
| WO | 01/85102 | 11/2001 |
| WO | 01/085128 | 11/2001 |
| WO | 01/95728 | 12/2001 |
| WO | 02/00820 | 1/2002 |
| WO | WO 02/07685 | 1/2002 |
| WO | 02/15860 | 2/2002 |
| WO | 02/015873 | 2/2002 |
| WO | WO 02/24161 | 3/2002 |
| WO | 02/28435 | 4/2002 |
| WO | 02/41847 | 5/2002 |
| WO | 02/43490 | 6/2002 |
| WO | 02/062324 | 8/2002 |
| WO | 02/078667 | 10/2002 |
| WO | 02/087519 | 11/2002 |
| WO | 03/000223 | 1/2003 |
| WO | 03/002082 | 1/2003 |
| WO | WO 03/005985 | 1/2003 |
| WO | 03/013984 | 2/2003 |
| WO | WO 03/015699 | 2/2003 |
| WO | 03/051294 | 6/2003 |
| WO | 03/053292 | 7/2003 |
| WO | 03/055445 | 7/2003 |
| WO | 03/055454 | 7/2003 |
| WO | 03/070301 | 8/2003 |
| WO | 03/071995 | 9/2003 |
| WO | 03/075851 | 9/2003 |
| WO | 03/092641 | 11/2003 |
| WO | 03/097002 | 11/2003 |
| WO | WO 03/094873 | 11/2003 |
| WO | 04/017962 | 3/2004 |
| WO | 04/037197 | 5/2004 |
| WO | 04/037225 | 5/2004 |
| WO | 04/03284 | 8/2004 |
| WO | 04/064769 | 8/2004 |
| WO | 04/064833 | 8/2004 |
| WO | 04/071479 | 8/2004 |
| WO | 04/078158 | 9/2004 |
| WO | 04/078896 | 9/2004 |
| WO | 04/093895 | 11/2004 |
| WO | 04/112780 | 12/2004 |
| WO | 05/011567 | 2/2005 |
| WO | 05/018530 | 3/2005 |
| WO | 05/032522 | 4/2005 |
| WO | 05/044219 | 5/2005 |
| WO | 05/063224 | 7/2005 |
| WO | 05/065652 | 7/2005 |
| WO | 05/076697 | 8/2005 |
| WO | 05/097068 | 10/2005 |
| WO | 05/102282 | 11/2005 |
| WO | 05/102539 | 11/2005 |
| WO | 05/117813 | 12/2005 |
| WO | 06/003481 | 1/2006 |
| WO | 06/010589 | 2/2006 |
| WO | 06/011046 | 2/2006 |
| WO | 06/020682 | 2/2006 |
| WO | 06/028339 | 3/2006 |
| WO | 06/031271 | 3/2006 |
| WO | 06/045170 | 5/2006 |
| WO | 06/079632 | 8/2006 |
| WO | 06/081327 | 8/2006 |
| WO | 06/091229 | 8/2006 |
| WO | 06/100485 | 9/2006 |
| WO | 06/120682 | 11/2006 |
| WO | 06/121610 | 11/2006 |
| WO | 06/122158 | 11/2006 |
| WO | 06/129161 | 12/2006 |
| WO | 06/131784 | 12/2006 |
| WO | 07/007208 | 1/2007 |
| WO | WO 07/010494 | 1/2007 |
| WO | 07/012977 | 2/2007 |
| WO | 07/023396 | 3/2007 |
| WO | 07/031621 | 3/2007 |
| WO | 07/039825 | 4/2007 |

(56) References Cited

FOREIGN PATENT DOCUMENTS

| | | |
|---|---|---|
| WO | 07/050543 | 5/2007 |
| WO | 07/054818 | 5/2007 |
| WO | 07/072216 | 6/2007 |
| WO | WO 07/082698 | 7/2007 |
| WO | 07/085899 | 8/2007 |
| WO | 07/085902 | 8/2007 |
| WO | 07/099396 | 9/2007 |
| WO | 07/111962 | 10/2007 |
| WO | 08/008397 | 1/2008 |
| WO | 08/010963 | 1/2008 |
| WO | 08/038147 | 4/2008 |
| WO | 08/041045 | 4/2008 |
| WO | 08/075207 | 6/2008 |
| WO | 08/087148 | 7/2008 |
| WO | 08/110872 | 9/2008 |
| WO | WO 08/104734 | 9/2008 |
| WO | 08/152444 | 12/2008 |
| WO | 09/007785 | 1/2009 |
| WO | 09/069006 | 6/2009 |
| WO | 09/072007 | 6/2009 |
| WO | 09/087578 | 7/2009 |
| WO | 09/090495 | 7/2009 |
| WO | 09/090558 | 7/2009 |
| WO | 09/098595 | 8/2009 |
| WO | WO 11/006026 | 1/2011 |
| WO | WO 2011/013008 A2 | 2/2011 |
| WO | WO 2011/013009 A2 | 2/2011 |
| WO | WO 11/026094 | 3/2011 |
| WO | 11/039637 | 4/2011 |
| WO | 11/039638 | 4/2011 |
| WO | WO 11/064631 | 6/2011 |
| WO | WO 11/106026 | 9/2011 |
| WO | WO 11/138678 | 11/2011 |
| WO | WO 13/136192 | 9/2013 |
| WO | WO 14/134394 | 9/2014 |
| WO | WO 14/134427 | 9/2014 |
| WO | WO 14/151347 | 9/2014 |
| WO | WO 14/201541 | 12/2014 |
| WO | WO 05/009416 | 2/2015 |
| WO | WO 15/075640 | 5/2015 |
| WO | WO 15/114320 | 8/2015 |
| WO | WO 15/153864 | 10/2015 |
| WO | WO 2017/029647 A1 | 2/2017 |
| WO | WO 2017/030555 A1 | 2/2017 |

OTHER PUBLICATIONS

U.S. Appl. No. 61/322,148, filed Apr. 8, 2010, Tamarkin.
U.S. Appl. No. 61/363,577, filed Jul. 12, 2010, Eini.
"Burn patients need vitamin D supplements." *Decision News Media*, Jan. 23, 2004, http://www.nutraingredients.com/Research/Burn-patients-need-vitamin-D-supplements, Accessed: May 5, 2010.
"HLB Systems", http://pharmcal.tripod.com/ch17.htm, Accessed Sep. 17, 2010, pp. 1-3.
"Minocycline" accessed on Oct. 21, 2011 at en.wikipedia.org/wiki/Minocycline, 7 pages.
"Reaction Rate" Accessed at en.wikipedia.org/wiki/Reaction_rate on Dec. 18, 2011, 6 pages.
'Niram Chemicals' [online]. Niram Chemicals, [retrieved on Jul. 17, 2012]. Retrieved from the Internet: <URL: http://www.indiamart.com/niramchemicals/chemicals.html>, 7 pages.
'Surfactant' [online]. Wikipedia, 2010, [retrieved on Oct. 24, 2010]. Retrieved from the Internet: <URL: http://en.wikipedia.org/wiki/Surfactant>, 7 pages.
Adachi, Shuji. "Storage and Oxidative Stability of O/W/ Nano-emulsions." Foods Food Ingredients. J. Jpn. vol. 209, No. 11. 2004. 1 page.
Alcohol SDA 40B.http://www.pharmco-prod.com/pp./MSDS/SDA.sub.--40B.sub.--200.pdf Accessed Dec. 9, 2008, 2 pages.
Ambrose, Ursula et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.
Anton, N. et al. "Water-in-Oil Nano-Emulsion Formation by the phase inversion Temperature Method: A Novel and General Concept, a New Template for Nanoencapsulation," *Proceedings of the 33rd Annual Meeting and Exposition of the Controlled Release Society*, Jul. 2006, Vienna, Austria, 2 pages.
Arct et al., "Common Cosmetic Hydrophilic Ingredients as Penetration Modifiers of Flavonoids", International Journal of Cosmetic Science, 24(6):357-366 (2002)—Abstract, 1 page.
Arisan, http://www.arisankimya.com/kozmetik.htm Accessed Dec. 10, 2008, 8 pages.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.
Austria, et al., "Stability of Vitamin C Derivatives in Solution and Topical Formulations", Journal of Pharmaceutical and Biomedical Analysis, 15:795-801 (1997).
Barry and Badal, "Stability of minocycline, doxycycline, and tetracycline stored in agar plates and microdilution trays," *Current Microbiology*, 1978, 1:33-36.
Barry, B.W. et al, Comparative bio-availability and activity of proprietary topical corticosteroid preparations: vasoconstrictor assays on thirty-one ointments, British Journal of Dermatology, 93, 563-571, 1975.
Benet, et al., Application of NMR for the Determination of HLB Values of Nonionic Surfactants, Journal of the American Oil Chemists Society, vol. 49, 1972, 499-500.
Bernstein, et al., Effects of the Immunomodulating Agent R837 on Acute and Latent Herpes Simplex Virus Type 2 Invections, Antimicrobial Agents and Chemotherapy, 33(9):1511-1515 (1989).
Blute, "Phase behavior of alkyl glycerol ether surfactants", Physical Chemistry Tenside Sur. Det., 35(3):207-212 (1998).
Brenes, et al., "Stability of Copigmented Anthocyanins and Asorbics Acid in a Grape Juice Model System", J. Agric Food Chem, 53(1):49-56 (2005)—Abstrace, 1 page.
Bronopol. Revtrieved online on Jun. 4, 2011. <URL:http://chemicalland21.com/specialtychem/perchem/BRONOPOL.html>. Jul. 17, 2006. 4 pages.
Buck, et al., "Treatment of Vaginal Intraephithelial Neoplasia (Primarily Low Grade) with Imiquimod 5% Cream", Journal of Lower Genetial Tract Disease, 7(3):290-293 (2003).
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Bunker,et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).
Burton, et al., "Hypertrichosis Due to Minoxidil", British Journal of Dermatology, 101:593-595 (1979).
Campos, et al., "Ascorbic Acid and Its Derivatives in Cosmetic Formulations", Cosmetics and Toiletries, 115(6):59-62 (2000)—Abstract, 1 page.
Carbowax 1000MSDS; http://www.sciencelab.com/xMSDS-Polyethylene.sub.--glycol.sub.--1000-9926-622. Accessed Dec. 13, 2008, 6 pages.
Carelli, et al., "Effect of Vehicles on Yohimbine Permeation Across Excised Hairless Mouse Skin", Pharm Acta Helv, 73(3):127-134 (1998)—Abstract, 1 page.
Chebil, et al., "Soulbility of Flavonoids in Organic Solvents", J. Chem. Eng. Data, 52(5):1552-1556 (2007)—Abstract, 1 page.
Cheshire, et al., Disorders of Sweating, www.medscape.com, Semin Neurol 23(4):399-406, 2003.
Chevrant-Breton, et al., "Etude du Traitement Capillaire <<Bioscalin>> dans les Alopecies Diffuses de la Femme", Gazette Medicale, 93(17):75-79 (1986) [English abstract].
Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.

(56) References Cited

OTHER PUBLICATIONS

Chinnian, et al., "Photostability Profiles of Minoxidil Solutions", PDA J. Pharm Sci Technol., 50(2):94-98 (1996)—Abstract, 1 page.
Chollet, et al., "Development of a Topically Active Imiquimod Formulation", Pharmaceutical Development and Technology, 4(1):35-43 (1999).
Chollet, et al., "The Effect of Temperatures on the Solubility of Immiquimod in Isostearic Acid", Abstract 3031, Pharmaceutical Research, vol. 14, No. 11 Supplemental (November), p. S475 (1997), 2 pages.
Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
Colloidal Silica. Retrieved online on Jun. 4, 2011. <URL:http://www.grace.com/engineeredmaterials/materialsciences/colloidalsilica/default.aspx>. Copyright 2011. 4 pages.
Croda 2. Croda Cetomacrogol 1000 Product Information Sheet. 2011 (no month given). 1 page.
Croda. Aracel 165 Product Summary. 2011 (no month given). 1 page.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Dawber, et al., "Hypertrichosis in Females Applying Minoxidil Topical Solution and in Normal Controls", JEADV, 17:271-275 (2003).
Denatonium Benzoate http://www.newdruginfo.com/pharmaceopeia/usp28/v28230/usp28nf23s0.sub.--m-22790.htm Accessed Dec. 9, 2008, 2 pages.
Dentinger, et al., "Stability of Nifedipine in an Extemporaneously Compounded Oral Solution", American Journal of Health-System Pharmacy, 60(10):1019-1022 (2003)—Abstract, 1 page.
Disorder. (2007). In the American Heritage Dictionary of the English Language. Retrieved from http://www.credoreference.com/entry/hmdictenglang/disorder. 1 page.
Draelos, Z. D. "Antiperspirants and the Hyperhidrosis Patients." Dermatologic Therapy. 2001. vol. 14. pp. 220-224.
Edens, et al., "Storage Stability and Safey of Active Vitamin C in a New Dual-Chamber Dispenser", Journal of Applied Cosmetology, 17(4):136-143 (1999)—Abstract, 1 page.
Edirisinghe, et al., "Effect of fatty acids on endothelium-dependent relaxation in the rabbit aorta", Clin Sci (Load). Aug. 2006; 111(2): 145-51.
Edwards, "Imiquimod in Clinical Practice", J. Am Acad Dermatol., 43(1, Pt 2):S12-S17 (2000)—Abstract, 1 page.
Emulsifiers with HLB values. http://www.theherbarie.com/files/resources-center/formulating/Emulsifiers-.sub.--HLB.sub.--Values.pdf accessed Aug. 5, 2009 (3 pps).
Encyclopedia of Pharmaceutical Technology, Second Edition, vol. 3, Copyright 2002, 4 pages.
Esposito, E. et al. "Nanosystems for Skin Hydration: A Comparative Study." International Journal of Cosmetic Science. 29. 2007. pp. 39-47.
Ethanol, Accessed http://www.sigmaaldrich.com/catalog/ProductDetail.do?N4=E7023SIAL&N5=SEAR- CH.sub.--CONCAT.sub.--PNOBRAND.sub.--KEY&F=SPEC Dec. 9, 2008, 2 pages.
Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.
Farahmand, et al., "Formulation and Evaluation of a Vitamin C Multiple Emulsion", Pharmaceutical Development and Technology, 11(2):255-261 (2006)—Abstract, 1 page.
Final Office Action for U.S. Appl. No. 11/430,437, Tamarkin et al., dated Dec. 16, 2008, 24 pages.
Flick, Cosmetic and Toiletry Formulations, vol. 5, 2nd Edition, Copyright 1996, 63 pages. Relevant pp. 251-309.

Fontana, Anthony J., "Water Activity: Why It is Important for Food Safety," International Conference on Food Safety, Nov. 16-18, 1998, pp. 177-185.
Gallarate, et al., "On the Stability of Ascorbic Acid in Emulsified Systems for Topical and Cosmetic Use", International Journal of Pharmaceutics, 188:233-241 (1999).
Galligan, John et al., "Adhesive Polyurethane Liners for Anterior Restorations," J. Dent. Res., Jul.-Aug. 1968, pp. 629-632.
Gelbard et al. "Primary Pediatric Hyperhidrosis: A Review of Current Treatment Options." Pediatric Dermatology. 2008. 25 (6). pp. 591-598.
Gill, A.M, et al., "Adverse Drug Reactions in a Paediatric Intensive Care Unit," Acta Paediatr 84:438-441, 1995.
Gladkikh, "Ascorbic Acid and Methods of Increasing its Stability in Drugs", Translated from Khimiko-Farmatsevticheskii Zhurnal, 4(12):37-42 (1970)—1 page.
Glaser, et al., Hyperhidrosis: A Comprehensive and Practical Approach to Patient Management, Expert Rev. Dermatol. 1(6), 773-775 (2006).
Graves, S. et al. "Structure of Concentrated Nanoemulsions." The Journal of Chemical Physics.. 122 America Institute of Physics. Published Apr. 1, 2005. 6 pages.
Groveman, et al., "Lack of Efficacy of Polysorbate 60 in the Treatment of Male Pattern Baldness", Arch Intern Med, 145:1454-1458 (1985).
Gschnait, F., et al., "Topical Indomethacin Protects from UVB and UVA Irriadiation," Arch. Dermatol. Res. 276:131-132, 1984.
Hakan, et al., "The protective effect of fish oil enema in acetic acid and ethanol induced colitis," The Turkish Journal of Gasroenterology, 2000, vol. 11, No. 2, pp. 155-161.
Hall, Karla, "Diaper Area Hemangiomas: A Unique Set of Concerns," http://members.tripod.com/.about.Michelle.sub.--G/diaper.html, Dec. 1, 2008, 8 pages.
Hallstar. Retrieved online on Jun. 4, 2011. <URL:http://www.hallstar.com/pis.php?product=1H022>. 1 page.
Hargreaves, "Chemical Formulation, An Overview of Surfactant-Based Preparations Used in Everyday Life", *The Royal Society of Chemistry*, pp. 114-115 (2003).
Harrison, et al., "Effects of cytokines and R-837, a cytokine inducer, on UV-irradiation augmented recurrent genital herpes in guinea pigs", Antivial Res., 15(4):315-322 (1991).
Harrison, et al., "Modification of Immunological Responses and Clinical Disease During Topical R-837 Treatment of Genital HSV-2 Infection", Antiviral Research, 10:209-224 (1988).
Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.
Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).
Hashim, et al. "Tinea versicolor and visceral leishmaniasis," Int J Dermatol., Apr. 1994; 33(4), pp. 258-259 (abstract only).
Heart Failure, The Merck Manual, 2008 <<http://www.merck.com/mmhe/sec03/ch025/ch025a.html>> 12 pages.
Hepburn, NC., "Cutaneous leishmaniasis," Clin Exp Dermatol, Jul. 2000; 25(5), pp. 363-370 (abstract only).
Hill, Randall M. (Ed.) Silicone Surfactants, Table of Contents and Chapter 7, "Silicone Surfactants: Applicants in the Personal Care Industry," by David T. Floyd, 1999 (30 Pages).
Hormones. Http://www.greenwillowtree.com/Page.bok?file=libido.html. Jan. 2001.
http://ibabydoc.com/online/diseaseeczema.asp., Atopic Dermatitis, Copyright 2000, 6 pages.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop. 1 page. Accessed Jan. 31, 2010.
Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.

(56) References Cited

OTHER PUBLICATIONS

Hydroxyethylcellulose. Http: //terpconnect.umd.edu/-choi/MSDS/Sigma-Aldrich/HYDROXYETHYL%20CELLULOSE, 5 pages, Jan. 14, 2004.
ICI Americas Inc. "The HLB System: A Time-Saving Guide to Emulsifier Selection." Mar. 1980. pp. 1-22.
Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
Izquierdo, P. et al. "Formation and Stability of Nano-Emulsions Prepared Using the Phase Inversion Temperature Method." University of Barcelona. Sep. 17, 2001. 1 page.
Jan. "Troubled Times: Detergent Foam." http://zetatalk.com/health/theall7c.htm. Accessed Feb. 9, 2012. 2 pages.
Joseph, "Understanding foams & foaming," University of Minnesota (1997), at http://www.aem.umn.edu/people/faculty/joseph/archive/docs/understandingfoams.pdf, pp. 1-8.
Kalkan, et al., The Measurement of Sweat Intensity Using a New Technique, Tr. J. of Medical Sciences 28, 515-517 (1998).
Kanamoto, et al., "Pharmacokinetics of two rectal dosage forms of ketoprofen in patients after anal surgery," J Pharmacobiodyn., Mar. 1988; 11(3):141-5.
Kang,et al., "Enhancement of the Stability and Skin Penetration of Vitamin C by Polyphenol", Immune Netw., 4(4):250-254 (2004)—Abstract, 1 page.
Karasu, T.B. et al., "Treatment of Patients with Major Depressive Disorder, Second Edition," pp. 1-78, 2000.
Kathon.TM. CG (product information sheet by Rohm and Haas, Jun. 2006).
Kim, "Stability of Minoxidil in Aqueous Solution", Yakhak Hoechi, 30(5):228-231 (1986) Abstract, 1 page.
Kinnunen, "Skin reactions to hexylene glycol," Contact Dermatitis Sep. 1989; 21(3): 154-8.
Kleber, M.D., H.D. et al., "Treatment of Patients with Substance Use Disorders, Second Edition," pp. 1-276, 2006.
Koerber, S., "Humectants and Water Activity," Water Activity News, 2000, ISSN No. 1083-3943.
Kreuter, J. "Nanoparticles and microparticles for drug and vaccine delivery," J. Anat. (1996) 189, pp. 503-505.
Kumar, J. et ak., "Application of Broad Spectrum Antiseptic Povidone Iodine as Powerful Action: A Review," Journal of Pharmaceutical Science and Technology vol. 1(2), 2009, 48-58.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.
Lebwohl et al. "Treatment of Psoriasis. Part 1. Topical Therapy and Phototherapy." *J Am. Acad. Dermatol.* 45:487-498. Oct. 2001.
Lebwohl et al., "A randomized, double-blind, placebo-controlled study of clobestasol propionate 0.05% foam in the treatment of nonscalp psoriasis," *International Journal of Dermatology*, 2002, 41(5): 269-274.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Leung, et al., "Bioadhesive Drug Delivery in Water-Soluble Polymers," American Chemical Society, Chapter 23, 1991, pp. 350-366.
Li, et al., "Solubility Behavior of Imiquimod in Alkanoic Acids", Abstract 3029, Pharmaceutical Research, vol. 14, No. 11 Supplemental (November), p. S475 (1997), 2 pages.
Licking Vaginal Dryness without a Prescription. Accessed http://www.estronaut.com/a/vag.sub.--dryness.htm on Dec. 14, 2008, 3 pages.
Lippacher, A. et al. "Liquid and Semisolid SLN Dispersions for Topical Application" Rheological Characterization. European Journal of Pharmaceutics and Biopharmaceutics. 58. 2004. pp. 561-567.
Lupo, "Antioxidants and Vitamins in Cosmetics", Clinics in Dermatology, 19:467-473 (2001).
Martindale, The extra pharmacopoeia [28th] edition, Eds.: Reynolds, J.E.F. and Prasad, A.B., The Pharmaceutical Press, London, pp. 862-864, 1982.
Martindale. 33 ed. London, Bath Press, 2002. pp. 1073 and 1473.
Material Safety Data Sheet, Progesterone, Apr. 26, 2006, 5 pages.
Material Safety Data Sheet, Science Lab.com, Polyethylene Glycol 1000, MSDS, Nov. 6, 2008, 6 pages.
Merck index, 10th edition, Merck & Co., Inc.: Rahway, NJ, 1983, pp. 39 (entry 242 for allantoin).
Merck index, 14th edition, O'Neill, ed., 2006, entry for p-amino benzoic acid.
Merck index, 14th edition, O'Neill, ed., 2006, entry for zinc oxide.
Merck Index, An Encyclopedia of Chemicals, Drugs, and Biologicals. $13^{th}$ Edition. O'Neil et al eds. Entries 1058, 2350, 6143, and 8803. 2001. 7 pages.
Merck Manual Home Edition. "Excessive Sweating: Sweating Disorders." Accessed Apr. 14, 2011 at www.merckmanuals.com/home/print/sec18/ch206/ch206c.html. 2 pages.
Merriam Webster Online Dictionary [online] retrieved from http://www.merriam-webster.com/cgi-bin/dictionary?book=dictionary&va=derivative on Jul. 5, 2008; 1 page.
Merriam-Webster Online Dictionaary, 2008, "Mousse," Merriam-Webster Online, Dec. 8, 2008 http://www.merriam-webster.com/dictionary/mousse, 2 pages.
Messenger, et al., "Minoxidil: Mechanisms of Action on Hair Growth", British Journal of Dermatology, 150:186-194 (2004).
Metronidazole. www.usp.org/pdf/EN/veterinary/metronidazole.pdf. accessed Sep. 10, 2009, 4 pages.
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Neutrogena. Http://www.cosmetoscope.com/2010/04/neutrogena-clinical-with-johnson-johnsons-cytomimic-techology/. Published Apr. 28, 2010. Accessed Sep. 11, 2010, 5 pages.
Nietz, "Molecular orientation at surfaces of solids," *J. Phys. Chem.*, 1928, 32(2): 255-269.
No Author Listed. "Opitmization of Nano-Emulsions Production by Microfluidization." European Food Research and Technology. vol. 225, No. 5-6. Sep. 2007. Abstract. 1 page.
Office Action for U.S. Appl. No. 11/430,437, Tamarkin et al., dated May 9, 2008, 27 pages.
Office Action received from the U.S. Patent Office, U.S. Appl. No. 11/430,599, dated Jul. 28, 2008 (59 pages).
Oil. Dictionary of Chemistry. Editor: DWA Sharp. Copyright 1990.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
OM Cinnamate. http://www.makingcosmetics.com/sunscreens/OM-Cinnamate-p102.html accessed Sep. 26, 2009, 1 page.
Padhi et al., "Phospho-olicines as positive-electrode materials for rechargeable lithium batteries," *J. Electrochemical Soc.*, 1997, 144(4): 1188-1194.
Pakpayat, et al., "Formulation of Ascorbic Acid Microemulstions with Alkyl Polyglycosides", European Journal of Pharmaceutics and Biopharmaceutics, 72:444-452 (2009).

(56) References Cited

OTHER PUBLICATIONS

Paula. http://ww.cosmeticscop.com/cosmetic-ingredient-dictionary/definition/259/c12-15-alkyl-benzoate.aspx. Printed Oct. 24, 2010. 1 page.
Pendergrass, "The shape and dimension of the human vagina as seen in three-dimensional vinyl polysiloxane casts," Gynecol Obstet. Invest. 1996:42(3):178-82.
Prescription Information for Aldara, Mar. 2007 (29 pages).
Prevent. (2007). In the American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From In Vitro Optimization to In Vivo Efficacy", Skin Pharmacology and Physiology, 17(4):200-206 (2004)—Abstract, 1 page.
Ravet et al., "Electroactivity of natural and synthetic triphylite," *J. of Power Sources*, 2001, 97-98: 503-507.
Raymond, Iodine as an Aerial Disinfectant, Journal of Hygiene, vol. 44, No. 5 (May 1946), pp. 359-361.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Rosacea, http://clinuvel.com/skin-conditions/common-skin-conditions/rosacea#h0-6-prevention. Accessed Sep. 9, 2010, 5 pages.
Savin, et al., "Tinea versicolor treated with terbinafine 1% solution," Int J. Dermatol, Nov. 1999; 38(11), pp. 863-865.
Schmidt A., "Malassezia furfur: a fungus belonging to the physiological skin flora and its relevance in skin disorders," Curtis., Jan. 1997; 59(1), pp. 21-4 (abstract).
Schulze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages).
Scott as Published in Pharmaceutical Dosage Forms; Disperse Systems, vol. 3, Copyright 1998, 120 pages.
Seborrheic Dermatitis, http://www.cumc.columbia.edu/student/health/pdf/R-S/Seborrhea%20Dermatitis.pdf. Access Sep. 9, 2010, 2 pages.
Shear, et al., "Pharmacoeconomic analysis of topical treatments for tinea infections," Pharmacoeconomics. Mar. 1995; 7(3); pp. 251-267 (abstract only).
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Shrestha et al., Forming properties of monoglycerol fatty acid esters in nonpolar oil systems, *Langmuir*, 2006, 22: 8337-8345.
Sigma Aldrich, "HLB-Numbers in Lithography Nanopatterning," http://www.sigmaaldrich.com/materials-science/micro-and-nanoelectronics/1- ithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.
Skin Biology, CP Serum—Copper-Peptide Serum for Skin Regeneration and Reducing Wrinkles, Skin Biology, http;//web.archive.org/web/20030810230608/http://www.skinbio.com/cpserum.- html, Dec. 1, 2008, 21 pages.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 2010, 3 pages.
Smith, Anne. "Sore Nipples." Breastfeeding Mom's Sore Nipples: Breastfeeding Basics. http://breastfeedingbasics.com/articles/sore-nipples. Accessed Feb. 8, 2012. 9 pages.
Sonneville-Aubrun, O. et al. "Nanoemulsions: A New Vehicle for Skincare Products." Advances in Colloid and Interface Science. 108-109 . . . 2004. pp. 145-149.
Squire. J, "A randomised, single-blind, single-centre clinical trial to evaluate comparative clinical efficacy of shampoos containing ciclopirox olamine (1.5%) and salicylic acid (3%), or ketoconazole (2%, Nizoral) for the treatment ofdandruff/seborrhoeic dermatitis," Dermatolog Treat. Jun. 2002;13(2):51-60 (abstract only).
Sreenivasa, et al., "Preparation and Evaluation of Minoxidil Gels for Topical Application in Alopecia", Indian Journal of Pharmaceutical Sciences, 68(4):432-436 (2006), 11 pages.
Stehle et al., Uptake of minoxidil from a new foam formulation devoid of propylene glycol to hamster ear hair follicles, *J. Invest. Dermatol.*, 2005, 124(4), A101.
Sugisaka, et al., "The Physiochemical Properties of Imiquimod, The First Imidazoquinoline Immune Response Modifier", Abstract 3030, Pharmaceutical Research, vol. 14, No. 11 Supplemental (November), p. S475 (1997), 2 pages.
Surfactant. Chemistry Glossary. Http://chemistry.about.com/od/chemistryglossary/g/surfactant.htm, 2012, 1 page.
Sweetman, Sean C. Martindale: The Complete Drug Reference. 33rd Edition. London. Pharmaceutical Press. Jun. 21, 2002. pp. 1073 and 1473. 5 pages.
Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.
Tan et al., "Effect of Carbopol and Polyvinlpyrrolidone on the Mechanical Rheological and Release Properties of Bioadhesive Polyethylene Glycol Gels," AAPS PharmSciTech, 2000; 1(3) Article 24, 2000, 10 pages.
Tanhehco, "Potassium Channel Modulators as Anti-Inflammatory Agents", Expert Opinion on Therapeutic Patents, 11(7):1137-1145 (2001)—Abstract, 3 pages.
Tarumoto, et al., Studies on toxicity of hydrocortisone 17-butyrate 21-propionate-1. Accute toxicity of hydrocortisone 17-butyrate 21-propionate and its analogues in mice, rats and dogs (author's trans), J Toxicol Sci., Jul. 1981; 6 Suppl: 1-16 (Abstract only).
Tata, et al., "Penetration of Minoxidil from Ethanol Propylene Glycol Solutions: Effect of Application Volume on Occlusion", Journal of Pharmaceutical Sciences, 84(6):688-691 (1995).
Tata, et al., "Relative Influence of Ethanol and Propylene Glycol Cosolvents on Deposition of Minoxidil into the Skin", Journal of Pharmaceutical Sciences, 83(10):1508-1510 (1994).
Third Party Submission for U.S. Appl. No. 12/014,088, filed Feb 4, 2009, 4 pages.
Torres-Rodriguez, JM., "New topical antifungal drugs," Arch Med Res. 1993 Winter; 24(4), pp. 371-375 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008, 4 pages.
Trofatter, "Imiquimod in clinical Practice", European Journal of Dermatology, 8(7 Supp.):17-19 (1998)—Abstract, 1 page.
Tsai, et al., "Drug and Vehicle Deposition from Topical Applications: Use of In Vitro Mass Balance Technique with Minosidil Solutions", J. Pharm. Sci., 81(8):736-743 (1992)—Abstract, 1 page.
Tsai, et al., "Effect of Minoxidil Concentration on the Deposition of Drug and Vehicle into the Skin", International Journal of Pharmaceutics, 96(1-3):111-117 (1993)—Abstract, 1 page.
Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).

(56) References Cited

OTHER PUBLICATIONS

Tyring, "Immune-Response Modifiers: A New Paradigm in the Treatment of Human Papillomavirus", Current Therapeutic Research, 61(9):584-596 (2000)—Abstract, 1 page.
Tzen, Jason T.C. et al. "Surface Structure and Properties of Plant Seed Oil Bodies." Department of Botany and Plant Sciences, University of California, Riverside, California 92521. Apr. 15, 1992. 9 pages.
Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.
Veron, et al., "Stability of Minoxidil Topical Formulations", Ciencia Pharmaceutica, 2(6):411-414 (1992), Abstract, 1 page.
Wermuth, C.G. "Similarity in drugs: reflections on analogue design," Drug Discovery Today, vol. 11, Nos. 7/8, Apr. 2006, pp. 348-354.
Williams, "Scale up of an olive/water cream containing 40% diethylene glycol momoethyl ether", Dev. Ind. Pharm., 26(1):71-77 (2000).
Wormser et al., Protective effect of povidone-iodine ointment against skin lesions induced by sulphur and nitrogen mustards and by non-mustard vesicants, Arch. Toxicol., 1997, 71, 165-170.
Wormser, Early topical treatment with providone-iodine ointment reduces, and sometimes prevents, skin damage following heat stimulus, Letter to the Editor, Burns 24, pp. 383, 1998.
Yamada and Chung, "Crystal Chemistry of the Olivine-Type Li($Mn_yFe_{1-y}$)$PO_4$ and ($Mn_yFe_{1-y}$)$PO_4$ as Possible 4 V Cathode Materials for Lithium Batteries," *J. Electrochemical Soc.*, 2001, 148(8): A960-967.
"Coal tars and coal-tar pitches," *Report on Carcinogens, Twelfth Edition*, 2011, 3 pages.
Adisen et al. "Topical tetracycline in the treatment of acne vulgaris," *J Drugs Dermatol.*, 2008, 7:953-5.
Baskaran et al., "Poloxamer-188 improves capillary blood flow and tissue viability in a cutaneous burn wound," *J. Surg. Res.*, 2001, 101(1):56-61.
Bell-Syer et al. "A systematic review of oral treatments for fungal infections of the skin of the feet," *J. Dermatolog. Treat.*, 2001, 12:69-74.
Boehm et al. 1994, "Synthesis of high specific activity [.sup.3 H]-9-cis-retinoic acid and its application for identifying retinoids with unusual binding properties," *J. Med. Chem.*, 37:408-414.
Carapeti et al., "Topical diltiazem and bethanechol decrease anal sphincter pressure and heal anal fissures without side effects," *Dis Colon Rectum*, 2000, 43(10):1359-62.
Cook and Mortensen, "Nifedipine for treatment of anal fissures," *Dis Colon Rectum*, 2000, 43(3):430-1.
Dumortier et al., "A review of poloxamer 407 pharmaceutical and pharmacological characteristics," *Pharmaceutical Res.*, 2006, 23(12):2709-2728.
Ebadi et al., "Healing effect of topical nifedipine on skin wounds of diabetic rats," *DARU*, 2003, 11(1):19-22.
Effendy and Maibach. "Surfactants and Experimental Irritant Contact Dermatitis." *Contact Dermatol.*, 1995, 33:217-225.
Elias and Ghadially, "The aged epidermal permeability barrier," *Clinical Geriatric Medicine*, Feb. 2002, pp. 103-120.
Fantin et al., "Critical influence of resistance to streptogramin B-type antibiotics on activity of RP 59500 (Quinupristin-dalfopristin) in experimental endocarditis due to *Staphylococcus aureus,*" *Antimicrob Agents and Chemothery*, 1999, 39:400-405.
Fluhr et al., "Glycerol accelerates recovery of barrier function in vivo," *Acta Derm. Venereol,*. 1999, 79:418-21.
Garti et al. "Sucrose Esters microemulsions," *J. Molec. Liquids*, 1999, 80:253-296.
Hammer et al. "Anti-Microbial Activity of Essential Oils and other Plant extracts," *J. Applied Microbiology*, 1999, 86:985-990.
Hwang et al. "Isolation and identification of mosquito repellents in *Artemisia vulgaris,*" *J. Chem Ecol.*, 11: 1297-1306, 1985.
Knight et al., "Topical diltiazem ointment in the treatment of chronic anal fissure," *Br. J. Surg.*, 2001, 88(4):553-6.

Kucharekova et al., "Effect of a lipid-rich emollient containing ceramide 3 in experimentally induced skin barrier dysfunction," *Contact Dermatitis*, Jun. 2002, pp. 331-338.
Leive et al, "Tetracyclines of various hydrophobicities as a probe for permeability of *Escherichia coli* outer membrane," *Antimicrobial Agents and Chemotherapy*, 1984, 25:539-544.
Luepke and Kemper, "The HET-CAM Test: An Alternative to the Draize Eye Test," *FD Chem. Toxic.*, 1986, 24:495-196.
Osborne and Henke, "Skin Penetration Enhancers Cited in the Technical Literature," *Pharm. Technology*, Nov. 1997, pp. 58-86.
Padi. "Minocycline prevents the development of neuropathic pain, but not acute pain: possible anti-inflammatory and antioxidant mechanisms," *Eur J. Pharmacol*, 2008, 601:79-87.
Palamaras and Kyriakis, "Calcium antagonists in dermatology: a review of the evidence and research-based studies," *Derm. Online Journal*, 2005, 11(2):8.
Passi et al., Lipophilic antioxidants in human sebum and aging, *Free Radical Research*, 2002, pp. 471-477.
Perrotti et al., "Topical Nifedipine With Lidocaine Ointment vs. Active Control for Treatment of Chronic Anal Fissure," *Dis Colon Rectum*, 2002, 45(11):1468-1475.
Repa et al. "All-trans-retinol is a ligand for the retinoic acid receptors," *Proc. Natl. Acad Sci, USA*, 90: 7293-7297, 1993.
Ruledge, "Some corrections to the record on insect repellents and attractants," *J. Am. Mosquito Control Assoc*, 1988, 4(4): 414-425.
Sakai et al., "Characterization of the physical properties of the stratum corneum by a new tactile sensor," *Skin Research and Technology*, Aug. 2000, pp. 128-134.
Schaefer, "Silicone Surfactants," *Tenside, Surfactants, Deterg.*, 1990, 27(3): 154-158.
Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.
Smith, "Hydroxy acids and skin again," *Soap Cosmetics Chemical Specialties*, 1993, pp. 54-59.
Solans et al. "Overview of basic aspects of microemulsions," Industrial Applications of Microemulsions, Solans et al Eds, New York, 1997, 66:1-17.
Squillante et al., "Codiffusion of propylene glycol and dimethyl isosorbide in hairless mouse skin," *European J. Pharm. Biopharm.*, 1998, 46(3):265-71.
Todd et al. "Volatile Silicone Fluids for Cosmetics," *91 Cosmetics and Toiletries*, 1976, 27-32.
Torma et al., "Biologic activities of retinoic acid and 3, 4-dehydroretinoic acid in human keratinoacytes are similar and correlate with receptor affinities and transactivation properties," *J. Invest. Dermatology*, 1994, 102: 49-54.
USP23/NF 18 The United States Pharmacopeia: The National Formulary, US Pharmacopoeia, 1995, p. 10-14.
Van Slyke, "On the measurement of buffer values and on the relationship of buffer value to the dissociation constant of the buffer and the concentration and reaction of the buffer solution," *J. Biol. Chem.*, 1922, 52:525-570.
Van Cutsem et al., "The antiinflammatory efects of ketoconazole," *J. AM. ACAD. Dermatol.*,1991, 25(2 pt 1):257-261.
Wang and Chen, "Preparation and surface active properties of biodegradable dextrin derivative surfactants," *Colloids and Surfaces A: Physicochemical and Engineering Aspects*, 2006, 281(1-3):190-193.
Weindl et al., "Hyaluronic acid in the treatment and prevention of skin diseases: molecular biological, pharmaceutical and clinical aspects," *Skin Pharmacology and Physiology*, 2004, 17: 207-213.
Xynos et al., "Effect of nifedipine on rectoanal motility," *Dis Colon Rectum*, 1996, 39(2):212-216.
Yamada et al., "Candesartan, an angiotensin II receptor antagonist, suppresses pancreatic inflammation and fibrosis in rats," *J. Pharmacol. Exp. Ther.*, 2003, 307(1)17-23.
Paragraph E.3.1 of regulation (EC) No. 2003 (See Directive 67/548/ EEC OJ 196, 16.8, 1967, p. 1.
Tzen et al., Lipids, proteins and structure of seed oil bodies from diverse species; *Plant Physiol.*, 1993, 101:267-276.

(56) References Cited

OTHER PUBLICATIONS

Brown et al. "Structural dependence of flavonoid interactions with Cu2+ inos: implications for their antioxidant properties," *Biochem. J.*, 1998, 330:1173-1178.
Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.
"Mineral oil USP," Chemical Abstracts Service Registry No. 8012-95-1, 2011, 7 pages.
"Tea tree oil," Chemical Abstract No. 68647-73-4, 2012, 2 pages.
Lin et al., "Ferulic acid stabilizes a solution of vitamins c and e and doubles its photoprotection of skin," *J Invest Dermatol*, 2005, 125:826-32.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.
Communication of a Notice of Opposition in European Application No. 03772600.7, dated Jan. 13, 2015, 36 pages.
Cremophor A Grades, BASF The Chemical Company, Jan. 2008, 6 pages.
Ellis et al., "The Treatment of Psoriasis with Liquor Carbonis Detergens," J. Invest Dermatology, 1948, 10:455-459.
Gels, Unc, The Pharmaceutics and Compounding Laboratory, retrieved on Aug. 25, 2014, http://pharmlabs.unc.edu/labs/gels/agents/htm, 4 pages.
Griffin, "Calculation of HLB Values of Non-Ionic Surfactants," Journal of the Society of Cosmetic Chemists, May 14, 1954, 249-256.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Le Vine et al., "Components of the Goeckerman Regimen," Journal of Investigative Dermatology, 1979, 73:170-173.
Luviquat Polymer Grades, BASF The Chemical Company, May 2012, 32 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Material Safety Data Sheet, Luvitol EHO, Caelo, Nov. 28, 2013, 4 pages.
Oh et al., "Antimicrobial activity of ethanol, glycerol monolaurate or lactic acid against Listeria moncylogenes," Int. J. Food Microbiology, 1993, 20:239-246.
Omega-9 Fatty Acids (Oleic Acid), Orthomolecular.org, Dec. 2004, retrieved on Aug. 15, 2014, http://orthomolecular.org/nutrients/omega9.html. 1 page.
Polystyrene, Wikipedia the free encyclopedia, retrieved Apr. 21, 2014, http://web.archive.org/web/20060312210423/http://en.wikipedia.org/wiki/Polystyrene, 4 pages.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Rohstoffinformationen, Hoffmann Mineral, 2008, 8 pages (with English translation).
Thorgeirsdottir et al., "Antimicrobial activity of monocaprin: a monoglyceride with potential use as a denture disinfectant," Acta Odontologica Scandinavica, Feb. 2006, 64:21-26 (Abstract only).
Vera et al., "Scattering optics of Foam," Applied Optics, Aug. 20, 2001, 40(24):4210-4214.
Ziolkowsky, "Moderne Aerosolschaume in der Kosmetik (Modern Aerosol Foams in Chemical and Marketing Aspects),", Seifen-Ole-Fette-Wachse, Aug. 1986, 112(13): 427-429 (with English translation).
"Alcohol," Wikipedia, the free encyclopeida, retrieved on May 17, 2014, http://en.wikipedia.org/wiki/Alcohol, 17 pages.
"Arquad HTL8-MS," AkzoNobel Functional Applications, retrieved on Mar. 18, 2013, Retrieved from the Internet: <URL: http://sc.akzonobel.com/en/fa/Pages/product-detail.aspx?prodID=8764>, 1 page.

"Can tuberous sclerosis be prevented?," Sharecare, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.
"Crohn's Disease," *Merck Manual Home Edition*, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
"Dacarbazine," Chemical Book, 2010, retrieved on Oct. 18, 2013, <URL: http://www.chemicalbook.com/ChemicalProductProperty_EN_CB7710656.htm>, 2 pages.
"Drug Index (Professional)—Dacarbazine," *BC Cancer Agency*, Jun. 2004, retrieved on Oct. 18, 2013, <URL:http://www.bccancer.bc.ca/HPI/DrugDatabase/DrugIndexPro/Dacarbazine.htm>, 6 pages.
"Fully refined paraffin waxes (FRP Wax)," *Industrial Raw Materials LLC*, Feb. 21, 2008, retrieved on Aug. 22, 2013, <http://irmwax.com/Wax/Paraffin/fully_refined.asp> 1 page.
"Gas Gangrene," Merck Manual Home Edition, 2008, retrieved on Jan. 16, 2013, <http://www.merckmanuals.com/home/infections/bacterial_infections/gas_gangrene.html?qt=gas gangrene&alt=sh>1 page.
"Human Immunodeficiency Virus Infection," Merck Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh >, 11 pages.
"Minocycline (DB01017)," DrugBank, Feb. 8, 2013, retrieved on Aug. 15, 2013, <http://www.drugbank.ca/drugs/DB01017>, 10 pages.
"New Nanomaterials to deliver anticancer drugs to cells developed," *Science Daily*, Jun. 2007, retrieved on Oct. 14, 2013, <URL: http://www.sciencedaily.com/releases/2007/06/070607112931.htm>, 3 pages.
"Product Data Sheet for Meclocycline," *bioaustralis fine chemicals*, Jun. 28, 2013, 1 page.
"Shear," *Vocabulary.com*, retrieved on Aug. 23, 2013, <URL: https://www.vocabulary.com/dictionary/shear>, 3 pages.
"Sheer," *Vocabulary.com*, retrieved on Aug. 23, 2013, <URL: https://www.vocabulary.com/dictionary/sheer>, 3 pages.
"View of NCT01171326 on Dec. 7, 2010," *ClinicalTrials.gov archive*, Dec. 7, 2010, retrieved on Sep. 9, 2013, <http://clinicaltrials.gov/archive/NCT01171326/2010_12_07>, 4 pages.
"View of NCT01362010 on Jun. 9, 2011," *ClinicalTrials.gov archive*, Jun. 9, 2011, retrieved on Sep. 9, 2013, <http://clinicaltrials.gov/archive/NCT01362010/2011_06_09>, 3 pages.
"What is TSC?," *Tuberous Sclerosis Alliance*, Jan. 1, 2005, retrieved on Feb. 6, 2014, <URL: http://www.tsalliance.org.pages.aspx?content=2>, 3 pages.
Abrams et al., "Ciclopirox gel treatment of scalp seborrheic dermatitis," Hydroxy-Piridones as Antifungal Agents with Special Emphasis on Onychomycosis, 1999, Chapter 8, 45-50.
Blaney and Cook, "Topical use of tetracycline in the treatment of acne," *Arch Dermatol*, Jul. 1976, 112:971-973.
Cetearyl Alcohol, Natural Wellbeing, Copyright 2001-2012, retrieved on Apr. 10, 2014, http://www.naturalwellbeing.com/learning-center/Cetearyl_Alcohol, 3 pages.
Cole and Gazewood, "Diagnosis and Treatment of Impetigo," Am Fam Physician, Mar. 15, 2007, 75(6):859-864.
Cunha, "Minocycline versus Doxycycline in the treatment of Lyme Neuroborreliosis," Clin. Infect. Diseases, 2000, 30: 237-238.
Durian et al., "Scaling behavior in shaving cream," The American Physical Society, Dec. 1991, 44(12):R7902-7905.
Google search strategy for minocycline solubility, retrieved on Aug. 15, 2013, <http://www.googl.com/search?rls=com.microsoft%3Aen-us%3AIE-SearchBox&q-melocycline+solubility>, 1 page.
Harry, "Skin Penetration," The British Journal of Dermatology and Syphillis, 1941, 53:65-82.
Lee et al., "Historical review of melanoma treatment and outcomes," Clinics in Dermatology, 2013, 31: 141-147.
Livingstone and Hubel, "Segregation of form, color, movement, and depth: Anatomy, physiology, and perception," Science, May 1988, 240:740-749.
*Molins PLC v. Textron Inc.*, 48 F.3d 1172, 33 USPQ2d 1823 (Fed. Cir. 1995), 19 pages.

(56) References Cited

OTHER PUBLICATIONS

Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.

Neves et al., "Rheological Properties of Vaginal Hydrophilic Polymer Gels," Current Drug Delivery, 2009, 6:83-92.

Oranje et al., "Topical retapamulin ointment, 1%, versus sodium fusidate ointment, 2%, for impetigo: a randomized, observer-blinded, noninferiority study," Dermatology, 2007, 215(4):331-340.

Prud'homme et al., Foams: theory, measurements and applications, Marcel Dekker, Inc., 1996, 327-328.

Purdy et al., "Transfusion-transmitted malaria: unpreventable by current donor exclusion guidelines?" Transfusion, Mar. 2004, 44:464.

Reregistration Eligibility Decision for Pyrethrins, EPA, Jun. 7, 2006, 108 pages.

Schmolka, "A review of block polymer surfactants," *Journal of the American Oil Chemists Society*, Mar. 1977, 54: 110-116.

Schott, "Rheology," *Remington's Pharmaceutical Sciences*, 17th Edition, 1985, 330-345.

Sciarra, "Aerosol Technology," Kirk-Othmer Encyclopedia of Chemical Technology, Jul. 2012, 20 pages.

Scully et al., "Cancers of the oral mucosa treatment and management," *Medscape Drugs, Diseases and Procedures*, Apr. 20, 2012, retrieved on Oct. 12, 2013, <http://emedicine.medscape.com/article/1075729-treatment>, 10 pages.

Sehgal, "Ciclopirox: A new topical pyrodonium antimycotic agent: A double-blind study in superficial dermatomycoses," British Journal of Dermatology, 1976, 95:83-88.

Softemul-165: Product Data Sheet, Mohini Organics PVT LTD, retrieved Apr. 10, 2014, http://www.mohiniorganics.com/Softemu1165.html#, 1 page.

*Sun Pharmaceutical Industried Ltd. v. Eli Lilly and Co.*, 611 F.3d 1381, 95 USPQ2d 1797 (Fed. Cir. 2010),7 pages.

Tavss et al., "*Anionic detergent-induced skin irritation and anionic detergent-induced pH rise of bovine serum albumin,*" J. Soc. Cosmet. Chem., Jul./Aug. 1988, 39:267-272.

Tirmula et al., "*Abstract: D28.00011: Enhanced order in thinfilms of Pluronic (A-B-A) and Brij (A-B) Block copolymers blended with poly (acrylic acid),*" Session D28: Block Copolymer Thin Films, Mar. 13, 2006, 1 page, Abstract.

Al-Mughrabi et al., "Effectiveness of Essential Oils and Their Combinations with Aluminum Starch Octenylsuccinate on Potato Storage Pathogens," TEOP, 2013, 16(1):23-31.

Beauty Banter, "Interesting list of comedogenic ingredients!!!!!!!!!!!" QVC blog, Interesting list of comedogenic ingredients, 2014, 1-14.

Chemical Characteristics, The Olive Oil Source, © 1998-2015, retrieved on Jun. 12, 2015, http://www.oliveoilsource.com/page/chemical-characteristics, 10 pages.

Codex Standard for Olive Oils and Olive Pomace Oils Codex Stan 33-1981, Adopted in 1981, recently amended 2013, 8 pages.

Devos and Miller, "Antisense Oligonucleotides: Treating neurodegeneration at the Level of RNA," Neurotherapeutics, 2013, 10:486-497.

Haw, "The HLB System: A Time Saving Guide to Surfactant Selection," Presentation to the Midwest Chapter of the Society of Cosmetic Chemists, Mar. 9, 2004, 39 pages.

Mailer, "Chemistry and quality of olive oil," NSW Dept. of Primary Industries, Aug. 2006, Primefact 227, 1-4.

Permethrin (Insecticide), Wildpro, retrieved on Jun. 4, 2015, http://wildpro.twycrosszoo.org/S/00Chem/ChComplex/perm.htm, 5 pages.

United States Standards for Grades of Olive Oil and Olive-Pomace Oil, United States Dept. of Agriculture, Oct. 25, 2010, 21 pages.

WebMD, "Psoriasis Health Center," 2014, retrieved Apr. 13, 2015, http://www.webmd.com/skin-problems-and-treatments/psoriasis/psoriasis-symptoms, 3 pages.

WebMD, "Understanding Rosacea—the Basics," 2014, retrieved Apr. 13, 2015, http://www.webmd.com/skin-problems-and-treatments/understanding-rosacea-basics, 5 pages.

Williams et al., "Acne vulgaris," Lancet, 2012, 379:361-372.

Allantoin, Römpp Online, retrieved on Sep. 23, 2015, https://roempp.thieme.de/roempp4.0/do/data/RD-O 1-01552, 5 pages.

Coconut Oil, Wikipedia, the free encyclopedia, retrieved on Jul. 3, 2015, https://en.wikipedia.org/wiki/Coconut_oil, 8 pages.

Communication of a Notice of Opposition in European Application No. 03772600.7, dated Sep. 23, 2015, 42 pages.

Communication of a Notice of Opposition in European Application No. 03772600.7, dated Sep. 24, 2015, 30 pages.

Diethyltoluamid, Wikipedia, the free encyclopedia, retrieved on Sep. 11, 2015, https://de.wikipedia.org/wiki/Diethyltoluamid, 12 pages.

Dimethylphthalate, Wikipedia, the free encyclopedia, retrieved on Sep. 11, 2015, http://de.wikipedia.org/wiki/Dimethylphthalat, 8 pages.

Healy, "Gelled Emollient Systems for Controlled Fragrance Release and Enhanced Product Performance," Cosmetics and toiletries, 2002, 117(2): 47-54.

Lamisil, Lamisil.http://www.fda.gov/downloads/Drugs/DrugSafety/PostmarketDrugSafetyInformationforPatientsandProviders/ucm052213.pdf, Published: Apr. 2001.

Leunapon-F, Leuna-Tenside, Screenshot, retrieved on Sep. 18, 2015, http://www.leuna-tenside.de/2006_7_14_3143/2006_8_7 5750/2006_8_7 24l/cas-68439-49-6, 1 page.

Mead, "Electrostatic Mechanisms Underlie Neomycin Block of the Cardiac Ryanodine Receptor Channel (RyR2)," Biophysical Journal, 2004, (87): 3814-3825.

Rowe et al., "Glyceryl Monooleate," Handbook of Pharmaceutical Excipients, 2011, pp. 1-5, retrieved on Dec. 19, 2011, http://www.medicinescomplete.com/mc/excipients/current/1001938996.htm?q=glyceryl%20monooleate&t=search&ss=text&p=1# hit.

Rowe et al., "Octyldodecanol," Handbook of Pharmaceutical Excipients, 2011, pp. 1-4, retrieved on Dec. 19, 2011, URL:http://www.medicinescomplete.com/mc/excipients/current/1001942450.htm?q=octyldodecanol &t=search&ss=text&p=1# hit.

Rowe et al., "Sucrose Palmitate," Handbook of Pharmaceutical Excipients, 2011, pp. 1-5, retrieved on Dec. 19, 2011, URL:http://www.medicinescomplete.com/mc/excipients/current/EXP-TD-c46-mn0001.htm?q=sucrose%20stearate&t=search&ss=text&p=1# hit.

Rowe et al., "Sucrose Stearate," Handbook of Pharmaceutical Excipients, 2011, pp. 1-4, retrieved on Dec. 19, 2011, URL:http://www.medicinescomplete.com/mc/excipients/current/EXP-TD-cll-mnOOO1-mnOOO1.htm?q=sucrose%20stearate&t=search&ss=text&p=3# hit.

RSES (Oil in Refrigerator Systems, Service Application Manual, 2009).

Security Datasheet, Luvitol EHO, Cetearyloctanoat, Nov. 27, 2013, 10 pages.

Sigma-Aldrich. http://www.sigmaaldrich.com/catalog/product/sial/p1754?lang=en® ion=. Published:Mar. 5, 2014.

Suppositories?, CareCure, http://sci.rutgers.edu/forum/showthread.php?4176-Suppositories. Published: Apr. 16, 2002.

Triethanolamine, haute.de, retrieved on Sep. 14, 2015, http://www.haut.de/service/inci/anzeige&id=16384&query=Triethanolamine &funktio . . . , 3 pages.

Valenta, "Effects of Penetration Enhancers on the In-vitro Percutaneous Absorption of Progesterone," J. Phann Pharrnacol., 1997, 49: 955-959.

Wenninger et al., "International Cosmetic Ingredient Dictionary and Handbook," The Cosmetic, Toiletry, and Fragrance Association, Washington, DC., 1997, vol. 1, 4 pages.

Williams et al., "Urea analogues in propylene glycol as penetration enhancers in human skin," International Journal of Pharmaceutics, 1989, 36, 43-50.

Wu et al., "Interaction of Fatty Acid Monolayers with Cobalt Nanoparticles," Nano Letters, 2004, 4(2): 383-386.

Everything but the Olive, (the Olive Oil Source 1998-2016). http://www.oliveoilsource.com/pageAchemical-characteristics).

Kaur et al., "Formulation Development of Self Nanoemulsifying Drug Delivery System (SNEDDS) of Celecoxib for Improvement of Oral Bioavailability," Pharmacophore, 2013, 4(4):120-133.

Sanders et al., "Stabilization of Aerosol Emulsions and Foams," J. Soc. Cosmet. Chem., 1970, 21:377-391.

(56) References Cited

OTHER PUBLICATIONS

Albrecht et al., "Topical minocycline foam for moderate to severe acne vulgaris: Phase 2 randomized double-blind, vehicle-controlled study results," J. Am. Acad. Dermatol., 2016, 74(6):1251-1252.
Chapter 1 Meaning of HLB Advantages and Limitations 1980; 4 pages.
Foamix Pharmaceuticals Statement: Use of Luviquat FC 370, Approved by Yohan Hazot, May 3, 2016, 3 pages.
Material Safety Data Sheet, Squalane, TCI America, 5 pages, https://www.spectrumchemical.com/MSDS/TCI-H0096.11f. Published: Oct. 6, 2014.
Reply of the Patent Proprietor to the Notices of Opposition in European Application No. 03772600.7, dated May 9, 2016, 134 pages.
Sorbitan Esters, [online] retrieved on Jul. 1, 2016 from: http://www.drugfuture.com/chemdata/sorbitan-esters.html 2 pages.
Sreenivasan et al., "Studies on Castor Oil. I. Fatty Acid Composition of Castor Oil," Journal of the American Oil Chemists Society. 1956, 33:61-66.
Summons to Attend Oral Proceedings in European Application No. 03772600.7, dated Jun. 30, 2016, 19 pages.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Australian Pharmaceutical Benefits Advisory Committee (PBAC), *PBAC Public Summary Document*—Nov. 2014 Meeting (5 pages).
European Patent Application No. 03772600.7 (U.S. Pat. No. 1,556,009): Minutes of Oral Proceedings, dated Feb. 3, 2017, 6 pages.
European Patent Application No. 03772600.7 (U.S. Pat. No. 1,556,009): Interlocutory Decision in Opposition Proceedings, dated Feb. 3, 2017, 54 pages.
Frankel, A.J. et al. (2010) "Coal Tar 2% Foam in Combination with a Superpotent Corticosteroid Foam for Plaque Psoriasis. Case Report and Clinical Implications" *J Clin Aesthet Dermatol*, 3(10):42-45.
Kircik, L.H. and S. Kumar (Aug. 2010) "Scalp Psoriasis" J Drugs Dermatol, 9(8 Suppl):s101-s137.
Penreco, "Intelligent Gel Technology Product Specifications," Rev. Jun. 2016 (2 pages).
PROMIUS™ Pharma LLC (2012) *Scytera™ (coal tar) Foam*, 2%. Product Information Sheet, 1 page.
Water Jel Technologies, "Material Safety Data Sheet for Neomycin Antibiotic Ointment," Dec. 1, 2004 (7 pages).
WebMD (2017) "User Reviews & Ratings—Scytera topical" [online]. Retrieved Mar. 1, 2017; retrieved from the Internet: http://www.webmd.com/drugs/drugreview-151502-Scytera+topical.aspx?drugid=151502&drugname=Scytera+topical&sortby=3 (2 pages).
Zeichner, J.A. (2010) "Use of Topical Coal Tar Foam for the Treatment of Psoriasis in Difficult-to-treat Areas" *J Clin Aesthet Dermatol*, 3(9):37-40.
Abdullah, G.Z. et al. (Jan. 2013) "Carbopol 934, 940 and Ultrez 10 as viscosity modifiers of palm olein esters based nano-scaled emulsion containing ibuprofen" *Pak J Pharm Sci*, 26(1):75-83.
Aslam et al. (2015) "Emerging drugs for the treatment of acne" *Expert Opin Emerging Drugs*, 20:91-101.
Beuchat (Feb. 1983) "Influence of Water Activity on Growth, Metabolic Activities and Survival of Yeasts and Molds" *J Food Prot*, 46(2):135-141.
Brisaert, M. et al. (1996) "Investigation on the chemical stability of erythromycin in solutions using an optimization system" *Pharm World Sci*, 18(5):182-186.
Canavan et al. (2016) "Optimizing Non-Antibiotic Treatments for Patients with Acne: A Review" *Dermatol Ther*, 6:555-578.
Craig, D.Q.M. et al. (Jul. 1994) "An investigation into the structure and properties of Carbopol 934 gels using dielectric spectroscopy and oscillatory rheometry" *J Controlled Rel*, 30(3):213-223 (Abstract).
Foamix Pharmaceuticals Ltd. (May 1, 2017) "Foamix Pharmaceuticals Announces Plans for Additional Phase 3 Trial for FMX101 in Moderate to Severe Acne," Press Release [online]. Retrieved from: http://www.foamix.co.il/news.asp?nodeID=564&itemID=204, on Jun. 12, 2017, 5 pages.
Fontana (Apr. 1999) "Pharmaceutical Applications for Water Activity" *Pharmaceutical Online* [online]. Retrieved from https://www.pharmaceuticalonline.com/doc/pharmaceutical-applications-for-water-activit- . . . , on Jan. 17, 2018 (4 pages).
Ghica, M.V. et al. (2011) "Design and optimization of some collagen-minocycline based hydrogels potentially applicable for the treatment of cutaneous wound infections" *Pharmazie*, 66:853-861.
Kanicky, J.R. and D.O. Shah (2002) "Effect of Degree, Type, and Position of Unsaturation on the $pK_a$ of Long-Chain Fatty Acids" *J Colloid and Interface Science*, 256:201-207.
Milton, D.T. et al. (2006) "A Phase I/II Study of Weekly High-Dose Erlotinib in Previously Treated Patients With Nonsmall Cell Lung Cancer" *Cancer*, 107:1034-1041.
Musial, W. and A. Kubis (2004) "Carbopols as factors buffering triethanolamine interacting with artificial skin sebum" *Polim Med*, 34(4):17-30 (Abstract).
Sarpotdar, P.P. et al. (Jan. 1986) "Effect of Polyethylene Glycol 400 on the Penetration of Drugs Through Human Cadaver Skin In Vitro" *J Pharma Sci*, 75(1):26-28.
Sigma Aldrich, "Surfactants Classified by HLB Numbers" 2017 [online]. Retrieved from the Internet: www.sigmaaldrich.com/materials-science/material-science-products.html?TablePage=22686648, on Jul. 8, 2017 (3 pages).
SOLODYN® (Minocycline HCl, USP) Prescribing Information; revised Jun. 2016, 2 pages.
Sung, J.H. et al. (2010) "Gel characterisation and in vivo evaluation of minocycline-loaded wound dressing with enhanced wound healing using polyvinyl alcohol and chitosan" *Intl J Pharmaceut*, 392:232-240.
Tamarkin, D. (2013) "Foam: A Unique Delivery Vehicle for Topically Applied Formulations" in: *Formulating Topical Applications—a Practical Guide*. Dayan N, Ed., Carol Stream, IL: CT Books, Chapter 9, pp. 233-260.
Tjulandin, S. et al. (2013) "Phase I, dose-finding study of AZD8931, an inhibitor of EGFR (erbB1), HER2 (erbB2) and HER3 (erbB3) signaling, in patients with advanced solid tumors" *Invest New Drugs*, 32(1):145-153.
Wrightson, W.R. et al. (1998) "Analysis of minocycline by high-performance liquid chromatography in tissue and serum" *J Chromatography B*, 706:358-361.
Kolb, "Emulsifiers, emollients and solubilizers for personal care", pp. 1-9, accessed Jun. 20, 2018.

\* cited by examiner

COMPOSITIONS, GELS AND FOAMS WITH RHEOLOGY MODULATORS AND USES THEREOF

CROSS REFERENCE TO RELATED APPLICATIONS

This application is a continuation application of U.S. application Ser. No. 13/100,724, filed May 4, 2011.

U.S. application Ser. No. 13/100,724, filed May 4, 2011, is a continuation-in-part application of International Application No. PCT/IB2010/002612, filed Oct. 1, 2010, and entitled "Surfactant-Free Water-Free Foamable Compositions, Breakable Foams and Gels, and Their Uses," which claims the benefit of priority to U.S. Provisional Application No. 61/248,144, filed Oct. 2, 2009, and entitled "Surfactant-Free Water-Free Foamable Compositions, Breakable Foams and Their Uses;" U.S. Provisional Application No. 61/322,148, filed Apr. 8, 2010, and entitled "Surfactant-Free Water-Free Foamable Compositions, Breakable Foams and Their Uses;" U.S. Provisional Application No. 61/349,911, filed May 31, 2010, and entitled "Surfactant-Free Water-Free Foamable Compositions, Breakable Foams and Their Uses;" U.S. Provisional Application No. 61/385,385, filed Sep. 22, 2010, and entitled "Surfactant-Free Water-Free Foamable Compositions, Breakable Foams and Gels and Their Uses;" U.S. Provisional Application No. 61/331,126, filed May 4, 2010, and entitled "Compositions, Gels and Foams with Rheology Modulators and Uses Thereof;" U.S. Provisional Application No. 61/388,884, filed Oct. 1, 2010, and entitled "Compositions, Gels and Foams With Rheology Modulators and Uses Thereof"; and U.S. Provisional Application No. 61/380,568, filed Sep. 7, 2010, and entitled "Surfactant-Free Water-Free Foamable Compositions and Breakable Foams and Their Uses; all of which are herein incorporated in their entirety by reference.

U.S. application Ser. No. 13/100,724, filed May 4, 2011, is a continuation-in-part application of International Application No. PCT/IB2010/002617, filed Oct. 1, 2010, and entitled "Topical Tetracycline Compositions" which claims the benefit of priority to U.S. Provisional Application No. 61/248,144, filed Oct. 2, 2009, and entitled "Surfactant-Free Water-Free Foamable Compositions, Breakable Foams and Their Uses;" United States Provisional Application No. 61/322,148, filed Apr. 8, 2010, and entitled "Surfactant-Free Water-Free Foamable Compositions, Breakable Foams and Their Uses;" U.S. Provisional Application No. 61/349,911, filed May 31, 2010, and entitled "Surfactant-Free Water-Free Foamable Compositions, Breakable Foams and Their Uses;" U.S. Provisional Application No. 61/385,385, filed Sep. 22, 2010, and entitled "Surfactant-Free Water-Free Foamable Compositions, Breakable Foams and Gels and Their Uses;" U.S. Provisional Application No. 61/331,126, filed May 4, 2010, and entitled "Compositions, Gels and Foams with Rheology Modulators and Uses Thereof;" U.S. Provisional Application No. 61/388,884, filed Oct. 1, 2010, and entitled "Compositions, Gels and Foams With Rheology Modulators and Uses Thereof"; and U.S. Provisional Application No. 61/380,568, filed Sep. 7, 2010, and entitled "Surfactant-Free Water-Free Foamable Compositions and Breakable Foams and Their Uses; all of which are herein incorporated in their entirety by reference.

U.S. application Ser. No. 13/100,724, filed May 4, 2011, is a continuation-in-part application of International Application No. PCT/IB2010/002613, filed Oct. 1, 2010, and entitled "Surfactant-Free Water-Free Foamable Compositions, Breakable Foams and Their Uses" which claims the benefit of priority to U.S. Provisional Application No. 61/248,144, filed Oct. 2, 2009, and entitled "Surfactant-Free Water-Free Foamable Compositions, Breakable Foams and Their Uses; U.S. Provisional Application No. 61/322,148, filed Apr. 8, 2010, and entitled "Surfactant-Free Water-Free Foamable Compositions, Breakable Foams and Their Uses; U.S. Provisional Application No. 61/349,911, filed May 31, 2010, and entitled "Surfactant-Free Water-Free Foamable Compositions, Breakable Foams and Their Uses; U.S. Provisional Application No. 61/385,385, filed Sep. 22, 2010, and entitled "Surfactant-Free Water-Free Foamable Compositions, Breakable Foams and Gels and Their Uses; U.S. Provisional Application No. 61/331,126, filed May 4, 2010, and entitled "Compositions, Gels and Foams with Rheology Modulators and Uses Thereof; U.S. Provisional Application No. 61/388,884, filed Oct. 1, 2010, and entitled "Compositions, Gels and Foams With Rheology Modulators and Uses Thereof"; and U.S. Provisional Application No. 61/380,568, filed Sep. 7, 2010, and entitled "Surfactant-Free Water-Free Foamable Compositions and Breakable Foams and Their Uses; all of which are herein incorporated in their entirety by reference.

BACKGROUND

The term rheology, describes the flow dynamics of liquids and the deformation of solids. Rheological properties of heterogeneous dispersions are complex and cannot be expressed in a single parameter. Manufacturers of medicinal and cosmetic gels, creams, pastes, lotions and foams must be capable of producing products with acceptable consistency and smoothness and reproducing these qualities each time a new batch is prepared including its look, feel, body, and consistency.

Rheology is involved in the mixing and flow of materials, their packaging into containers, and their dispensing prior to use, whether this is achieved by pouring from a bottle, extrusion from a tube, passage through a syringe needle, or extrusion through a valve. The rheology of a particular product, which can range in consistency from fluid to semisolid to solid, can affect its patient acceptability, physical stability, and even biologic availability. For example, viscosity which is a rheological property has been shown to affect absorption rates of drugs.

Pharmaceutical areas, in which rheology is significant include product design and processing are fluids, quasi-solids, solids, and processing. Rheology of fluids is pertinent in respect of: (a) mixing fluids; (b) reduction of systems with shear; (c) passage through orifices, including pouring, packaging in bottles, passage through hypodermic needles and passage through valves; (d) fluid transfer, including pumping and flow through pipes; and (e) physical stability of disperse systems. Rheology of quasi-solids or semi-solids is pertinent including in respect of: (a) spreading and adherence on the skin; (b) removal from jars or extrusion from tubes; (c) capacity of solids to mix with miscible liquids; and (d) release of the drug from the base.

When classifying materials according to types of flow and deformation, it is customary to place them in one of two categories: Newtonian or non-Newtonian systems. The choice depends on whether or not their flow properties are in accord with Newton's law of flow. Newton recognized that the higher the viscosity of a liquid, the greater is the force per unit area (shearing stress) required to produce a certain rate of shear. Many fluid pharmaceutical products behave as Non-Newtonian systems.

Rheological properties such as tackiness or stickiness, "body," "slip," and "spreadability" are difficult to measure by means of conventional apparatus and, in fact, do not have precise meanings. Whereas, viscosity, yield value, thixotropy, and the other properties that contribute to the total consistency of non-Newtonian pharmaceuticals can be analyzed.

Viscosity is a measure of the internal resistance of a fluid to flow which is being deformed by either shear stress or tensile stress; the higher the viscosity, the greater is the resistance. Simple liquids can be described in terms of absolute viscosity. In everyday terms (and for fluids only), viscosity is "thickness" and may be thought of as an indication of fluid friction. Shear viscosity, describes the reaction to applied shear stress; in other words, it is the ratio between the pressure exerted on the surface of a fluid, in the lateral or horizontal direction, to velocity gradient.

Gels are jelly-like material that can have properties ranging from soft and fluid to hard and tough. Gels may be in liquid, semi-liquid or solid state. Solid gels are defined as a substantially diluted crosslinked system, which exhibits no flow when in the steady-state. By weight, gels are mostly liquid, yet they behave like semi-solids due to a three-dimensional crosslinked network of a solidifying, gelling or thickening agent within the liquid. It is the crosslinks within the fluid that give a gel its structure (hardness) and contribute to stickiness (tack). Depending on the amounts of gelling agents in a formulation the gel may be semi solid with some limited flowability, such that when the semi-solid gel is placed in a tube and is inclined horizontally from a vertical position it will slowly flow from the vertical towards the horizontal or it may be a liquid gel where the amount of gelling agents or gelling effect is lower such that the gel structure or connections are weaker or loose so that when placed in a tube and tilted from a vertical position to the horizontal the gel readily flows and adapts to the horizontal position. The rheological properties of gels at different surface temperatures can influence the release and bioabsorption of drugs therefrom.

It is a desirable property for composition for topical use to have controllable viscosity. High viscosity is required to avoid drips and runs for ease of application and improve suspending properties in order to avoid rapid sedimentation of non-dissolved active ingredients. Whereas, low viscosity is desirable to enable spreadability and good flow properties. The less viscous something is, the greater its ease of movement (fluidity). A delicate balance between these two attributes is sought out in accordance with the intended use of the compositions. This balance is difficult to attain as viscosity of a composition is influenced by different factors such as reaction or interaction between different components under different temperature and pressure conditions.

Thickening or solidifying agent or solidifying complexes are materials added to a composition which increase viscosity and retard sedimentation. The use of waxes, fatty alcohols, fatty acids and 12 hydroxy stearic acid, in solidifying oils is known. Pharmaceutical compositions having a netted framework, comprising an oil and beeswax as a gelling agent that form a film after application on a body surface are also known. Netted frameworks and/or films can be in certain circumstances be a disadvantage.

The addition of a fatty alcohol, or a fatty acid, or both to a liquid oil also gives rise to thixotropic properties (e.g., being semi-solid at rest and liquid upon application of shear forces thereto). This property enables application of a thixotropic mixture as a semi-solid state to a body surface, which subsequently becomes substantially liquid and therefore more spreadable and penetrable when rubbed onto the body surface. Thus, they are semi-solid at rest and that they liquefy upon application of shear forces thereto. Semi-solid hydrophobic formulations are important not only for the pharmaceutical market but also for cosmetic products, such as carriers of sunscreen compounds, oil-soluble plant extracts, materials for scrubbing purposes and other active and non-active cosmetic ingredients.

Foams and, in particular, single-phase oleaginous foams are complicated systems which do not form under all circumstances. Slight shifts in foam composition, such as by the addition of active agents or the removal of any of the essential ingredients, may destabilize the foam. The prior art teaches that oleaginous foam compositions require significant amounts of surface active agents to form a foam. These compositions require various standard surfactants, as essential components.

Surfactants are known as essential ingredients in foam compositions; and specifically in oleaginous foams. However, many surfactants are known to be irritating when left on the skin can also react with unstable active agents and lead to their rapid degradation.

Gels and foams are not pharmaceutically equivalent, unless their composition upon administration is similar.

SUMMARY

The present application relates to compositions comprising a carrier and a first and second rheology modulator or modulator (used interchangeably). The application also relates to compositions or foamable compositions and foam without surfactants and/or without polymeric agents comprising an oleaginous carrier, a first rheology modulator which is a suspended pharmaceutical or cosmetic active agent (referred as "active agent") and second rheology modulator consisting of at least one fatty alcohol, at least one fatty acid, at least one wax and mixtures of two or more thereof. Solid fatty alcohols and/or fatty acids and/or waxes were carefully selected through experimentation as suitable thickening agents, which can be compatible with unstable active agents.

It was surprisingly discovered that the addition of a very low concentration of a suspended active agent into a composition or formulation comprising a hydrophobic solvent, together with a second rheology modulator, which may be at least one fatty alcohol or at least one fatty acid, and/or at least one wax and mixtures of two or more thereof dramatically modulates the rheological properties of the composition and in particular can synergistically increase the viscosity of a composition, thereby providing improved usability of the composition.

It was further surprisingly discovered in the present invention, that certain compositions comprising a hydrophobic solvent, together with a second rheology modulator, which may be at least one fatty alcohol or at least one fatty acid, and/or at least one wax and mixtures of two or more thereof; and a suspended active agent without any surface active agents resulted, upon packaging in an aerosol container and adding a propellant, in a shakable and homogenous foamable composition, which released a breakable foam with good to excellent quality (as defined herein).

The resulting foam is pharmaceutically equivalent to the respective gel (prior to adding the propellant), since immediately upon dispensing of the foam the propellant evaporates and the composition upon administration is similar to that of the gel. This is an important pragmatic advantage, because many drug development activities, including expensive and lengthy clinical trials on thousands of patients, can be saved by conducting such studies once for both the gel and foam instead of twice.

In one or more embodiments there is provided a composition for cosmetic or pharmaceutical application comprising:
  a) a first rheology modulator comprising a suspended pharmaceutical active agent or a suspended cosmetic active agent;
  b) a second rheology modulator comprising at least one fatty alcohol, at least one fatty acid, at least one wax and mixtures thereof; and
  c) a hydrophobic carrier comprising at least one hydrophobic solvent;
  wherein the viscosity of the composition is at least about 30% higher than the viscosity of a first partial composition comprising the second rheology modulator agent and the hydrophobic carrier without the first rheology modulator; and is higher than the viscosity of a second partial composition comprising the first rheology modulator and the hydrophobic carrier without the second rheology modulator; and In certain embodiments, the viscosity of the first partial composition is less than about 25,000 cPs at room temperature.

According to an another embodiment the composition further comprises about 1% to about 25% by weight of a polar solvent or a penetration enhancer.

In one or more embodiments the first rheology modulator comprises at least one tetracycline. In one or more embodiments the tetracycline is compatible with the carrier and with the second rheology modulator.

In one or more embodiments the amount of first rheology modulator is a therapeutically effective amount. In one or more embodiments the first rheology modulator is a suspended active agent.

In one or more embodiments the active agent is a tetracycline. In one or more embodiments the tetracycline is tetracycline, oxytetracycline, demeclocycline, doxycycline, lymecycline, meclocycline, methacycline, minocycline, rolitetracycline, chlorotetracycline or tigecycline. In one or more embodiments the tetracycline is tetracycline, minocycline or doxycycline or a salt thereof. In one or more embodiments the tetracycline is a mixture of two or more tetracyclines. In one or more embodiments the tetracycline is a hydrophobic tetracycline, selected from minocycline and doxycycline. In one or more embodiments it is a mixture of both. In one or more embodiments the tetracycline is present in a free base form, a hydrate form, a salt form or a complex form. In one or more embodiments at least part of the tetracycline is not soluble and is suspended in the composition. A tetracycline that is suitable as a first rheology modulator according to the present invention is one that is not soluble or is partially soluble and all or part thereof is suspended in the composition.

In one or more embodiments the better rheology includes one or more of a reduction in composition flow, an increase in composition viscosity, an increase in hardness, or an increase in adhesion, and/or thixotropy, or any two or more thereof.

Viscosity is raised significantly when a formulation comprising beeswax in combination with another wax or a fatty acid or fatty alcohol in a hydrophobic carrier is challenged with a first rheology active agent (minocycline).

In one or more embodiments there is provided a composition wherein the viscosity of the composition changes with time whilst the composition is flowing. In certain embodiments the change is an increase. In certain other embodiments the change is a decrease. In some embodiments the composition is not flowing.

In one or more embodiments upon addition of the first rheology modulator to a composition comprising a second rheology modulator the composition becomes more viscous. An example is where a tetracycline antibiotic is added to a fatty alcohol in an oil carrier [see Examples 4 and 5].

In one or more embodiments there is provided a composition in which the first and second rheology modulators act synergistically. In one or more embodiments the first and second modulators act synergistically to increase the viscosity of the composition.

In one or more embodiments there is provided a composition in which the viscosity of the composition after addition of the first rheology modulator and second rheology modulator to the carrier is higher than the viscosity of the composition with the second modulator agent to the carrier, without the first modulator; and is higher than the viscosity of the composition with the first modulator to the carrier without the second modulator.

In an embodiment or more embodiments there is provided a composition as a vehicle or carrier wherein by adding an active agent to a composition comprising a second rheology modulator one or more rheological properties of the composition are modulated such as the viscosity of the composition is changed (e.g., increased substantially).

In one or more embodiments, there is provided an oleaginous formulation comprising a hydrophobic solvent, such as mineral oil(s) and at least one suspended active agent which is a tetracycline in synergistic combination with a second rheology modulator comprising a fatty alcohol and/or a fatty acid and/or a wax.

A composition comprising the second rheology modulator and the hydrophobic carrier without the first rheology modulator is designated a first partial composition and a composition comprising the first rheology modulator and the hydrophobic carrier without the second rheology modulator is designated a second partial composition. In one or more embodiments the viscosity of the composition is at least about 50% more than the viscosity of the first partial composition without the first rheology modulator. In one or more embodiments the increase in viscosity of the composition is at least about 100% more than the viscosity of the first partial composition without the first rheology modulator. In one or more embodiments the increase in viscosity of the composition is at least about 100% and viscosity of the first partial composition without the first rheology modulator is less than about 12,000 cPs; or less than about 8,000 cPs; or less than about 2,000 cPs. In one or more embodiments the viscosity of the first partial composition without the first rheology modulator is more than about 1,000 cPs; or more than about 1,300 cPs; or more than about 1,500 cPs. or more than about 1,800 cPs or more than about 2000 cPs.

In certain embodiments the increase in viscosity is a synergistic increase such that the combined viscosity of the first partial composition and the viscosity of the second partial composition is less than the viscosity of the composition.

In one or more embodiments the change in viscosity is at least about 20% or more than 20%. In one or more embodiments the change in viscosity is at least about 30% or more than 30%. In one or more embodiments the change in viscosity is at least about 40% or more than 40%. In one or more embodiments the change in viscosity is at least about 50% or more than 50%. In one or more embodiments the change in viscosity is at least about 100% or more than 100%. In one or more embodiments the change in viscosity is at least about 150% or more than 150%. In one or more embodiments the change in viscosity is at least about 200% or more than 200%. In one or more embodiments the change in viscosity is at least about 250% or more than 250%. In one or more embodiments the change in viscosity is at least about 300% or more than 300%. In one or more embodiments the change in viscosity is at least about 350% or more than 350%. In one or more embodiments the change in viscosity is at least about 400% or more than 400%. In one or more embodiments the change in viscosity is at least 450% or at least more than 450%. In one or more embodiments the change in viscosity is at least about 500% or more than 500%. In one or more embodiments the change in viscosity is at least about 1000% or more than 1000%. In one or more embodiments the change in viscosity is at least about 1500% or more than 1500%. %. In one or more embodiments the change in viscosity is at least about 2000% or more than 2000%. In one or more embodiments the change in viscosity is at least about 2500% or more than 2500%. In one or more embodiments the change in viscosity is at least about 20% or more than 20%. In one or more embodiments the change in viscosity is at least about 30% or more than 30%. In one or more embodiments the change in viscosity is at least about 40% or more than 40%. In one or more embodiments the change in viscosity is between about 50% and about 100%. In one or more embodiments the change in viscosity is between about 100% and about 500%. In one or more embodiments the change in viscosity is between about 500% and about 1000%. In one or more embodiments the change in viscosity is between about 1000% and about 1500%. In one or more embodiments the change in viscosity is between about 1500% and about 2000%. In one or more embodiments the change in viscosity is between about 2000% and about 2500%. In one or more embodiments the change in viscosity is between about 50% and about 3000%. In one or more embodiments the change in viscosity is in a range between about 150% and about 1000%. In one or more embodiments the change in viscosity is in a range between about 1000% and about 2500% In one or more embodiments the change in viscosity is between about 100% and about 2500%; about 100% and about 2000%; about 100% and about 1500%; or about 100% and about 1000%.

In one or more embodiments the viscosity of the carrier and the composition prior to the addition of the first rheology modulator (namely the first partial composition) is less than about 30,000 cPs. In one or more embodiments the viscosity of the carrier and the composition prior to the addition of the first rheology modulator is less than about 25,000 cPs. In one or more embodiments the viscosity of the carrier and the composition prior to the addition of the first rheology modulator is less than about 20,000 cPs. In one or more embodiments the viscosity of the carrier and the composition prior to the addition of the first rheology modulator is less than about 15,000 cPs. In one or more embodiments the viscosity of the carrier and the composition prior to the addition of the first rheology modulator is less than about 12,000 cPs. In one or more embodiments the viscosity of the carrier is less than about 10,000 cPs. In one or more embodiments the viscosity of the carrier and the composition prior to the addition of the first rheology modulator is less than about 8,000 cPs. In one or more embodiments the viscosity of the carrier and the composition prior to the addition of the first rheology modulator is less than about 6,000 cPs. In one or more embodiments the viscosity of the carrier and the composition prior to the addition of the first rheology modulator is less than about 5,000 cPs. In one or more embodiments the viscosity of the carrier and the composition prior to the addition of the first rheology modulator is less than about 4,000 cPs. In one or more embodiments the viscosity of the carrier and the composition prior to the addition of the first rheology modulator is less than about 3,000 cPs. In one or more embodiments the viscosity of the carrier and the composition prior to the addition of the first rheology modulator is less than about 2,000 cPs. In one or more embodiments the viscosity of the carrier and the composition prior to the addition of the first rheology modulator is less than about 1,000 cPs. In one or more embodiments the viscosity of the carrier and the composition prior to the addition of the first rheology modulator is less than about 500 cPs. In one or more embodiments the viscosity of the carrier and composition prior to the addition of the first rheology modulator is less than about 30,000 cPs; is less than about 25,000 cPs; is less than about 20,000 cPs; is less than about 15,000 cPs; is less than about 12,000 cPs; is less than about 10,000 cPs; is less than about 8,000 cPs; is less than about 6,000 cPs; is less than about 5,000 cPs; is less than about 4,000 cPs; is less than about 3,000 cPs; is less than about 2,000 cPs; is less than about 1,000 cPs; or is less than about 500 cPs. In one or more embodiments the viscosity of the carrier and the composition prior to the addition of the first rheology modulator is less than about 30,000 cPs; is less than about 25,000 cPs; is less than about 20,000 cPs; is less than about 15,000 cPs; is less than about 12,000 cPs; is less than about 10,000 cPs; is less than about 8,000 cPs; is less than about 6,000 cPs; is less than about 5,000 cPs; is less than about 4,000 cPs; is less than about 3,000 cPs; is less than about 2,000 cPs; is less than about 1,000 cPs; or is less than about 500 cPs. In one or more embodiments the viscosity range of the carrier or the composition prior to the addition of the first rheology modulator or the carrier and the composition prior to the addition of the first rheology modulator includes about 30,000 cPs to about 1,000 cPs; about 25,000 cPs to about 1,000 cPs; about 20,000 cPs to about 1,000 cPs; about 12,000 cPs to about 1,000 cPs; about 10,000 cPs to about 1,000 cPs; about 8,000 cPs to about 1,000 cPs; about 6,000 cPs to about 1,000 cPs; about 5,000 cPs to about 1,000 cPs; about 4,000 cPs to about 1,000 cPs; about 2,000 cPs to about 1,000 cPs; or about 2,000 cPs to about 500 cPs; about 25,000 cPs to about 500 cPs; about 20,000 cPs to about 500 cPs; about 12,000 cPs to about 500 cPs; about 10,000 cPs to about 500 cPs; about 8,000 cPs to about 500 cPs; about 6,000 cPs to about 500 cPs; about 6,000 cPs to about 150 cPs; about 4,000 cPs to about 150 cPs; about 2,000 cPs to about 150 cPs; or about 1,000 cPs to about 150 cPs;

In one or more embodiments there is provided a composition in which the active agent is in an amount that is capable of altering the viscosity of the composition to a level higher than the viscosity of the composition prior to the addition of the active agent and wherein the second rheology modulator is capable of altering the viscosity of the composition before, upon or following the addition of the first modulator.

In one or more embodiments the composition is substantially waterless.

In one or more embodiments the composition is a liquid or freely flowable. In one or more embodiments the composition is a semi solid. In one or more embodiments the composition is a thick gel.

In one or more embodiments the composition is essentially free of one or more of the following:
 a) Water;
 b) Polymeric agent;
 c) Surfactant;
 d) Short chain alcohol;
 e) Polyol;

In one or more embodiments the composition is essentially free of two or more of water; polymeric agent; surfactant; short chain alcohol; or polyol. In one or more embodiments the composition is essentially free of three or more of water; polymeric agent; surfactant; short chain alcohol; or polyol. In one or more embodiments the composition is essentially free of four or more of water; polymeric agent; surfactant; short chain alcohol; or polyol. In one or more embodiments the composition is essentially free of water; polymeric agents; surfactants; short chain alcohols; and polyols.

For example, in one or more embodiments the composition is essentially free of water, polymeric agents, surfactants, short chain alcohol and polyols. In one or more embodiments the composition is essentially free of polymeric agents, surfactants, short chain alcohol and polyols. In one or more embodiments the composition is essentially free of water, surfactants, short chain alcohols and polyols. In one or more embodiments the composition is essentially free of water, polymeric agents, short chain alcohols and polyols. In one or more embodiments the composition is essentially free of water, polymeric agents, surfactants and polyols. In one or more embodiments the composition is essentially free of water, polymeric agents, surfactants and short chain alcohols.

In one or more embodiments there is provided a composition in which the composition has one two or three the following characteristics:
 a) Provides for chemical stability of the active agent in the composition;
 b) Provides for physical stability of the composition;
 c) Provides a therapeutic effect;

In one or more embodiments there is provided a composition in which the active agent is stable at room temperature for at least 1 month, or at least 2 months, or at least 3 months, or at least 4 months, or at least 5 months, or at least 6 months, or at least 12 months, or at least 18 months. In one or more embodiments there is provided a composition in which the active is stable at 40° C. for at least 1 month, or at least 2 months, or at least 3 months, or at least 4 months, or at least 5 months, or at least 6 months.

In one or more embodiments there is provided a composition in which the active agent forms a complex with one or more excipients.

In one or more embodiments there is provided a composition in which the active agent is chemically stable in the presence of the second rheology modulator and/or the carrier.

In one or more embodiments there is provided a composition in which the suspended active agent is selected from a list comprising a tetracycline, mometasone furoate, doxycycline hyclate, salicylic acid, diclofenac, urea, terbinafine, permethrin, metronidazole, pimecrolimus and benzoyl peroxide.

In one or more embodiments certain active agent, which are fully soluble in the composition including cholesterol and vitamin E also demonstrate a synergistic viscosity increase.

In one or more embodiments there is provided a composition in which the rheology modulator is selected from the group comprising a fatty alcohol, a fatty acid, beeswax, beeswax extract, a paraffin wax and hydrogenated castor oil and mixture thereof.

In one or more embodiments there is provided a composition in which the second rheology modulator comprises at least one fatty alcohol, or at least one fatty acid or least one wax or mixtures of two or more thereof.

In one or more embodiments there is provided a composition in which the second rheology modulator comprises a combination of (i) at least one fatty alcohol, (ii) at least one fatty acid; and (iii) at least one wax.

In one or more embodiments there is provided a composition in which the second rheology modulator comprises a compound, selected from the groups consisting of at least one fatty alcohol, at least one fatty acid, at least one wax and mixtures of two or more thereof. At least one fatty alcohol is selected from the group consisting of (a) a fatty alcohol having 14 or more carbons in their carbon chain, myristyl alcohol, cetyl alcohol, stearyl alcohol, erucyl alcohol, arachidyl alcohol, behenyl alcohol, tetracosanol, hexacosanol, octacosanol, triacontanol, tetratriacontanol, 1-triacontanol and a fatty alcohol, having a carbon chain between C30 and C50, (b) a fatty alcohol mixture, derived from beeswax, (c) a therapeutically-active fatty alcohol. At least one fatty acid is selected from the group consisting of a hydroxy fatty acid, a fatty acid having 12 or more carbons in its carbon chain, dodecanoic acid, myristic acid, hexadecanoic acid, heptadecanoic acid, stearic acid, arachidic acid, behenic acid, tetracosanoic acid, hexacosanoic acid, heptacosanoic acid, octacosanoic acid, triacontanoic acid, dotriacontanoic acid, tritriacontanoic acid, tetratriacontanoic acid and pentatriacontanoic acid and a fatty acid, having a carbon chain between C30 and C50. At least one wax is selected from the group consisting of: a wax, having the properties of (i) plastic behavior at ambient temperatures, (ii) a melting point above approximately 45° C., (iii) a relatively low viscosity when melted; and (iv) hydrophobic nature;

In one or more embodiments the composition further comprises a liquefied or compressed gas propellant wherein the composition is a foamable composition;
 wherein the second rheology modulator is about 0.1% to about 20% by weight of the composition; wherein the hydrophobic carrier is about 60% to about 95% by weight of the composition and wherein the ratio of composition other than propellant to propellant is from about 100:1 to about 100:30; and wherein upon dispensing the foamable carrier composition forms a breakable foam that breaks easily upon application of shear force. In an embodiment the formulation is short term stable.

In one or more embodiments, the formulation is a gel that is capable of forming a foamable composition when packaged into an aerosol canister, equipped with a valve and pressurized with a liquid or pressurized gas propellant and is capable of releasing a foam of quality that is breakable upon application of shear force but is not thermolabile at about or close to body temperature (about 36° C.).

In one or more embodiments, upon addition of between about 4% to about 8%; or about 8% to about 12% propellant, the formulations provide a foam of good or excellent quality that had a collapse time in excess of 3 minutes.

In an embodiment the wax is selected from the group consisting of vegetable wax, beeswax, chinese wax, cotton wax, bayberry wax, candelilla wax, carnauba wax, castor wax, cuban palm wax, esparto wax, fir wax, flax wax, flower wax, fat wax, japan wax, sandy wax, lanolin wax, ouricury wax, palm waxes, rice bran wax, rice-oil wax, shellac wax, soy wax, sugar cane wax, ucuhuba wax, a hydrogenated oil, hydrogenated castor oil, hydrogenated cottonseed oil, or hydrogenated jojoba oil, mink wax, montan wax, ozokerite, PEG-6 beeswax, rezo wax, spent grain wax, stearyl dimethicone, a paraffin wax, paraffin 58-62° C. wax, paraffin 51-53° C. wax, paraffin 42-44° C. wax, synthetic mineral wax, Fischer-tropsch wax, duroxon wax, or polymekon wax, synthetic waxes, albacer wax, atlasene wax, BASF waxes, cardis waxes, ceramid, glyco waxes, flexo wax, or oxazoline waxes, as well as other waxes, as described in "The Complete Technology Book on Wax and Polishes, Publisher: Asia Pacific Business Press Inc., 2006".

In one or more embodiments the wax is a mixture of two or more waxes. In certain embodiments the mixture of waxes comprises hydrogenated caster oil and beeswax.

In one or more embodiments the ratio of fatty alcohol to wax or fatty acid to wax or fatty alcohol and fatty acid to wax can be between about 1:10 to about 10:1. In one or more embodiments the ratio of fatty alcohol to wax or fatty acid to wax or fatty alcohol and fatty acid to wax can be between about 1:5 to about 5:1. In one or more embodiments the ratio of fatty alcohol to wax or fatty acid to wax or fatty alcohol and fatty acid to wax can be between about 1:3 to about 3:1. In one or more embodiments the ratio of fatty alcohol to wax or fatty acid to wax or fatty alcohol and fatty acid to wax can be between about 1:2 to about 2:1. In one or more embodiments the ratio of fatty alcohol to wax or fatty acid to wax or fatty alcohol and fatty acid to wax can be about 1:1.

In one or more embodiments there is provided a composition in which cholesterol has a rheology effect, wherein it acts as a viscosity booster.

In one or more embodiments there is provided a composition in which the concentration of the first rheology modulator in the composition is from about 0.01% to about 25% by weight.

The composition comprises at least one hydrophobic solvent

In one or more embodiments the hydrophobic solvent is selected from the group consisting of a diglyceride, a therapeutic oil, acetylated lanolin alcohol, alexandria laurel tree oil, alkyl benzoate, alkyl octanoate, almond oil, an essential oil, an unsaturated or polyunsaturated oil, apricot stone oil, arachidyl behenate, arachidyl propionate, avocado oil, barley oil, basil oil, beeswax, benzyl laurate, benzyl myristate, benzyl palmitate, bis (octyldodecyl stearoyl) dimer dilinoleate, borage seed oil, butyl myristate, butyl stearate, C12-C15 alkyl benzoate, C12-C15 alkyl octanoate, calendula oil, camphor oil, canelle nut tree oil, canola oil, capric/caprylic triglycerides, caprylic/capric triglyceride castor oil, caprylyl methicone, cardamom oil, carrot oil, castor oil, cetearyl ethylhexanoate, cetearyl isononanoate, cetearyl octanoate, cetyl acetate, cetyl dimethicone, cetyl ethylhexanoate, cetyl lactate, cetyl myristate, cetyl octanoate, cetyl palmitate, cetyl ricinoleate, citronella oil, clary sage oil, clove oil, cocoglycerides, coconut oil, cod-liver oil, corn oil, cotton oil, cottonseed oil, cyclohexasiloxane, cyclomethicone, Cyclomethicone 5-NF (cyclopentasiloxane), cyclotetrasiloxane, cypress oil, decyl oleate, diethyleneglycol diethylhexanoate, diethyleneglycol diisononanoate, diethyleneglycol dioctanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumerate, dimethicone, dimethyl polysiloxane, dioctyl malate, dioctyl sebacate, disopropyl adipate, dodecyl oleate, Dow Corning 244 Fluid (cyclotetrasiloxane), Dow coming 246 Fluid (d6+d5) (cyclohexasiloxane & cyclopentasiloxane), epoxy-modified silicone oil, essential oils, ester derivatives of lanolic acid, ester oils, ethylhexyl cocoate, ethylhexyl ethylhexanoate, ethylhexyl hydroxystarate, ethylhexyl isononanoate, ethylhexyl palmitate, ethylhexyl palmytate, ethylhexyl pelargonate, ethylhexyl stearate, evening primrose oil, fatty acid-modified silicone oil, flaxseed oil, fluoro group-modified silicone oil, frankincense oil, gelled mineral oil, ginger oil, glycereth triacetate, glycerol triheptanoate, glyceryl oleate, glyceryl trioctanoate, glyceryl triundecanoate, grape seed oil, grapefruit oil, groundnut oil, hard fat, hazelnut oil, heavy mineral oil, hempseed oil, herring oil, hexadecyl stearate, hexyl laurate, hydrocarbon oils, hydrogenated castor oil, hyssop oil, isoamyl laurate, isocetearyl octanoate, isocetyl isocetyl behenate, isocetyl lanolate, isocetyl palmitate, isocetyl salicylate, isocetyl stearate, isocetyl stearoyl stearate, isodecyl ethylhexanoate, isodecyl isononanoate, isodecyl oleate, isododecane, isohexadecane isododecane, isohexadecanol, isohexyl decanoate, isononyl isononanoate, isononyl octanoate, isoparaffin, isopropyl isostearate, isopropyl lanolate, isopropyl laurate, isopropyl myristate, isopropyl palmitate, isopropyl stearate, isosteary citrate, isosteary salicylate, isosteary tartarate, isostearyl behenate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isotridecyl isononanoate, jasmine oil, jojoba oil, lauryl lactate, lavender oil, lemon oil, light mineral oil, liquid paraffin, liquid triglycerides, lucerne oil, maize germ oil, maleated soybean oil, mandarin oil, manuka oil, marjoram oil, marrow oil, MCT oil, methylphenylpolysiloxane, millet oil, mineral oil, myristyl lactate, myristyl myristate, myristyl neopentanoate, myristyl propionate, myrrh oil, neopentylglycol dicaprate, neopentylglycol dicaprylate/dicaprate, neroli oil, nutmeg oil, octyl palmitate, octyl stearate, octyldodecanol, octyldodecyl behenate, octyldodecyl hydroxystearate, octyldodecyl myristate, octyldodecyl stearoyl stearate, oils from animal origin, oils of plant origin, oleyl erucate, oleyl lactate, oleyl oleate, olive oil, or dimethiconol, palm oil, passionflower oil, peanut oil, PEG/PPG 18/18 dimethicone, pentaerythrityl tetrastearate, petitgrain oil, petrolatum, phenyl trimethicone, phenyltrimethicone, poly(dimethylsiloxane)-(diphenyl-siloxane) copolymer, polyalkyl siloxane, polyalkylaryl siloxane, polyalphaolefin, polyaryl siloxane, polyaryl siloxanes, polyether group-modified silicone oil cyclomethicone, polyether siloxane copolymer, polyether siloxane copolymers, polyisobutylene, polyolefin, poppy oil, PPG alkyl ethers, PPG-10 cetyl ether, PPG-10 oleyl ether, PPG-11 stearyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-2 butyl ether, PPG-2 methyl ether, PPG-20 butyl ether, PPG-20 oleyl ether, PPG-22 butyl ether, PPG-23 oleyl ether, PPG-24 butyl ether, PPG-26 butyl ether, PPG-28 cetyl ether, PPG-3 methyl ether, PPG-3 myristyl ether, PPG-30 butyl ether, PPG-30 cetyl ether, PPG-30 isocetyl ether, PPG-30 oleyl ether, PPG-33 butyl ether, PPG-37 oleyl ether, PPG-4 butyl ether, PPG-4 lauryl ether, PPG-4 myristyl ether, PPG-40 butyl ether, PPG-5 butyl ether, PPG-50 cetyl ether, PPG-50 oleyl ether, PPG-52 butyl ether, PPG-53 butyl ether, PPG-7 lauryl ether, PPG-9 butyl ether, PPG-9-13 butyl ether, propyl myristate, propylene glycol dicaprate, propylene glycol dicaprylate, propylene glycol myristyl ether acetate, propylene glycol ricinoleate, rapeseed oil, rosehip oil, rye oil, safflower oil, sage oil, salmon oil, sesame oil, silicone oil, soya oil, soybean oil, stearyl caprate, stearyl dimethicone, stearyl heptanoate, stearyl propionate, sunflower oil, sweet almond oil, synthetic isoalkane, sysymbrium oil, syzigium aromaticum oil, tangerine oil, tea tree oil, therapeutic oils, tocopheryl acetate, tocopheryl linoleate, tridecyl ethylhexanoate, tridecyl isononanoate, triisocetyl citrate, unsaturated or polyunsaturated oils, vanilla oil, verbena oil, walnut oil, wheat germ glycerides, wheat germ oil, white petrolatum and mixtures thereof.

In one or more embodiments there is provided a composition comprising a petrolatum or a paraffin.

In one or more embodiments there is provided a composition in which the fatty alcohol has 14 or more carbons in their carbon chain; the fatty acid has 16 or more carbons in their carbon chain; the beeswax extract includes a mixture of fatty alcohols, a majority of which has at least 20 carbon atoms in their carbon chain, a fatty acid substituted with a hydroxyl group, cetyl alcohol, stearyl alcohol, arachidyl alcohol, behenyl alcohol, 1-triacontanol, hexadecanoic acid, stearic acid, arachidic acid, behenic acid; octacosanoic acid, 12-hydroxy stearic acid and/or mixtures thereof.

In one or more embodiments there is provided a composition in which the viscosity modifier and the active agent act synergistically to increase the viscosity.

In one or more embodiments there is provided a composition which is a foamable composition and the carrier comprises:
  a) about 60% to about 95% by weight of a hydrophobic solvent;
  b) an oleaginous foamer complex comprising:
    (1) about 0.1% to about 20% by weight of a fatty alcohol; and
    (2) about 0.1% to about 20% by weight of a fatty acid and/or a wax;
  c) a liquefied or compressed gas propellant;
wherein the percent by weight is based on weight foamable composition; wherein the ratio of composition other than propellant to propellant is from about 100:1 to about 100:30; and wherein upon dispensing the foamable carrier composition forms a breakable foam that is stable, yet breaks easily upon application of shear force.

In one or more embodiments there is provided a foamable composition in which the foam produced from the foamable composition has an average bubble size of less than about 300 microns of less, or less than about 200 microns, or less than about 150 microns.

In one or more embodiments there is provided a composition in which the composition further comprises at least one additional therapeutic agent selected from the group consisting of an antibiotic agent, a steroidal anti-inflammatory agent, an immunosuppressive agent, an immunomodulator, an immunoregulating agent, a hormonal agent, an androgen, an estrogen, a prostaglandin, an antiandrogen agent, a testosterone inhibitor, a dihydrotestosterone inhibitor, antibacterial agent, an antifungal agent, an antiviral agent, an antiparasitic agent, antimicrobial, a retinoid, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, a keratolytic agent, urea, a urea derivative, an alpha hydroxyl acid, lactic acid, glycolic acid, a beta-hydroxy acid, a protein, a peptide, a neuropeptide, an allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, an organo-metallic compound, and organo-boron compound, an organo-berrilium compound, an tellurium compound, talc, carbon, an anti wrinkle agent, a skin whitening agent, a skin protective agent, a masking agent, an anti-wart agent, a refatting agent, a lubricating agent and mixtures thereof.

In one or more embodiments there is provided a composition further comprising a surfactant.

In one or more embodiments there is provided a composition further comprising about 1% to about 25% by weight of a polar solvent or a penetration enhancer.

In one or more embodiments there is provided a composition in which the polar solvent is selected from polyols, glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, other glycols, sulfoxides, dimethylsulfoxide (DMSO), dimethylformanide, methyl dodecyl sulfoxide, dimethylacetamide, monooleate of ethoxylated glycerides (with 8 to 10 ethylene oxide units), azone (1-dodecylazacycloheptan-2-one), 2-(n-nonyl)-1,3-dioxolane, esters, isopropyl myristate/palmitate, ethyl acetate, butyl acetate, methyl proprionate, capric/caprylic triglycerides, octylmyristate, dodecyl-myristate, myristyl alcohol, lauryl alcohol, lauric acid, lauryl lactate ketones, amides, acetamide oleates, triolein; various alkanoic acids, caprylic acid, lactam compounds, azone; alkanols, dialkylamino acetates, and admixtures thereof; or from polyethylene glycol (PEG), PEG200 (MW (molecular weight) about 190-210 kD), PEG300 (MW about 285-315 kD), PEG400 (MW about 380-420 kD), PEG600 (MW about 570-630 kD), PEG 4000, PEG 6000, PEG 10000 and mixtures thereof.

In one or more embodiments there is provided a composition in which the penetration enhancer is selected from the group consisting of propylene glycol, butylene glycol, hexylene glycol, glycerol, pentaerythritol, sorbitol, mannitol, oligosaccharides, dimethyl isosorbide, monooleate of ethoxylated glycerides having about 8 to 10 ethylene oxide units, polyethylene glycol 200-600, transcutol, glycofurol and a cyclodextrin.

In one or more embodiments there is provided a composition in which the active agent is benzoyl peroxide.

In one or more embodiments there is provided a method for controlling formulation viscosity by selecting appropriate concentrations of a wax or fatty alcohol or fatty acid or a combination thereof and an active agent where the viscosity of the formulation can be increased, or stabilized by the addition of the active agent In one or more embodiments there is provided a method of preventing or treating or alleviating a disease or disorder, the method comprising administering any of the preceding compositions topically to a subject having or anticipated to have a disease or a disorder in need of treatment.

In one or more embodiments there is provided a method for intradermal delivery of the active agent into the skin with minimal or negligible transdermal delivery. In one or more alternative embodiments a formulation is provided to achieve intra mucosal delivery. In certain embodiments the composition provides for transdermal delivery. In one or more embodiments the composition can be used for prevention of a disease or disorder. The composition or foam is applied to a target surface or area in or on which prevention is sought. In other embodiments the composition or foam is used to treat or ameliorate a disease or disorder. In still further embodiments it may be used to provide a period of remission from the disease or disorder.

In one or more embodiments the composition is used for treating eye infections. In one or more embodiments the drug carrier is formulated for use on sensitive target areas such as sensitive or damaged skin areas, wounds, burns, mucosal membranes, body cavities and the eye. In one or more embodiments the composition is intended for use in treatment or prevention of eye infections. For sensitive use, hydrophobic solvents that are suitable for ophthalmic targets or for use in wounds or burns and are compatible with the active pharmaceutical ingredients are identified.

BRIEF DESCRIPTION OF THE DRAWINGS

The following figures are provided for the purpose of illustration only and are not intended to be limiting.

DETAILED DESCRIPTION

Figure 1:
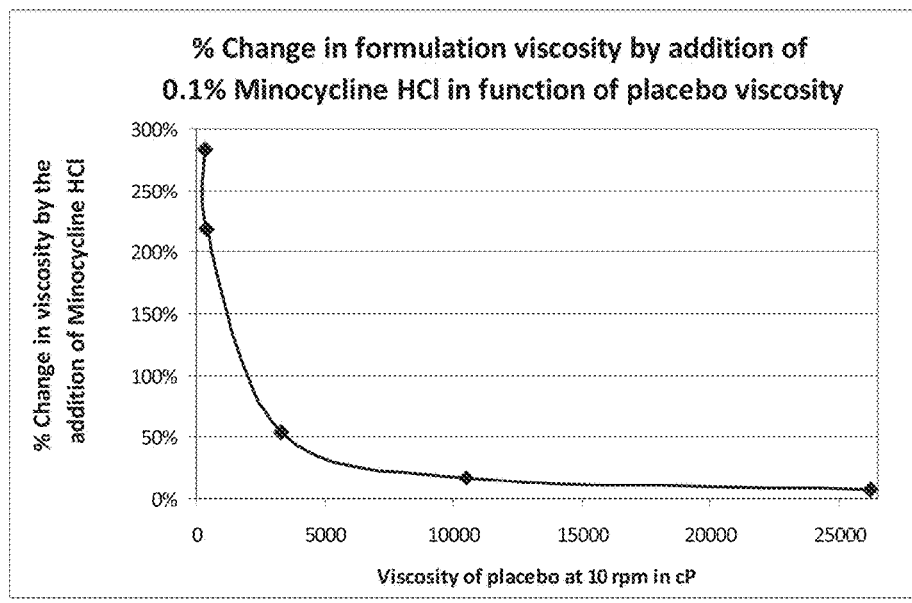
FIG. 1 is a graph of the percentage of change in formulation viscosity by addition of 0.1% Minocycline HCl as a function of placebo viscosity.

The gist of the present invention is based on the striking discovery that the addition of a low concentration of an suspended active agent into a composition or formulation comprising a oleaginous carrier comprising a hydrophobic solvent together with a second rheology modulator which may be a fatty acid and/or a fatty alcohol and/or a wax dramatically modulates the rheological properties of the composition and in particular can synergistically change the level of viscosity of a composition.

In one or more embodiments there is provided a composition or formulation for use as a vehicle or carrier comprising, a first rheology modulator comprising an suspended active agent in an amount necessary to modify controllably different rheological properties of the composition, a second rheology modulator comprising a second rheology modulator in an amount necessary to modify controllably the different rheological properties of the composition and a carrier.

In one or more embodiments there is provided a composition or formulation for use as a vehicle or carrier comprising a first rheology modulator comprising an suspended active agent in an amount necessary to modify controllably the different rheological properties of the composition, a second rheology modulator in an amount necessary to modify controllably the different rheological properties of the composition and an oleaginous carrier wherein adding a first modulator to an oleaginous carrier results in no significant or substantial change to the rheology as reflected in the viscosity of the composition; however further adding a second modulator to the composition unexpectedly results in a synergistic effect on the rheology as reflected in the viscosity of the composition. Alternatively first adding a second modulator to an oleaginous carrier results in an expected increase in the viscosity of the composition, however then further adding a first modulator to the composition surprisingly results in an unexpected synergistic effect on the viscosity of the composition. However, such synergistic affect is observed wherein the viscosity of the carrier or composition is less than about 25,000 centipoises (cPs) at room temperature prior to the addition of the first rheology modulator.

In one or more embodiments there is provided a composition as a carrier or vehicle in which a therapeutic rheology modulator or complex thereof is incorporated therein and in which the therapeutic agent is chemically stable and the formulation is physically stable and the therapeutic properties of the agent are sustained or substantially so.

In one or more embodiments there is provided a composition as a vehicle or carrier in which a therapeutic rheology modulator or complex thereof is incorporated therein and which further includes a surfactant and in which the active pharmaceutical agent is chemically stable and the formulation is physically stable and the therapeutic properties of the agent are sustained or substantially so.

In one or more embodiments there is provided a composition as a vehicle or carrier in which a therapeutic rheology modulator or complex thereof is incorporated therein which further includes one or more other therapeutic agents and in which the active pharmaceutical agent is chemically stable and the formulation is physically stable and the therapeutic properties of the agent are sustained or substantially so.

In one or more embodiments there is provided a composition as a vehicle or carrier comprising a therapeutic rheology modulator or complex thereof in a waterless or non aqueous environment and in which the active pharmaceutical agent is chemically stable and the formulation is physically stable and the therapeutic properties of the agent are sustained or substantially so.

In one or more embodiments there is provided a composition as a vehicle or carrier comprising a therapeutic rheology modulator or complex thereof in a substantially waterless or non aqueous environment and in which the active pharmaceutical agent is chemically stable and the formulation is physically stable and the therapeutic properties of the agent are sustained or substantially so.

In an embodiment or more embodiments there is provided a composition as a vehicle or carrier comprising a therapeutic rheology modulator or complex thereof in a substantially waterless or non aqueous environment, where the therapeutic agent has low or minimal susceptibility to water and can withstand up to about 10% water and more preferably up to about 5% water and in which the active pharmaceutical agent is chemically stable and the formulation is physically stable and the therapeutic properties of the agent are sustained or substantially so.

In an embodiment or more embodiments there is provided a composition as a vehicle or carrier comprising a therapeutic rheology modulator or complex thereof, where addition of low concentrations of the active agent has a strong and sometimes synergistic impact on the rheology of the composition and in which the active pharmaceutical agent is chemically stable and the formulation is physically stable and the therapeutic properties of the agent are sustained or substantially so.

In an embodiment or more embodiments there is provided a composition as a vehicle or carrier comprising a therapeutic rheology modulator or complex thereof, where addition of low concentrations of said therapeutic agent has a synergistic and dramatic impact on rheological properties of the composition for example the viscosity of the composition and in which the active pharmaceutical agent is chemically stable and the formulation is physically stable and the therapeutic properties of the agent are sustained or substantially so.

In an embodiment or more embodiments the therapeutic rheology modulator or the therapeutic agent has a low concentration of less than about 1%; or less than about 0.5%; or less than about 0.1%; or less than about 0.01%. In one or more other embodiments the therapeutic rheology modulator or the therapeutic agent has a medium concentration of less than about 10%; or less than about 5%; or less than about 3%; or less than about 2%. In one or more other embodiments the therapeutic rheology modulator or the therapeutic agent has a high concentration of less than about 30%; or less than about 25%; or less than about 20%; or less than about 15%. In one or more embodiments the concentration range of therapeutic rheology modulator or the therapeutic agent is between about 0.001% and about 0.1%; or is between about 0.01% and about 1%; or is between about 1% and about 10%; or is between about 10% and about 30%; or is between any two ranges, such as, between about 0.01% and about 30%.

In an embodiment or more embodiments there is provided a composition as a vehicle or carrier wherein the active agent is selected from a list comprising an antibiotic agent, a steroidal anti-inflammatory agent, an immunosuppressive agent, an immunomodulator, an immunoregulating agent, a hormonal agent, an androgen, an estrogen, a prostaglandin, an antiandrogen agent, a testosterone inhibitor, a dihydrotestosterone inhibitor, antibacterial agent, an antifungal agent, an antiviral agent, an antiparasitic agent, an antimicrobial agent a retinoid, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, a keratolytic agent, urea, a urea derivative, an alpha hydroxyl acid, lactic acid, glycolic acid, a beta-hydroxy acid, a protein, a peptide, a neuropeptide, an allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, an organo-metallic compound, and organo-boron compound, an organo-beryllium compound, a tellurium compound, talc, carbon, an anti wrinkle agent, a skin whitening agent, a skin protective agent, a masking agent, an anti-wart agent, a refatting agent, a lubricating agent and mixtures thereof.

In an embodiment or more embodiments there is provided a composition as a vehicle or carrier wherein active agent is a tetracycline.

In an embodiment or more embodiments there is provided a composition as a vehicle or carrier wherein the tetracycline is minocycline or doxycycline.

In an embodiment or more embodiments there is provided a composition as a vehicle or carrier wherein active agent is selected from a list comprising a cholesterol, mometasone furoate, doxycycline hyclate, salicylic acid, vitamin E, diclofenac, urea, terbinafine, permethrin, metronidazole, pimecrolimus benzoyl peroxide or salt thereof.

In one or more embodiments there is provided a composition as a vehicle or carrier wherein second rheology modulator is a fatty alcohol and/or a fatty acid and/or a wax.

In one or more embodiments there is provided a solid or semi-solid composition or gel. In one or more embodiments the composition or gel is a liquid. Examples of a liquid gel include where a propellant is added to the formulation (which prior to adding the propellant is a gel) or where the gel is loose or such that when subjected to gravity will pour or become liquid. In one or more embodiments the composition is thixotropic. In one or more embodiments when poured it displays flow but over time it reverts to being more viscous or gel like. In one or more embodiments when shear force is applied it displays flow but over time reverts to being more viscous or gel like. In one or more embodiments a solid gel becomes flowable and later with time becomes solid or semi solid. In one or more embodiments a semi-solid gel becomes flowable and later with time becomes solid or semi solid. In one or more embodiments a liquid gel is flowable and later with time becomes solid or semi solid.

In one or more embodiments there is provided a composition as a vehicle or carrier wherein second rheology modulator is a solid or semi-solid or a liquid.

In one or more embodiments there is provided a foamable composition for use as a vehicle or carrier in which therapeutic rheology modulator is stable or stabilized within foamable composition.

In one or more embodiments there is provided a method of preventing or treating or alleviating a disease or disorder, the method comprising administering the composition topically to a subject having or anticipated to having a disease or a disorder in need of treatment. In one or more embodiments the method of achieves a period of remission of the disease or disorder.

According to one or more embodiments, it is possible to make excellent lotions, creams, ointments, gels and foams from waterless or substantially waterless compositions. Such compositions containing first and second rheology modulators as described herein are also ideal carriers for active pharmaceutical agents that are soluble in polar solvents and which may be potentially unstable in an aqueous environment, for example, following a change in pH, or the introduction a metal catalyst or in the presence of an ionization or oxidation agent.

It has surprisingly been discovered that combinations of different types and concentrations of active agents with different second rheology modulators may result in modulations to the rheology of formulations in which the active pharmaceutical or cosmetic agent is chemically stable and furthermore, the formulation is physically stable as demonstrated herein in the Examples.

In one or more embodiments, the change in the formulation viscosity is related to the concentration of the active agent.

In one or more embodiments, the viscosity of the formulation is proportional to the concentration of the active agent: for example, the higher the concentration of the active agent, the higher the formulation viscosity. In one or more embodiments the relationship is exponential.

In one or more embodiments, the viscosity increasing effect of the active agent reaches a plateau when the concentration of the active agent is increased. In certain other embodiments the viscosity decreasing effect of the active agent likewise reaches a plateau when the concentration of the active agent is increased.

In one or more embodiments, the viscosity of the formulation containing the active agent is more than about twice the viscosity of the sample formulation is without the active agent, wherein the active agent is present at a concentration of less than about 10%, less than about 5%, less than about 1%, less than about 0.5%, less than about 0.1%, less than about 0.05%, or less than about 0.01%.

In one or more embodiments skin penetration of the active agent is improved. In one or more embodiments the penetration is primarily intradermal. In one or more embodiments there is little or no transdermal penetration. In one or more embodiments the active agent is concentrated in the statum corneum. In one or more embodiments the active agent is concentrated in the live skin layer. In one or more embodiments the active agent is distributed throughout the skin.

Active agents had practically no effect on the viscosity of a composition which did not comprise second rheology modulators. As shown in formulations of Example 2, mixtures of mineral oils or soybean oil or petrolatum and C12-C15 alkyl benzoate had a low viscosity. After the addition of a tetracycline such as Minocyclineminocycline HCl, the viscosity of the formulation remained practically unchanged and active agents sediment.

Similarly, as shown in formulations of Example 3, it appears that in formulations based on high amounts of semi-solid hydrophobic solvents, such as petrolatum or coconut oil, alone or in combination with fatty alcohols and/or fatty acids, the viscosity of the formulation remained unchanged after the addition of 0.1% Minocyclineminocycline HCl.

It was therefore surprisingly observed that addition of low concentrations of an active agent had a synergistic and dramatic impact on the oleaginous composition viscosity as for example shown in Example 4a. The addition of Minocyclineminocycline HCl to mineral oil-based formulations led to a very substantial increase in viscosity, despite the very low amount of Minocycline HCL used, namely 0.1%. These totally unexpected results show that the combination of a tetracycline, even at very low concentrations, with fatty alcohols, or fatty acids and/or waxes (e.g. hydrogenated castor oil, with or without beeswax) had a strong synergistic effect on oleaginous formulation viscosity. This effect was observed in compositions containing certain fatty alcohols such as myristyl alcohol or cetyl alcohol or stearyl alcohol.

It was found that adding a first modulator to an oleaginous carrier resulted in no significant or substantial change to the rheology as reflected in the viscosity of the composition; however further adding a second modulator to the composition unexpectedly resulted in a synergistic effect on the rheology as reflected in the viscosity of the composition. Alternatively first adding a second modulator to an oleaginous carrier resulted in an expected increase in the viscosity of the composition, however then further adding a first modulator to the composition surprisingly resulted in an unexpected synergistic effect on the viscosity of the composition. However such synergistic affect is observed wherein the viscosity of the carrier or composition is less than about 25,000 centipoises (cPs), less than about 12,000 cPs, less than about cPs 8,000 cPs, or less than about 2,000 cPs at room temperature prior to the addition of the first rheology modulator.

Very surprisingly, as described in Example 4c it was discovered that the addition of minocycline HCl to mineral oil-based formulations, containing as low as 5% of a fatty alcohol, or a fatty acid or a wax or a combination of a fatty alcohol and a wax, led to a very substantial increase in viscosity, where the increase in viscosity is dependent on the concentration of the active agent. It was noticed that formulations having a higher concentration of active agent had a higher viscosity. So there is a relationship between the amount of the active agent and resultant viscosity over a specific range of concentration typical for each active ingredient.

It was further observed that the combination of a tetracycline with a mixture of mineral oils, fatty alcohols, fatty acids and waxes had a strong synergistic effect and increased the formulation viscosity as shown in Example 4c. The viscosity of a formulation containing 0.50% minocycline HCl was about three times higher than the viscosity of the placebo formulation. It was also evident that the effect on the formulation viscosity was directly related to the concentration of the tetracycline: the higher the tetracycline concentration, the higher the viscosity of the formulation.

It was further discovered that in formulations based on petrolatum and various amounts of mineral oil, the influence of the combination of a tetracycline with fatty alcohols on formulation having initial high viscosity was minor. As shown in Example 5 when the viscosity of the placebo formulation is high, and the concentration of minocyline is low (e.g. 0.1%) no significant increase in viscosity was noticed. Formulations which contained low amounts of mineral oil exhibited a minor increase in viscosity upon the addition of 0.1% minocycline HCl (which with higher amounts of minocycline could have been more substantial). However, very surprisingly, it was observed that the addition of a very low amount of minocycline HCl greatly increased formulation viscosity, when the viscosity of the placebo formulation was low, which contained high amounts of mineral oil.

Figure 2:
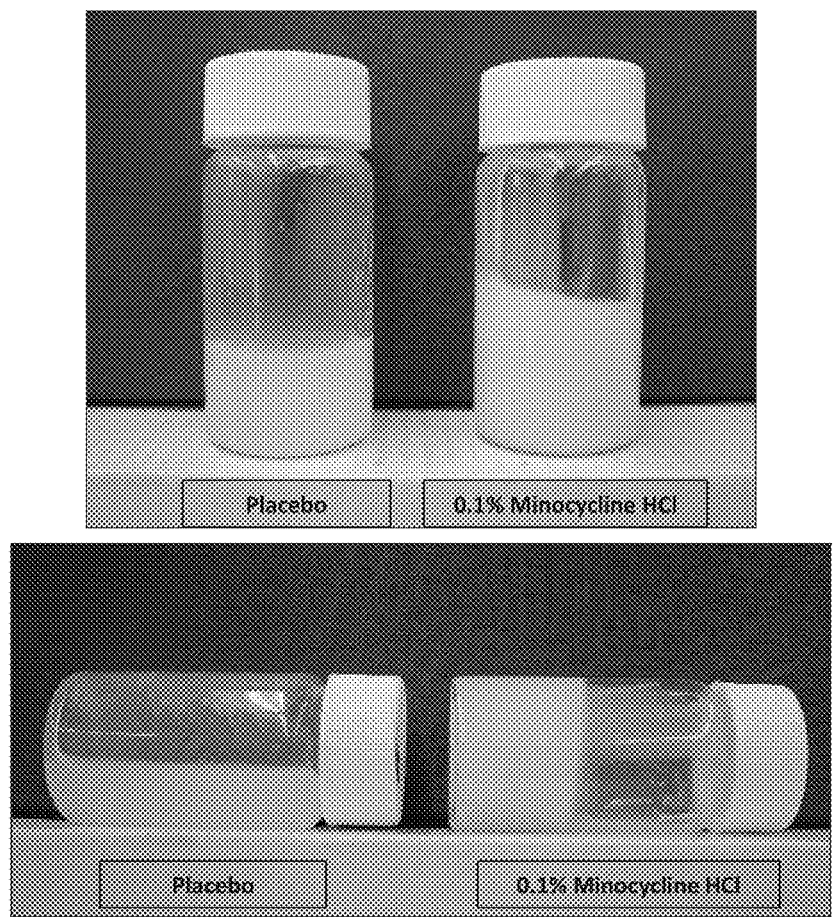
FIG. 2 is photographs of vials in horizontal and vertical position containing formulation 016 without active ingredient (left vial) and with 0.1% Minocycline HCl (right vial).

As shown in FIG. 1, the percentage of change in viscosity by the addition of minocycline HCl appears to be exponentially related to the viscosity of the formulation placebo. As shown in FIG. 2, the addition of minocycline HCl to the oleaginous formulation based on mineral oil changes the physical state of the formulation from a liquid to a semi-solid.

In one or more embodiments, the lower the viscosity of the placebo formulation, the greater the increase in formulation viscosity after addition of the active agent.

It was unexpectedly discovered that the combination of a tetracycline with a mixture of vegetable oils, fatty alcohols, fatty acids and waxes had a strong synergistic effect and increased the formulation viscosity. The viscosity of a formulation containing about 1% minocycline HCl was about twice as high as the viscosity of the placebo formulation. Moreover, the effect on the formulation viscosity was directly related to the concentration of the tetracycline: the higher the tetracycline concentration, the higher the viscosity of the formulation.

In one or more embodiments, there is provided an oleaginous formulation containing vegetable oils and a tetracycline in synergistic combination with a fatty alcohol, a fatty acid and a wax, wherein the viscosity of the formulation is increased by the addition of the active ingredient by more than about 20%, or by more than about 50%, or by more than about 100%, or by more than about 200%, or by more than about 300%, or by more than about 500%.

Tetracycline antibiotics are known to be very unstable active agents that are degraded by a wide range of commonly used pharmaceutical excipients. For example, it has been found that minocycline is degraded in a few days by different hydrophilic solvents (such as water, glycerin, sodium PCA, propylene glycol and polyethylene glycols), by water dispersed polymers (such as xanthan gum, poloxamers, carbomers, methocel, sodium carboxymethylcellulose) and by surfactants (such as polysorbates, sorbitan esters, polyoxyalkyl esters and lanolin-based surfactants). Thus, the achievement of a long term stable formulation of tetracycline antibiotics provided a major challenge.

Surprisingly, and despite the known instability of tetracycline antibiotics, the accelerated stability results of the formulation at 6 months at 40° C. showed minimal degradation of the active agent in the formulations. The formulations showed an extended accelerated stability for the tetracycline antibiotic active agent and an outstanding physical stability, wherein the viscosity of the formulation is substantially increased by the addition of the active agent.

In another experiment, a sample of formulation was stored during 6 months at 40° C. and tested for active agent content uniformity and physical stability. It was found that minocycline HCl was homogeneously dispersed into formulation even after prolonged incubation at 40° C. Furthermore, it was found that the formulation remained as a homogeneous gel after 6 months of incubation at 40° C.

In one or more embodiments, there is provided a formulation wherein the active agent is homogeneously dispersed in the formulation and remains homogeneously dispersed after 3 weeks of incubation at 40° C., or at one month, or at two months, or at three months, or at four months, or at five months, or at six months incubation at 40° C.

It was further discovered that the increase in viscosity was demonstrated in different mineral oil based formulations comprising a fatty alcohol and other active ingredients. To a lesser extent, an increase in formulation viscosity was observed with cholesterol which is also a 4-ring compound and with benzoyl peroxide. It can be noted that the strongest effect was observed with tetracycline compounds, such as minocycline HCl and tetracycline HCl (which is another compound of the tetracycline class). Even at concentrations as low as 0.05%, the addition of minocycline HCl to the formulations more than doubled the viscosity. Micronized preparations appear to have a more pronounced effect.

It was also unexpectedly discovered that viscosity increased dramatically after the addition of a wide range of different active ingredients to a mineral oil based formulation containing a hydrogenated castor oil instead of fatty alcohol or fatty acid [See Example 8]. The hydrogenated castor oil had a very strong synergistic effect with different active ingredients for example 0.1% Minocyclineminocycline HCl non micronized, mometasone furoate, terbinafine, metronidazole pimecrolimus. The viscosity of a formulation containing 0.1% non-micronized minocycline HCl was more than about 5 times as high as the viscosity of the formulation containing 0.1% micronized minocycline HCl. This is in contrast to the results with fatty alcohol where higher viscosity was observed with micronized minocycline HCL.

It was unexpectedly found that the addition of minocycline HCl to mineral oil-based formulations containing different concentrations of beeswax alone led to changes in viscosity depending on the amount of beeswax, at low concentration of Minocycline HCL used. Without being bound to any theory, one possibility may be that the addition of beeswax to oils can build a some sort of netted framework. It may further be assumed that when about 5% of beeswax is included in the composition, the netted framework is relatively weak and is broken or destabilized by the addition of Minocycline HCl, which may explain the decrease in formulation viscosity. However, it may be assumed that when 10% beeswax is included in the composition the netted framework is stronger and the addition of low amounts of Minocycline HCl further strengthens said netted framework leading to an increase in formulation viscosity.

Thus according to one or more embodiments there is provided a method for controlling formulation viscosity by selecting appropriate concentrations of a wax or fatty alcohol or fatty acid or a combination thereof and an active ingredient where the viscosity of the formulation can be increased, or stabilized by the addition of the active ingredient.

It was further discovered that tetracyclines like minocycline are incompatible with many surfactants, many hydrophilic solvents, an oil, a liquid branched fatty alcohol; a metal oxide and water. A detailed list of compatible substances and incompatible substances appears in Example 10.

Rheological Properties of Semisolids

Manufacturers of pharmaceutical gels, ointments and cosmetic creams have recognized the desirability of controlling their consistency. It must spread evenly and smoothly in various climates yet adhere well to the affected area without being tacky or difficult to remove.

Rheology of Gel Compositions and Gel Properties

Rigidity and viscosity are two separate rheological parameters used to characterize the mechanical properties of gels. Gel compositions should preferably posses the following properties.

1. Uniformity: The composition should be formulated so that it is and can remain uniform without separation or precipitation over time. This property is of high importance when the product is intended to be a pharmaceutical product.
2. Flowability: The composition, when placed in a tube or container and expelled under shear force should be flowable.
3. Quality: Upon release from the tube or container, the composition should generate a homogeneous gel. In one embodiment the gel is thixotropic.
4. Stability/Breakability: The fine balance between stability and breakability of the gel coming out of the tube or container is very delicate: on the one hand the gel should preferably not be very runny upon release from the tube or container and not lose its thixotropy property as a result of exposure to skin temperature; and on the other hand, it should be "breakable", i.e., it should spread easily, break down and absorb into the skin or membrane upon application of mild shear force.
5. Skin Feeling: To ensure patient compliance the skin feeling after application should be pleasant, and greasy or waxy residues should be minimal.
6. Non-irritating: The above requirements should be achieved with the awareness that formulation excipients, especially surfactants, can be irritating, and should preferably be eliminated from the composition or reduced as much as possible.
7. Delivery: The composition should also be designed to ensure efficient delivery of a therapeutic agent into the target site of treatment.
8. Compatibility: Finally, the first rheology modulating agent, which is a pharmaceutical or cosmetic active agent should be chemically compatible with the second viscosity modulating agent and with the whole list of ingredients in the composition.

Foamable Composition and Foam Properties

The ability to achieve quality foam with a substantial concentration of hydrophobic solvent without a surfactant is described in U.S. Provisional Application No. 61/248,144 filed Oct. 2, 2009 and titled "Surfactant-Free Water-Free Foamable Compositions, Breakable Foams And Their Uses," and in U.S. Provisional Application No. 61/322,148 filed Apr. 8, 2010 and titled "Surfactant-Free Water-Free Foamable Compositions, Breakable Foams And Gels And Their Uses." This is surprising, because usually, such solvents are not prone to creating a foam. The challenge is not just to achieve a quality foam but also to attain a formulation that will satisfy a plurality of two, three, four, five, six or more of the following property specifications simultaneously.

Notably, the pressurized composition is flowable and releases a foam freely, even though it might be expected that such concentrations of a fatty alcohol and fatty acid would make the hydrophobic solvent 'gel' or 'semi-solid'.

1. Uniformity: The composition should be formulated so that it is uniform and can remain uniform without phase separation or precipitation over time. This property is of high importance when the product is intended to be a pharmaceutical product.
2. Flowability: The composition, when placed in an aerosol container and pressurized should be flowable such that it can be expelled through the canister valve. It should preferably also be shakable inside the container. These requirements create a formulation challenge, because low or non-viscous flowable and shakable compositions are prone to undergo phase separation or precipitation.
3. Quality: Upon release from the can, the composition should generate a foam of good or excellent quality having low density and small bubble size.
4. Stability/Breakability: The fine balance between stability and breakability of the foam coming out of the container is very delicate: on one hand the foam should preferable not be "quick breaking", i.e., it should be at least short term stable upon release from the pressurized container and not break as a result of exposure to skin temperature; and on the other hand, it should be "breakable", i.e., it should spread easily, break down and absorb into the skin or membrane upon application of mild shear force.
5. Skin Feeling: To ensure patient compliance the skin feeling after application should be pleasant, and greasy or waxy residues should be minimal.
6. Non-irritating: The above requirements should be achieved with the awareness that formulation excipients, especially surfactants, can be irritating, and should preferably be eliminated from the composition or reduced as much as possible.
7. Delivery: Finally, the composition should also be designed to ensure efficient delivery of a therapeutic agent into the target site of treatment.

Based on extensive investigations and trial and error experiments, it has been found that such properties can be achieved for formulations as disclosed in U.S. Provisional Application No. 61/248,144 filed Oct. 2, 2009 and titled "Surfactant-Free Water-Free Foamable Compositions, Breakable Foams And Their Uses," and in U.S. Provisional Application No. 61/322,148 filed Apr. 8, 2010 and titled "Surfactant-Free Water-Free Foamable Compositions, Breakable Foams And Gels And Their Uses," and which are further advantageous because of the ability of hydrophobic solvents to dissolve or suspend certain active agents while providing an environment for the active agent which assists in preventing their degradation.

Compositions

All % values are provided on a weight (w/w) basis.

In one or more embodiments where ever a phrase is used to refer to a concentration of above X % or below X % it can also include X % or of above about X % or below about X % it can also include about X %.

In one or more embodiments the term "about" has its usual meaning in the context of pharmaceutical and cosmetic formulations to allow for reasonable variations in amounts that can achieve the same effect. In one or more embodiments about can encompass a range of plus and minus 20%. In one or more embodiments about can encompass a range of plus and minus 10%.

In one or more embodiments there is provided a composition for cosmetic or pharmaceutical application comprising:
a) a first rheology modulator comprising a suspended active agent
b) a second rheology modulator selected from the list of (i) at least one at least one fatty alcohol, (ii) at least one fatty acid, (iii) at least one wax; and mixtures thereof; and
c) a carrier,
wherein the suspended active agent is a pharmaceutical or cosmetic suspended active agent;
wherein the rheology of the composition after addition of the first modulator and second modulator to the carrier is better than the rheology of the composition after the addition of the second modulator to the carrier without the first modulator and is better than the rheology of the composition after the addition of the first modulator to the carrier without the second modulator.

In certain embodiments, the viscosity of the carrier or composition without the addition of the first rheology modulator is less than about 25,000 centipoises (cPs) at room temperature.

In one or more embodiments the composition forms a gel. The gel may be a liquid gel, a semi-solid gel or a solid gel. The gel may further be an air gel, hydro gel or an oleaginous (organo) gel.

In one or more embodiments a liquefied or compressed gas propellant is added to the composition according to the different embodiments mentioned above thereby transforming the gel into a foamable composition. Upon release from an aerosol container, the foamable composition forms an expanded foam suitable for topical administration. In one or more embodiments the foamable composition is either a breakable or quickly breaking foam. In one or more embodiments the foamable composition is substantially surfactant free. In one or more other embodiments it is essentially free of any surfactants.

In one or more embodiments oily emollients are added to the composition to provide or improve a pleasant skin feeling, and/or lubricating effect with reduced friction. In one or more embodiments volatile silicones are added to reduce greasy feeling. In one or more embodiments waxes are added to improve rheology or stabilize the composition's gels or structure.

In an embodiment, the wax can be a liquid wax, a solid wax, an animal wax, a vegetable wax, a mineral wax, a natural wax or a synthetic wax. In an embodiment the wax is selected from a list comprising paraffin wax, beeswax, hydrogenated castor oil or mixtures thereof. In an embodiment the wax is a polyolefin. In one or more embodiments there is provided a composition comprising a paraffin wax. In one or more embodiments the paraffin wax can have a melting point form about 37° C. In one or more embodiments the paraffin wax comprises of alkane chains of between about $C_{20}H_{42}$ to $C_{40}H_{82}$. In one or more embodiments the chains are substantially straight chain. In some embodiments branched or unsaturated molecules can be present. Branched chains are sometimes referred to as isoparaffins. In one or more embodiments the paraffin wax can be selected from the group consisting of paraffin wax 58-62° C., paraffin wax 51-53° C., and paraffin wax 42-44° C., or mixtures thereof. In one or more other embodiments other melting point ranges can be selected such as 125° F. to 135° F.; 127° F. to 130° F.; 130° F. to 135° F.; 135° F. to 145° F.; 140° F. to 145° F.; 150° F. to 155° F.; 150° F. to 165° F.; 160° F. to 165° F.; or such as 43-46° C.; 46-53° C.; 48-50°

C.; 52-54° C.; 53-55° C.; 54-57° C.; 54-58° C.; 58-60° C.; 59-61° C.; 60-62° C.; 62-66° C.; 65-68° C.; or any other similar or relative range(s) or mixtures thereof. In an embodiment the wax is fully refined. In an embodiment it is suitable for cosmetic use. In an embodiment it is suitable for pharmaceutical use. In an embodiment the paraffin wax is soft.

In one or more embodiments antioxidants can be used to prevent degradation/oxidation, for example, butylated hydroxytoluene, which is a fat soluble antioxidant.

According to one or more embodiments, the composition further comprises one or more other cosmetic active agents or a pharmaceutical active agents (severally and interchangeably termed herein "active agent") which may or may not have a rheology modulating effect.

Surfactants play a role in foam formation and induce foam stability. In one or more embodiments the formulation is substantially free of surfactants. In one or more other embodiments it is essentially free of any surfactants. In one or more alternative embodiments a small amount of surfactant may be added preferably less than 1%. In one or more embodiments foam adjuvants (e.g. fatty alcohols and fatty acids) and additives (such as SiO2 which acts as a thickener and can provide thixotropy) are added to improve rheology or stabilize foam structure or as a protective agent.

In one or more embodiments the composition is a foamable composition and comprises propellant. Upon release from an aerosol container, the foamable composition forms an expanded breakable foam suitable for topical administration.

The composition is suitable for administration to various body areas, including, but not limited to the skin, a body surface, a body cavity, a mucosal surface, e.g., the mucosa of the nose, mouth and eye, the ear, the respiratory system, the vagina or the rectum (severally and interchangeably termed herein "target site").

In one or more embodiments, the composition is waterless. By waterless is meant that the composition contains no or substantially no, free or unassociated or absorbed water. It will be understood by a person of the art that to the extent the waterless solvents and substances miscible with them of the present disclosure are hydrophilic, they can contain water in an associated or unfree or absorbed form and may absorb water from the atmosphere.

In one or more embodiments the carrier comprises an active pharmaceutical or cosmetic agent which degrades in the presence of water, and in such cases the presence of water in the composition is clearly not desirable. Thus, in certain preferred embodiments, the composition is waterless. In other embodiments the active agent may tolerate the presence of a small amount of water and the waterless composition is substantially non-aqueous. The term "substantially non-aqueous" is intended to indicate that the waterless composition has water content preferably below about 2%, such as, below about 1.5%, below about 1%; or below about 0.5%.

In one or more embodiments, at least a portion of the therapeutic agent is suspended or dissolved evenly throughout the entire composition. In one or more other embodiments the first rheology modulator is a soluble active agent. For example when hydrogenated caster oil in mineral oil is challenged with cholesterol the viscosity increases by about 200%. In certain embodiments two or more first rheology modulators may be used in combination. Such combinations can be of two or more solid agents, or of one or more solid agents (insoluble or partially soluble) and one or more soluble agents or two or more soluble agents.

It has been discovered that formulations containing high amount of a hydrophobic solvents (such as mineral oil) are not prone to high viscosity or foaming. Surprisingly, it has been discovered that the combination of a rheology modulating active agent and/or a fatty alcohol and/or fatty acid and/or a wax has viscosity and foam boosting properties and provides gels and foams of good quality. It has been discovered that when rheology modulating active agents are added to fatty alcohols and/or fatty acids, for example, with a saturated carbon chain of between 14 to 22 carbons it can cause a rheology effect, such as, a synergistic viscosity effect resulting in composition having outstanding viscosity properties Furthermore, the formulations of the present invention can provide foams of good quality in the presence of various active ingredients with or without surfactants.

In one or more embodiments, the active agent is vitamin D or a derivative or analog thereof.

In one or more embodiments, the active agent is calcipotriol.

In one or more embodiments, the active agent is calcitriol.

In one or more embodiments, the active agent is selected from a list comprising a tetracycline, cholesterol, mometasone furoate, doxycycline hyclate, salicylic acid, vitamin E, diclofenac, urea, terbinafine, permethrin, metronidazole, pimecrolimus, benzoyl peroxide or salt thereof.

In one or more embodiments, the tetracycline is minocycline or doxycycline or tetracycline.

In one or more embodiments, the composition is essentially free of polyols.

In one or more embodiments there is provided a surfactant free composition that is also free of short chain alcohols and/or polyol free and/or polymeric free.

In one or more embodiments, composition is capable of providing intradermal delivery of the active agent into the skin with minimal or negligible transdermal delivery.

In one or more embodiments, the composition has some preservative efficacy.

In one or more embodiments, the composition is for use in eye infections.

In one or more embodiments, the composition is physically and chemically stable for at least two months.

In one or more embodiments, the composition is physically and chemically stable for at least three months.

In one or more embodiments, the composition is physically and chemically stable for at least six months.

Hydrophobic Solvent

In an embodiment, the composition of the present invention comprises at least one hydrophobic organic solvent. A "hydrophobic organic solvent" (also termed "hydrophobic solvent") as used herein refers to a material having solubility in distilled water at ambient temperature of less than about 1 gm per 100 mL, more preferably less than about 0.5 gm per 100 mL, and most preferably less than about 0.1 gm per 100 mL. It is liquid at ambient temperature. The identification of a "hydrophobic solvent", as used herein, is not intended to characterize the solubilization capabilities of the solvent for any specific active agent or any other component of the foamable composition. Rather, such term is provided to aid in the identification of materials suitable for use as a hydrophobic solvent in the compositions described herein.

In one or more embodiments the hydrophobic solvent is present at a concentration of about 60% to about 95% or about 65% to about 90%; or about 70% to about 90% or about 75% to about 85%.

In one or more embodiments, the composition of the present invention comprises at least one hydrophobic solvent, selected from the group consisting of a mineral oil, a hydrocarbon oil, an ester oil, a triglyceride oil, an oil of plant origin, an oil from animal origin, an unsaturated or polyunsaturated oil, a diglyceride, a PPG alkyl ether and a silicone oil.

As exemplified herein, members of each of the above listed groups of hydrophobic solvents have been found to be compatible with hydrophobic tetracyclines, such as minocycline and doxycycline.

Non-limiting examples of hydrocarbon oils include mineral oil, liquid paraffin, an isoparaffin, a polyalphaolefin, a polyolefin, polyisobutylene, a synthetic isoalkane, isohexadecane and isododecane.

Non-limiting examples of ester oils include alkyl benzoate, alkyl octanoate, C12-C15 alkyl benzoate, C12-C15 alkyl octanoate, arachidyl behenate, arachidyl propionate, benzyl laurate, benzyl myristate, benzyl palmitate, bis (octyldodecyl stearoyl) dimer dilinoleate, butyl myristate, butyl stearate, cetearyl ethylhexanoate, cetearyl isononanoate, cetyl acetate, cetyl ethylhexanoate, cetyl lactate, cetyl myristate, cetyl octanoate, cetyl palmitate, cetyl ricinoleate, decyl oleate, diethyleneglycol diethylhexanoate, diethyleneglycol dioctanoate, diethyleneglycol diisononanoate, diethyleneglycol diisononanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumerate, dioctyl malate, dioctyl sebacate, dodecyl oleate, ethylhexyl palmitate, ester derivatives of lanolic acid, ethylhexyl cocoate, ethylhexyl ethylhexanoate, ethylhexyl hydroxystarate, ethylhexyl isononanoate, ethylhexyl palmytate, ethylhexyl pelargonate, ethylhexyl stearate, hexadecyl stearate, hexyl laurate, isoamyl laurate, isocetyl isocetyl behenate, isocetyl lanolate, isocetyl palmitate, isocetyl stearate, isocetyl salicylate, isocetyl stearate, isocetyl stearoyl stearate, isocetearyl octanoate, isodecyl ethylhexanoate, isodecyl isononanoate, isodecyl oleate, isononyl isononanoate, isodecyl oleate, isohexyl decanoate, isononyl octanoate, isopropyl isostearate, isopropyl lanolate, isopropyl laurate, isopropyl myristate, isopropyl palmitate, isopropyl stearate, isostearyl behenate, isosteary citrate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isosteary salicylate, isosteary tartarate, isotridecyl isononanoate, isotridecyl isononanoate, lauryl lactate, myristyl lactate, myristyl myristate, myristyl neopentanoate, myristyl propionate, octyldodecyl myristate, neopentylglycol dicaprate, octyl dodecanol, octyl stearate, octyl palmitate, octyldodecyl behenate, octyldodecyl hydroxystearate, octyldodecyl myristate, octyldodecyl stearoyl stearate, oleyl erucate, oleyl lactate, oleyl oleate, propyl myristate, propylene glycol myristyl ether acetate, propylene glycol dicaprate, propylene glycol dicaprylate, propylene glycol dicaprylate, maleated soybean oil, stearyl caprate, stearyl heptanoate, stearyl propionate, tocopheryl acetate, tocopheryl linoleate, glyceryl oleate, tridecyl ethylhexanoate, tridecyl isononanoate and triisocetyl citrate.

Non-limiting examples of triglycerides and oils of plant origin include alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil.

Non-limiting examples of PPG alkyl ethers include PPG-2 butyl ether, PPG-4 butyl ether, PPG-5 butyl ether, PPG-9 butyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-20 butyl ether, PPG-22 butyl ether, PPG-24 butyl ether, PPG-26 butyl ether, PPG-30 butyl ether, PPG-33 butyl ether, PPG-40 butyl ether, PPG-52 butyl ether, PPG-53 butyl ether, PPG-10 cetyl ether, PPG-28 cetyl ether, PPG-30 cetyl ether, PPG-50 cetyl ether, PPG-30 isocetyl ether, PPG-4 lauryl ether, PPG-7 lauryl ether, PPG-2 methyl ether, PPG-3 methyl ether, PPG-3 myristyl ether, PPG-4 myristyl ether, PPG-10 oleyl ether, PPG-20 oleyl ether, PPG-23 oleyl ether, PPG-30 oleyl ether, PPG-37 oleyl ether, PPG-40 butyl ether, PPG-50 oleyl ether and PPG-11 stearyl ether. Preferred PPG alky ethers according to the present invention include PPG-15 stearyl ether, PPG-2 butyl ether and PPG-9-13 butyl ether.

Non-limiting examples of oils from animal origin include herring oil, cod-liver oil and salmon oil.

The hydrophobic solvent may be an emollient, i.e., a hydrophobic liquid having a softening or soothing effect especially to the skin. In some embodiments the liquid oil may contain a solid or semi solid hydrophobic matter at room temperature.

Essential oil, which is usually a concentrated, hydrophobic liquid containing volatile aroma compounds from plants usually conveying characteristic fragrances. Non limiting examples include lavender, peppermint, and eucalyptus. A therapeutic oil is a hydrophobic liquid which is said to have a therapeutic effect or to have associated with it certain healing properties. Therapeutic oils contain active biologically occurring molecules and, upon topical application, exert a therapeutic effect. Non limiting examples include manuka oil, rosehip oil, which contains retinoids and is known to reduce acne and post-acne scars, and tea tree oil, which possesses anti-microbial activity including antibacterial, antifungal and antiviral properties as well as any other therapeutically beneficial oil known in the art of herbal medication. Many essential oils, are considered "therapeutic oils." Other non limiting examples of essential oils are basil, camphor, cardamom, carrot, citronella, clary sage, clove, cypress, frankincense, ginger, grapefruit, hyssop, jasmine, lavender, lemon, mandarin, marjoram, myrrh, neroli, nutmeg, petitgrain, sage, tangerine, vanilla and verbena, Some embodiments include silicone oils. Non-limiting examples of silicone oils include a cyclomethicone, a dimethicone, a polyalkyl siloxane, a polyaryl siloxane, a polyalkylaryl siloxane, a polyether siloxane copolymer, a poly (dimethylsiloxane)-(diphenyl-siloxane) copolymer, a dimethyl polysiloxane, an epoxy-modified silicone oil, a fatty acid-modified silicone oil, a fluoro group-modified silicone oil, a methylphenylpolysiloxane, phenyl trimethicone and a polyether group-modified silicone oil. In some embodiments, the silicone oil is cyclomethicone, cyclotetrasiloxane, cyclohexasiloxane, phyenyltrimethicone, Dow coming 246 Fluid (d6+d5) (cyclohexasiloxane & cyclopentasiloxane), Dow Corning 244 Fluid (cyclotetrasiloxane), Cyclomethicone 5-NF (cyclopentasiloxane), stearyl dimethicone, phenyltrimethicone, cetyl dimethicone, caprylyl methicone, PEG/PPG 18/18 dimethicone, or dimethiconol.

In one or more embodiments, the hydrophobic solvent may be selected from cyclomethicone; isopropyl myristate, PPG-15 stearyl ether; octyldodecanol; isohexadecanol, diisopropyl adipate; cetearyl octanoate; hydrogenated castor oil; MCT oil; heavy mineral oil; light mineral oil; coconut oil and soybean oil, castor oil, cocoglycerides, disopropyl adipate, beeswax, isododecane, gelled mineral oil, white petrolatum, petrolatum, paraffin 51-53, calendula oil, shea butter, grape seed oil, almond oil, jojoba oil, avocado oil, peanut oil, and hard fat and combination thereof.

Mixtures of two or more hydrophobic solvents in the same composition is contemplated. Furthermore, in certain embodiments, the use of mixtures of two or more hydrophobic solvents is preferred.

Yet, in certain embodiments, the hydrophobic solvent is a mixture of one or more liquid hydrophobic solvents, as listed above, which an additional hydrophobic substance, which is not liquid (such as petrolatum), provided that the mixture of all hydrophobic substances (excluding the oleaginous foamer complexes), is liquid at ambient temperature. In an embodiment the resultant mixture upon including propellant is liquid at ambient temperature. For example petrolatum may be added to provide a degree of occlusivity so that the formulation when applied to a skin surface can operate to increase skin moisture and/or reduced transdermal water loss. In certain other embodiments fluidity of the composition can be achieved by utilizing liquidizing solvents (e.g. C12 C15 Alkyl benzoate) and/or liquefied propellants and/or optionally liquid adjuvants. Inclusion of higher amounts of propellant was found useful in order to improve flowability of the formulation from the canister or by using propellants having a higher vapor pressure.

Composition Components

The composition components comprise: a carrier, a first rheology modulator and a second rheology modifier. The carrier can comprise, for example a hydrophobic solvent. In one or more embodiments the carrier can comprise about 60% to about 95% by weight of the composition. The first rheology modulator is a therapeutic rheology modulator. In one or more embodiments it can comprise about 0.001% to about 30% by weight of the composition. The second rheology modulator comprises a fatty alcohol; a fatty acid; a wax and mixtures thereof. In one or more embodiments it can comprising about 0.1% to about 20% by weight of a fatty alcohol; and/or about 0.1% to about 20% by weight of a fatty acid; and/or a wax and a third member which is a active agent. In one or more embodiments the carrier is present at a concentration of about 60% to about 95% or about 65% to about 90%; or about 70% to about 90% or about 75% to about 85%. In certain embodiments the amount of the second rheology modulator comprises about 0.4% to about 18% by weight. In certain embodiments the amount of the second modulator comprises about 0.6% to about 12% by weight. In certain embodiments the amount of the second modulator comprises about 0.8% to about 10% by weight. In certain embodiments the amount of the second modulator comprises about 2% to about 7% by weight. In certain other embodiments, the concentration of the second modulator can be within any one of the following ranges (i) between about 0.1% and about 1%, (ii) between about 1% and about 5%, (iii) between about 5% and about 10%, or (iv) between about 10% and about 20%. In one or more embodiments, each member is at a concentration at about 5% to about 10% by weight. In one or more embodiments the amount of the first modulator is present at a concentration of less than about 1%, or less than about 0.5%, or less than about 0.1%, or less than about 0.01%

Second Rheology Modulators

The second rheology modulator (waxes, fatty alcohols and fatty acids) may be solids semi-solids or liquids. Unlike aqueous liquids, which are rather easy to solidify due to their hydrogen bond forming ability, oils are difficult to solidify.

Fatty Alcohol

In an embodiment, the second rheology modulator includes a fatty alcohol. The fatty alcohol which acts as an adjuvant is included in the gel and foamable compositions as a main constituent, to evolve the solidifying effect of the gel and/or the foaming property of the composition and/or to stabilize the foam. In one or more embodiments, the fatty alcohol is selected from the group consisting of fatty alcohols having 15 or more carbons in their carbon chain, such as cetyl alcohol and stearyl alcohol (or mixtures thereof). In one or more embodiments, the fatty alcohol is selected from the group consisting of fatty alcohols having 14 or more carbons in their carbon chain, such as myristyl alcohol (with 14 carbons). Other examples of fatty alcohols are arachidyl alcohol (C20), behenyl alcohol (C22), tetracosanol, hexacosanol, octacosanol, triacontanol, tetratriacontanol, 1-triacontanol (C30), as well as alcohols with longer carbon chains (up to C50). In one or more preferred embodiments, the fatty alcohol is myristyl alcohol, cetyl alcohol, stearyl alcohol and combinations thereof. Fatty alcohols, derived from beeswax and including a mixture of alcohols, a majority of which has at least 20 carbon atoms in their carbon chain, are suitable as fatty alcohols in the context herein. In certain embodiments the amount of the fatty alcohol required to support the foam system can be approximately inversely related to the length of its carbon chains. In one or more other embodiments, the fatty alcohol is selected from the group consisting of fatty alcohols having 14 or less carbons in their carbon chain, such as myristyl alcohol or lauryl alcohol. In an embodiment the fatty alcohol is a solid at room temperature. Fatty alcohols are also useful in facilitating improved spreadability and absorption of the composition.

Fatty alcohols are amphiphatic, however unlike customary surfactants, they do not usually function as stand-alone surfactants, because of their very weak emulsifying capacity. They are occasionally used as non-ionic co-emulsifiers, i.e., and are commonly used as thickeners (*Surfactants in personal care products and decorative cosmetics* By Linda D. Rhein, Mitchell Schlossman, Anthony O'Lenick, P., Third Edition, 2006, p. 247). Fatty alcohols are generally regarded as safe and they are not considered as irritants.

An important property of the fatty alcohols used in context of the composition disclosed herein is related to their therapeutic properties per se. Long chain saturated and mono unsaturated fatty alcohols, e.g., stearyl alcohol, erucyl alcohol, arachidyl alcohol and behenyl alcohol (docosanol) have been reported to possess antiviral, anti-infective, anti-proliferative and anti-inflammatory properties. Longer chain fatty alcohols, e.g., tetracosanol, hexacosanol, heptacosanol, octacosanol, triacontanol, etc., are also known for their metabolism modifying properties and tissue energizing properties.

Fatty Acid

In an embodiment, the second rheology modulator further includes a fatty acid. The fatty acid which acts as an adjuvant is included in the gel and foamable compositions to evolve solidifying effect of the gel and/or the foaming property of the composition and/or to stabilize the foam. In one or more embodiments the fatty acid can have 16 or more carbons in its carbon chain, such as hexadecanoic acid (C16), heptadecanoic acid, stearic acid (C18), arachidic acid (C20), behenic acid (C22), tetracosanoic acid (C24), hexacosanoic acid (C26, heptacosanoic acid (C27), octacosanoic acid (C28), triacontanoic acid, dotriacontanoic acid, tritriacontanoic acid, tetratriacontanoic acid and pentatriacontanoic acid as well as fatty acids with longer carbon chains (up to C50), or mixtures thereof. In one or more other embodiments, the fatty acid is selected from the group consisting of fatty acids having 14 or less carbons in their carbon chain, such as dodecanoic acid, myristic acid, myristoleic acid, and lauric acid.

In certain embodiments, the carbon atom chain of the fatty acid may have at least one double bond; alternatively, the fatty acid can be a branched fatty acid. The carbon chain of the fatty acid also can be substituted with a hydroxyl group, such as 12-hydroxy stearic acid. In an embodiment the fatty alcohol is a solid at room temperature. In one or more preferred embodiments, the fatty acid is stearic acid.

Waxes

In certain embodiments the oleaginous second rheology modulator may include a wax. The wax which acts as an adjuvant in a gel and is included in the gel or foamable compositions to evolve solidifying effect of the gel and/or the foaming property of the composition and/or to stabilize the foam. Wax refers to beeswax or another substance with similar properties. The term wax refers to a class of substances with properties similar to beeswax, in respect of (i) plastic behavior at normal ambient temperatures, a melting point above approximately 45° C., (iii) a relatively low viscosity when melted (unlike many plastics); and (iv) hydrophobic nature. Suitable exemplary waxes which can be incorporated into the formulation include animal, vegetable, mineral or silicone based waxes which may be natural or synthetic such as, for example: beeswax, chinese wax, lanolin (wool wax), shellac wax, bayberry wax, candelilla wax, carnauba wax, castor wax, esparto wax, japan wax, ouricury wax, rice bran wax, soy wax, hydrogenated oil such ashydrogenated castor oil, hydrogenated cottonseed oil, or hydrogenated jojoba oil, mink wax, motan wax, ouricury wax, ozokerite, PEG-6 beeswax, rezowax, spent grain wax, stearyl dimethicone, paraffin waxes, such as paraffin 58-62° C., paraffin 51-53° C. wax, paraffin 42-44° C. wax, and the like and mixtures thereof. In certain embodiments the term wax can extend to hydrogenated oils. In one or more embodiments the wax is selected from a list comprising of a solid wax, an animal wax, a vegetable wax, a mineral wax, a natural wax or a synthetic wax. In certain embodiments the term wax can extend to hydrogenated oils. In an embodiment wax includes polyolefins. In one or more preferred embodiments, the wax is a beeswax or hydrogenated castor oil.

In one or more embodiments, the wax is a polyolefin such as polyethylene, polypropylene, polymethylpentene, polybutene, a polyolefin elastomer, polyisobutylene, ethylene propylene rubber, ethylene propylene diene Monomer (M-class) rubber, polyethylene terephthalate, polydicyclopentadiene, linear polyolefins, branched polyolefins, cyclic polyolefins, low density polyolefins, high density polyolefins, polyolefins with a low molecular weight, polyolefins with a high molecular weight, halogenated polyolefins and the like and mixture thereof.

Combination of a Fatty Alcohol or a Fatty Acid and/or a Wax Together with a Therapeutic Active Agent Example 2 describes formulations where adding an active agent to oleaginous hydrophobic solvents does not affect viscosity of the formulation. When, however, the same formulation contains a fatty alcohol (or a mixture of fatty alcohols) or a fatty acid (or a mixture of fatty acids) or a wax (or a mixture of waxes), or a combination of a fatty alcohol with a wax or a fatty acid with a wax the therapeutic active agent can, surprisingly, act synergistically to produce enhanced viscosity (Example 4). These successful combinations of an active agent and a fatty alcohol or a fatty acid or a wax or alternatively an active agent and a fatty alcohol and/or a wax or a fatty acid and/or wax are referred to herein as "viscosity inducing complexes".

In one or more embodiments, the viscosity inducing complex is a synergistic combination of an active agent and a fatty alcohol (or a mixture of fatty alcohols) or a fatty acid (or a mixture of fatty acids) or a wax or alternatively an active agent and a fatty alcohol (or a mixture of fatty alcohols) and/or a wax (or a mixture of waxes) or alternatively an active agent and a fatty acid (or a mixture of fatty acids) and/or a wax (or a mixture of waxes).

In one or more embodiments, the viscosity inducing complex is a synergistic combination of a fatty alcohol (or a mixture of fatty alcohols) and a wax (or a mixture of waxes).

In one or more embodiments, the viscosity inducing complex is a synergistic combination of a fatty acid (or a mixture of fatty acids) and a wax (or a mixture of waxes).

In one or more embodiments the range of ratio of fatty alcohol to wax or fatty acid to wax can be about 100:1 to about 1:100; or about 90:1 to about 1:45; or about 80:1 to about 1:40; or about 70:1 to about 1:35; or about 60:1 to about 1:30; or about 50:1 to about 1:25; or about 40:1 to about 1:20; or about 30:1 to about 1:15; or about 20:1 to about 1:10; or about 15:1 to about 1:5; or about 10:1 to about 1:1; or any ranges in between such as 1:20 to 20:1, or preferably from 1:10 to 10:1.

In one or more embodiments the range of ratio of therapeutic soluble active agent to second rheology modulator can be about 1:50000 to about 250:1; or about 1:25000 to about 1:150; or about 1:10000 to about 100:1; or about 1:5000 to about 50:1; or about 1:2500 to about 1:25; or about 1:1000 to about 10:1; or about 1:100 to about 1:1; or about 1:10 to about 10:1 or any ranges in between.

Propellant

Certain compositions comprising a hydrophobic solvent, together with a first rheology modulator (a suspended active agent) and a second rheology modulator without any surface active agents result, upon packaging in an aerosol container and adding a propellant, a shakable and homogenous foamable composition, which releases a breakable foam with good to excellent quality (as defined herein).

Suitable propellants include volatile hydrocarbons such as butane, propane, isobutene or mixtures thereof. In one or more embodiments a hydrocarbon mixture AP-70 is used. In one or more other embodiments a lower pressure hydrocarbon mixture AP-46 is used. Both contain butane, propane, isobutene although in different proportions. AP-70 is composed of about 50% w/w of propane, about 20% w/w of isobutane and about 30% w/w of propane. AP-46 is composed of about 16% w/w of propane, about 82% w/w of isobutane and about 2% w/w of propane Hydrofluorocarbon (HFC) propellants are also suitable as propellants in the context disclosed herein. Exemplary HFC propellants include 1,1,1,2 tetrafluorethane (Dymel 134), and 1,1,1,2,3,3,3 heptafluoropropane (Dymel 227). Dimethyl ether is also useful. In one or more embodiments use of compressed gases (e.g., air, carbon dioxide, nitrous oxide, and nitrogen) is also possible.

In one or more embodiments a combination of at least two propellants, selected from HFC, hydrocarbon propellants, dimethyl ether and compressed gases is contemplated.

Yet, in additional embodiments, the propellant is a self-foaming propellant, i.e., a volatile liquid having a boiling point of less than the temperature of the target treatment site (such as the skin). An example of a post-foaming propellant is isopentane (bp=26° C.)

Any concentration of the propellant, which affords an acceptable foam is useful in accordance with the present invention. In certain embodiments the propellant makes up between about 1% and about 30% of the foamable composition, or about 3% and 25%, preferably between about 5% and about 16% of the composition. In other certain embodiments, the concentration of the propellant is about 7% to about 17%; or about 10% to about 14% by weight of the total composition. The percent by weight is based on weight foamable composition. In preparing the formulations the ingredients other than propellant are combined to 100% and the propellant is added thereafter so that the ratio of formulation other than propellant to propellant can range from 100:1 to 100:30 or from about 100:3 to about 100:25; or from about 100:4 to about 100:24; or from about 100:7 to about 100:17; or from about 100:10 to about 100:14 or preferably 100:5 to 100:16. Yet, in additional embodiments, the ratio of composition other than propellant to propellant is between about 100:20 and about 100:50.

In one or more embodiments the propellant can also be used to expel formulation using a bag in can system or a can in can system as will be appreciated by someone skilled in the art. In certain embodiments the part of the propellant system is in the formulation and part separate from the formulation. In this way it is possible to reduce the amount of surfactant in the formulation but still provide good expulsion from the canister, where the foamable formulation is expelled quickly but without jetting or noise.

In one or more embodiments a foam formulation is expelled from a standard pressurized canister where the propellant is part of formulation. Formulations can be expelled or helped to be expelled by using propellant which is separate from the formulation using a bag in can or can in can system. Although, these systems can be used with compressed air the pressure may not be sufficient to expel the formulation through the device and higher pressure propellant such as AP70 should be selected. In one or more embodiments, the formulation is packaged in bag in can systems or in can in can system. In one or more embodiments, the formulation is expelled from the canister using the pressure provided by the propellant mixed with the formulation. In one or more embodiments, the formulation is expelled from the canister using the pressure provided by the propellant stored in a compartment surrounding the formulation. According to other embodiments part of the propellant system is in the formulation and part of the propellant system is separate from the formulation, which is used to expel said formulation using a bag or can in can system. In this way it is possible to reduce the amount of propellant within the formulation and avoid unwanted gaseous effects, for example in vaginal applications, but still provide good expulsion from the canister, where the foamable formulation is expelled sufficiently quickly but without jetting or noise. So by way of example, between about 1% to 3%; or between about 2% to 4%; between about 3% to 5% propellant (ratio of formulation to propellant of 100:1 to 3; 100:2 to 4; 100:3 to 5; respectively) is part of the formulation and a further amount of propellant is separate form the formulation and helps expel the formulation. In one or more embodiments a similar amount of propellant is in the formulation and a pump or other mechanical means is used to provide the additional expulsion force.

In one or more embodiments there is provided a composition comprising a propellant having a vapor pressure between about 10 psi and about 130 psi. In one or more embodiments there is provided a composition comprising a propellant which is hydrocarbon propellant or a hydrofluorocarbon or another environmentally acceptable propellant.

In an embodiment foam quality may be improved by increasing the propellant, by say aliqots of 2% or 4%, for example, from 8% to about 12%. The actual amount of propellant increase that is suitable should be titrated from formulation to formulation.

Stability Modulating Agent

In one or more embodiments a stability modulating agent is used in a waterless or substantially waterless composition. The term stability modulating agent is used to describe an agent which can improve the stability of, or stabilize a carrier or a foamable composition and/or an active agent by modulating the effect of a substance or residue present in the carrier or composition. The substance or residue may, for example, be acidic or basic or buffer system (or combinations thereof) and potentially alter an artificial pH in a waterless or substantially non-aqueous environment, such as, by acting to modulate the ionic or polar characteristics and any pH balance of a waterless or substantially non-aqueous carrier, composition, gel, foamable carrier or foamable composition or resultant foam or it may be a chelating or sequestering or complexing agent or it may be one or more metal ions which may act as a potential catalyst in a waterless or substantially non-aqueous environment or it may be an ionization agent or it may be an oxidizing agent.

Dermatologic Excipients

In one or more embodiments the formulation may comprise excipients that are suitable for dermatologic use. In one or more embodiments, the hydrophobic carrier composition further contains an anti-infective agent, selected from the group of an antibiotic agent, an antibacterial agent, an antifungal agent, an agent that controls yeast, an antiviral agent and an antiparasitic agent. In a preferred embodiment the anti infective agent comprises a tetracycline antibiotic. As has been previously shown in U.S. Provisional Application No. 61/248,144 filed Oct. 2, 2009 and titled "Surfactant-Free Water-Free Foamable Compositions, Breakable Foams And Their Uses," and in U.S. Provisional Application No. 61/322,148 filed Apr. 8, 2010 and titled "Surfactant-Free Water-Free Foamable Compositions, Breakable Foams And Gels And Their Uses," which are incorporated herein in their entirety by reference, combining the anti-infective effect of a hydrophobic carrier composition, with an anti-infective agent can result in a synergistic effect increasing the anti-infective effect and consequently higher success rate of the treatment is attained. According to the present application it has surprisingly been shown that combination of an active agent with second rheology modulator achieves a viscous formulation in which the active pharmaceutical ingredient is chemically stable and the formulation is physically stable as demonstrated herein in the Examples. Moreover the use of hydrophobic based water free formulation has been previously shown in said provisional application to maximize the antimicrobial potential of the formulations. Storage in sealed, light and airtight canisters can assist in preserving the formulations.

Ophthalmic Excipients

In one or more embodiments the formulation may comprise excipients that are suitable for ophthalmic use. By virtue of their suitability for ophthalmic use they may in certain embodiments be applicable on other sensitive targets such as for use internal and/or external wounds or burns or in body cavities. Excipients selected as part of a drug carrier that can be used with the active pharmaceutical ingredients are identified by compatibility studies with active ingredients to ascertain which are compatible for use with the active pharmaceutical agents, for example, by examining which do not react with and/or promote break down of the active pharmaceutical ingredients. Oleaginous ointments are viscous preparations, which remain viscous when applied to the skin or other body surfaces; and they require extensive rubbing. Because of their viscosity, eye ointments cause blurred vision and consequent low tolerability, especially for long term treatment. Because of their high viscosity, drugs are trapped in the vehicle and cannot migrate through to their target site of action, for example, the skin or the eye.

Liquid, non viscous oleaginous medications are also disadvantageous, as they spill easily and thus, are very inconvenient to use. In eye treatment, liquid drops are difficult to apply and they require lying on the back at rest for accurate administration. Furthermore, because of their low viscosity, liquid oil vehicles cannot carry suspended drugs, which tend to precipitate and if the viscosity is not high enough, thereby impairing the uniformity of the therapeutic product.

In one or more embodiments the formulations are not highly viscous; and they may be flowable. In one or more embodiments the formulations are thixotropic so that on application of shear force their viscosity decreases and they become more flowable. In one or more embodiments the formulations are foams which are breakable on shear force. In one or more embodiments the foams are based on gel formulations, which are thixotropic so that on application of shear force their viscosity decreases and they become more flowable. In one or more embodiments the viscosity of the formulation prior to addition of propellant is more than about 1000 cPs and less than about 25,000 cPs.

Additional Components

In an embodiment, a composition disclosed herein includes one or more additional components. Such additional components include but are not limited to anti perspirants, anti-static agents, bulking agents, cleansers, colorants, skin conditioners, deodorants, diluents, dyes, fragrances, hair conditioners, herbal extracts, humectants, keratolytic agents, modulating agents, pearlescent aids, perfuming agents, pH modifying or stabilizing agents, skin penetration or permeation enhancers, softeners, solubilizers, sunscreens, sun blocking agents, sunless tanning agents, viscosity modifiers, flavanoids and vitamins. As is known to one skilled in the art, in some instances a specific additional component may have more than one activity, function or effect.

In certain embodiments, the additional component is an oil soluble preservative, or an oil soluble antioxidant, or an oil soluble radical scavenger, or an oil soluble complexing agent, or an oil soluble pigment or dye.

Definitions

All % values are provided on a weight (w/w) basis.

By the term "about" herein it is meant as indicated above and that a figure or range of figures can vary in an embodiments plus or minus up to 30%. So in this embodiment if a figure of "about 1" is provided then the amount can be up to 1.3 or from 0.70. In other embodiments it can reflect a variation of plus or minus 20%. In still further embodiments it can describe a variation of plus or minus 10%. In still further embodiments it can describe a variation of plus or minus 5%. As will be appreciated by one of the art there is some reasonable flexibility in formulating compositions such that where one or more ingredients are varied successful formulations may still be made even if an amount falls slightly outside the range. Therefore, to allow for this possibility amounts are qualified by about. In one or more other embodiments the figures may be read without the prefix about.

The term "thixotropic," as used herein, means that the formulation shows a significant decrease in viscosity upon application of shear force.

The term "waterless," as used herein, means that the composition contains no, or substantially no, free or unassociated or absorbed water. Similarly, "waterless" or "substantially waterless" carriers contain at most incidental and trace amounts of water.

By the term "single phase" herein it is meant that the liquid components of the composition or carrier are fully miscible, and the solid components if any, are either dissolved or suspended in the composition. By substantially a single phase is meant that the composition or carrier is primarily or essentially a single phase as explained above, but may also have present a small amount of material which is capable of forming or may form a separate phase amounting to less than about 5% of the composition or carrier, preferably less than about 3%, and more preferably less than about 1%. By the term "single phase" or "substantially a single phase" in the context of a foamable composition the above meaning applies even after addition of propellant to the composition or carrier.

The term "unstable active agent" as used herein, means an active agent which is oxidized and/or degraded within less than a day, and in some cases, in less than an hour upon exposure to air, light, skin or water under ambient conditions.

The term "co-surfactant" as used herein, means a molecule which on its own is not able to form and stabilize satisfactorily an oil in water emulsion but when used in combination with a surfactant the co-surfactant has properties, which can allow it to help surfactants to create an emulsion and can boost the stabilizing power or effect of the surfactant and can include, for example, a fatty alcohol, such as cetyl alcohol or a fatty acid such as stearic acid. Cetyl alcohol is a waxy hydrophobic substance that can be emulsified with water using a surfactant. Some substances may have more than one function and for example, fatty alcohols can in some formulations act as a co-solvent. In certain circumstances a co-surfactant can itself be converted in to a surfactant or soap by, for example, adding a base, such as, triethanolamine to a fatty acid like stearic acid.

The identification of a "polyol", as used herein, is an organic substance that contains at least two hydroxy groups in its molecular structure.

In one or more embodiments, the polyol is a diol (a compound that contains two hydroxy groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2,56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the polyol is a triol (a compound that contains three hydroxy groups in its molecular structure), such as glycerin, butane-1,2,3-triol, butane-1,2,4-triol and hexane-1,2,6-triol.

In one or more embodiments, the polyol is a saccharide. Exemplary saccharides include, but are not limited to monosaccharide, disaccharides, oligosaccharides and sugar alcohols.

A monosaccharide is a simple sugar that cannot be hydrolysed to smaller units. Empirical formula is $(CH_2O)_n$ and range in size from trioses (n=3) to heptoses (n=7). Exemplary monosaccharide compounds are ribose, glucose, fructose and galactose.

Disaccharides are made up of two monosaccharides joined together, such as sucrose, maltose and lactose.

In one or more embodiments, the polyol is a sugar alcohol (also known as a polyol, polyhydric alcohol, or polyalcohol) is a hydrogenated form of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present application are mannitol, sorbitol, xylitol, maltitol, lactitol. (Maltitol and lactitol are not completely hydrogenated compounds—they are a monosaccharide combined with a polyhydric alcohol.) Mixtures of polyols, including (1) at least one polyol selected from a diol and a triol; and (2) a saccharide are contemplated within the scope of the present disclosure.

According to some embodiments, the composition is polyol free i.e., free of polyols. In other embodiments, the composition is substantially free and comprises less than about 5% final concentration of polyols, preferably less than 2%, more preferably less than 1%. Where a formulation includes insignificant amounts of polyols it is considered to be essentially free of them.

In an embodiment, the polyol is linked to a hydrophobic moiety. In the context of the present disclosure, a polyol linked to a hydrophobic moiety is still defined as a "polyol" as long as it still contains two or more free hydroxyl groups.

In an embodiment, the polyol is linked to a hydrophilic moiety. In the context of the present disclosure, a polyol linked to a hydrophilic moiety is still defined "polyol" as long as it still contains two or more free hydroxyl groups.

The term "water activity" as used herein, activity represents the hydroscopic nature of a substance; or the tendency of a substance that absorbs water from its surroundings. Microorganisms require water to grow and reproduce, and such water requirements are best defined in terms of water activity of the substrate. The water activity of a solution is expressed as $Aw=P/Po$, where P is the water vapor pressure of the solution and Po is the vapor pressure of pure water at the same temperature. Every microorganism has a limiting Aw, below which it will not grow; e.g., for *Streptococci, Klebsiella* spp, *Escherichia coli, Clostridium perfringens*, and *Pseudomonas* spp, the Aw value is 0.95. *Staphylococcus aureus* is most resistant and can proliferate with an Aw as low as 0.86, and fungi can survive at Aw of at least 0.7. In one or more embodiments, the concentration of the hydrophobic solvent, and/or second rheology modulator in the composition is selected to provide an Aw value selected from the ranges of (1) about 0.8 and about 0.9; (2) about 0.7 and about 0.8; and (3) less than about 0.7. By delivering the formulation in a pressurized package does not allow for humidity to be absorbed by the preparation, and therefore, the water free character of the composition cannot be damaged.

In an embodiment no preservative is added because the formulation is a waterless hydrophobic solvent or oil-based formulation having an Aw (Water Activity) value of less than 0.9, less, or less than about 0.8, or less than about 0.7 or less than about 0.6 and preferably less than about 0.5 which is below the level of microbial proliferation.

The identification of a "solvent," as used herein, is not intended to characterize the solubilization capabilities of the solvent for any specific active agent or any other component of the composition. Rather, such information is provided to aid in the identification of materials suitable for use as a part in the carriers described herein.

Substantially Alcohol Free

Lower or short chain alcohols, having up to 5 carbon atoms in their carbon chain skeleton, such as ethanol, propanol, isopropanol, butanol, iso-butanol, t-butanol and pentanol are considered less desirable solvents or co-solvents due to their skin-irritating effect. Thus, according to some embodiments, the composition is substantially alcohol-free i.e., free of short chain alcohols. In other embodiments, the composition comprises less than about 5% final concentration of lower alcohols, preferably less than 2%, more preferably less than 1%. Where a formulation contains insignificant amounts of short chain alcohols it is considered to be essentially free of them.

Substantially Standard Surfactant Free

Surfactants have been categorized in to various sub classes depending on there ionic characteristics, namely non-ionic surfactants, anionic, cationic, zwitterionic, amphoteric and amphiphilic surfactants. The term surfactant has been often loosely used in the art to include substances which do not function effectively as stand alone surfactants to reduce surface tension between two substances or phases. Reduction of surface tension can be significant in foam technology in relation to the ability to create small stable bubbles. For example fatty alcohols, fatty acids and certain waxes are amphiphatic, are essentially hydrophobic with a minor hydrophilic region and for the purposes of forming an emulsion unlike standard or customary surfactants, are not effective as stand-alone surfactants in foamable emulsion compositions, because of their very weak emulsifying capacity on their own. They are occasionally used in a supporting role as co-emulsifiers, i.e., in combination with a standard surfactant but are commonly used as thickeners and have successfully been used as foam adjuvants to assist customary surfactants to boost foam quality and stability. For clarification in the context herein whilst the term "standard surfactant" or "customary surfactant" refers herein to customary non-ionic, anionic, cationic, zwitterionic, amphoteric and amphiphilic surfactants a fatty alcohol or a fatty acid and certain waxes are not regarded as a standard surfactant. However, in contrast, an ether or an ester formed from such fatty alcohols or fatty acids can be regarded as a customary surfactant. Many standard surfactants are, derivatives of fatty alcohols or fatty acids, such as an ethers or an esters formed from such fatty alcohols or fatty acids with hydrophilic moieties, such as polyethyleneglycol (PEG) can be regarded as a customary surfactant. However, a native, (non derivatized) fatty alcohols or a fatty acids, or as well as waxes are not regarded as a standard surfactant.

Generally, surfactants are known to possess irritation potential. One way that is used to try and reduce potential irritation and drying of the skin or mucosa due to surfactants and their repeated use especially when formulations are to be left on the skin or mucosa rather than being washed off is to use essentially or primarily non ionic surfactants at preferably low concentrations below 5%. The current breakthrough of identifying formulations which produce quality breakable foam yet omitting customary surfactants from a composition may contribute to improved tolerability of such a composition and can be an important advantage. This is especially so when a formulation is to be applied to a very sensitive target site, and particularly so on a repeated basis.

Non-limiting examples of classes of customary non-ionic surfactants include: (i) polyoxyethylene sorbitan esters (polysorbates), such as polysorbate 20, polysorbate 40, polysorbate 60 and polysorbate 80; (ii) sorbitan esters, such as sorbitan monostearate sorbitan monolaurate and sorbitan monooleate; (iii) polyoxyethylene fatty acid esters, such as PEG-8 stearate, PEG-20 stearate, PEG-40 stearate, PEG-100 stearate, PEG-8 laurate, PEG-10 laurate, PEG-12 laurate, PEG-20 laurate, PEG-8 oleate, PEG-9 oleate, PEG-10 oleate, PEG-12 oleate, PEG-15 oleate and PEG-20 oleate; (iv) PEG-fatty acid diesters, such as PEG-150 distearate; (v) polyethylene glycol (PEG) ethers of fatty alcohols; (vi) glycerol esters, such as glyceryl monostearate, glyceryl monolaurate, glyceryl monopalmitate and glyceryl monooleate; (vii) PEG-fatty acid mono- and di-ester mixtures; (viii) polyethylene glycol glycerol fatty acid esters; (ix) propylene glycol fatty acid esters; (x) mono- and diglycerides; (xi) sugar esters (mono-, di- and tri-esters of sucrose with fatty acids) and (xii) polyethylene glycol alkyl phenols.

In certain embodiments, the composition is free of customary surfactants, or "surfactant-free" and in certain embodiments the foamable composition is substantially free of customary surfactants, or "substantially surfactant-free". In certain alternative embodiments, the composition comprises a surfactant.

In the context herein, the term "substantially surfactant-free composition" relates to a composition that contains a total of less than about 0.4% of a surfactant selected from the group consisting of customary non-ionic, anionic, cationic, zwitterionic, amphoteric and ampholytic surfactants. Preferably, the composition comprises less than about 0.2% by weight of a standard surfactant and more preferably less than about 0.1%. Where a formulation includes insignificant amounts of surfactants it is considered to be essentially free of them. Non-surfactant or surfactant-free compositions will comprise no or negligible levels of surface active agents.

In additional embodiments, the term "substantially surfactant-free" relates to a composition wherein the ratio between the foamer complex and the surfactant is between 10:1 or 5:1; or between 20:1 and 10:1 or between 100:1 and 20:1.

In certain embodiments, the composition is free or substantially free of an ionic surfactant. In certain embodiments, the composition is free or substantially free of a non-ionic surfactant.

Substantially Polymer Free

By the term polymeric agent it is intended to mean a compound having multiple repeated units such as cellulose polymers, acrylic polymers, block polymers and copolymers. In one or more certain embodiments the polymeric agent has a molecular weight of in excess of a 1000 Daltons. Unexpectedly, it has been discovered that quality oleaginous formulations and foams can be achieved without the presence of significant amounts of standard polymeric agents known in the art (e.g. gelling agents). Thus, in one or more embodiments, there is provided a substantially surfactant free and substantially polymeric agent free oleaginous formulation or foam. In one or more preferred embodiments the oleaginous formulations and foams are free of surface active agents and polymers. Unexpectedly, it has further been discovered that quality oleaginous formulations and foams can be achieved without the presence of significant amounts of standard surfactants, foam adjuvants and polymeric agents known in the art. Thus, in one or more embodiments, there is provided a substantially surfactant free and substantially polymeric agent free oleaginous formulation or foam. In one or more preferred embodiments the oleaginous formulations and foams are free of surface active agents and polymeric agents.

By the term polymeric agent it is intended to mean a compound having multiple repeated units such as cellulose polymers, acrylic polymers, block polymers and copolymers. In one or more embodiments the number of multiple or repeating units is at least 4. In one or more embodiments the oleagonious formulations are substantially polymer free. In one or more embodiments the oleagonious formulations are substantially polymer free of a polymeric agent selected from the group consisting of a bioadhesive agent, a gelling agent, a film forming agent and a phase change agent, being locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers, semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses, carbomer (homopolymer of acrylic acid is crosslinked with an allyl ether pentaerythritol, an allyl ether of sucrose, or an allyl ether of propylene); poloxamers (synthetic block copolymer of ethylene oxide and propylene); polyethylene glycol having molecular weight of 1000 or more (e.g., PEG 1,000, PEG 4,000, PEG 6,000 and PEG 10,000) and which could function as a hydro alcoholic foam booster. By substantially polymer free it is intended to mean less than about 5%, preferably less than about 2%. By essentially polymer free it is intended to mean less than about 1%, preferably less than about 0.5%. In further embodiments they are essentially polymer free and in still further embodiments they are free of polymeric agents. In alternative embodiments the oleaginous formulations may comprise a polymeric agent in such case the polymeric agents are oil soluble polymeric agents. Non limiting examples of oil-soluble polymeric agents are: Ethyl cellulose, alkylated guar gum, trimethylsiloxysilicate, alkyl-modified silicone, polyamide-modified silicone, homopolymers and copolymers of alkyl methacrylates, alkyl acrylates, and alkyl styrenes, polyisobutene, polybutyl metacrylate, polycyclohexylstyrene.

According to one or more embodiments, the composition comprises less than about 0.1% by weight of a polymeric agent and more preferably less than about 0.05%. Polymer free compositions will comprise no or negligible levels of polymeric agents.

In the art, the term polymeric agent can be used loosely to refer to any polymer. However, in some embodiments polymers that do not have a gel building role but may act in other ways are not excluded from the compositions. In one or more embodiments a polyether siloxane copolymer and a poly(dimethylsiloxane)-(diphenyl-siloxane) copolymer and the like, which can provide a good feeling to the composition are not excluded.

Physical Characteristics of the Gels and Foamable Composition and Foam

A composition manufactured according to one or more embodiments herein is very easy to use. When applied onto the afflicted body surface of mammals, i.e., humans or animals, it is in a gel or foam state, allowing free application without spillage. Upon further application of a mechanical force, e.g., by rubbing the composition onto the body surface, it freely spreads on the surface and is rapidly absorbed.

In one or more embodiments the composition is a single phase solution. In one or more embodiments the composition is substantially a single phase solution. In certain circumstances, where the active agent is insoluble and is presented as a homogenous suspension, the formulation is turbid or cloudy.

In one or more embodiments the composition has an acceptable shelf-life of at least one year, or at least two years at ambient temperature. A feature of a product for cosmetic or medical use is long term stability. Propellants, which are a mixture of low molecular weight hydrocarbons, tend to impair the stability. The foamable compositions herein are surprisingly stable, even in the absence of customary surfactants. Following accelerated stability studies, they demonstrate desirable texture; they form fine bubble structures that do not break immediately upon contact with a surface, spread easily on the treated area and absorb quickly.

In certain embodiments the composition should also be free flowing, to allow it to flow through the aperture of the container, e.g., gel tube or an aerosol container, and provide an acceptable gel or foam. Compositions containing a substantial amount of semi-solid hydrophobic solvents, e.g., white petrolatum, as the main ingredients of the oil phase of the emulsion, will likely exhibit high viscosity and poor flowability and can be inappropriate candidates for a foamable composition. Thus in one or more embodiments semi-solid hydrophobic solvents are a subsidiary component in the composition, for example being present at less than about 25%, less than about 20%, less than about 15%, less than about 10%, or less than about 5% by weight of the foamable composition. In other embodiments they can be present in higher amounts due to the solvent effect e.g of a liquid solvent or of the propellant diluting the formulation and enabling flowability or where the formulation is presented as a gel or ointment.

Foam Quality

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of a more stable foam, which does not collapse spontaneously immediately upon discharge from the container. The finer foam structure looks and feels smoother, thus increasing its usability and appeal.

Foam Density

Another property of the foam is specific gravity or density, as measured upon release from the aerosol can. Typically, foams have specific gravity of less than 0.50 g/mL or less than 0.12 g/mL, depending on their composition and on the propellant concentration. In one or more embodiments the foam density is about less than 0.3 g/mL.

Shakability

'Shakability' means that the composition contains some or sufficient flow to allow the composition to be mixed or remixed on shaking. That is, it has fluid or semi fluid properties. Shakability is described further in the section on Tests. In one or more certain limited embodiments the formulation is poorly shakable but is nevertheless flowable.

Breakability/Collapse Time

A further optional aspect of the gel or foam is breakability. The balance between stability and breakability of the gel or foam coming out of the container is very delicate: on one hand the gel or foam may not be "quick breaking", i.e., it should be stable upon release from the pressurized container and not break as a result of exposure to skin temperature; and on the other hand, it should be "breakable", i.e., it should spread easily, break down and absorb into the skin or membrane upon application of mild shear force. The breakable gel or foam is thermally stable, yet breaks under shear force. Shear-force breakability of the gel or foam is clearly advantageous over thermally-induced breakability. Thermally sensitive gels or foams start to collapse immediately upon exposure to skin temperature and, therefore, cannot be applied on the hand and afterwards delivered to the afflicted area.

The collapse time of a gel or foam represents its tendency to be temperature-sensitive and its ability to be at least stable in the short term so as to allow a user sufficient time to comfortably handle and apply the gel or foam to a target area without being rushed and/or concerned that it may rapidly collapse, liquefy and/or disappear. Collapse time, as an indicator of thermal sensitivity, is examined by dispensing a given quantity of gel or foam and photographing sequentially its appearance with time during incubation at 36° C. Simple collapse time can be measured by applying a gel or foam sample on a body surface like the fingers at normal body temperature of about 37° C.

Oils may cause foam to be thermolabile and "quick breaking." However, in certain embodiments herein, despite the presence of high oil content, quite unexpectedly the foam is substantially thermally stable. By "substantially thermally stable" it is meant that the foam upon application onto a warm skin or body surface at about 35-37° C. does not collapse within about 30 seconds. Thus, in one or more embodiments the simple collapse time of the foam is more than about 30 seconds or more than about one minute or more than about two minutes. In one or more limited embodiments simple collapse time can be a little shorter than 30 seconds, but not less than about 20 seconds. In one or further or alternative embodiments the collapse time is measured by introducing a sample of foam into an incubator at 36° C. and the collapse time of the foam is more than 30 seconds or more than about one minute or more than about two minutes.

There are many applications for a gel or foam of the present invention. Below is a non-limiting list of applications which are provided to demonstrate the versatility of such a composition and method for modulating an oleogenous formulation viscosity. While many of such applications are in the healthcare and cosmetic area, adding a rheology modulator to waxes in olegeneous compositions can be extended to applications outside the pharmaceutical and cosmetic fields, including for example mechanics, electronics, food industry, safety, sanitation etc.

Pharmaceutical Composition

The oleaginous composition of the present invention can be used by itself as a topical treatment of a body surface, as many hydrophobic solvents such as emollients, unsaturated oils, essential oils or therapeutic oils that possess cosmetic or medical beneficial effects. Furthermore, it is an ideal vehicle for active pharmaceutical ingredients and active cosmetic ingredients. In the context active pharmaceutical ingredients and active cosmetic ingredients are collectively termed "active agent" or "active agents". The absence of surfactants in the composition is especially advantageous, since no surfactant-related adverse reactions are expected from such a composition. Some surfactants may act to facilitate gelling of the pre-foam formulation. In one or more embodiments the active agent is soluble in the composition of a phase thereof. In one or more other embodiments it is partially soluble or insoluble. When partially soluble or insoluble the active agent is presented as a suspension or it can be encapsulated in a carrier. In one or more embodiments the active agent is a rheology modifying active agent. In one or more embodiments the active agent is a non rheology modifying active agent. In one or more embodiments a rheology modifying active agent and a non rheology modifying active agent can be used in combination.

Suitable active agents include but are not limited to an active herbal extract, an acaricides, an age spot and keratose removing agent, an allergen, an alpha hydroxyl acid, an analgesic agent, an androgen, an antiacne agent, an antiallergic agent, an antiaging agent, an antibacterial agent, an antibiotic, an antiburn agent, an anticancer agent, an antidandruff agent, an antidepressant, an antidermatitis agent, an antiedemic anent, an antifungal agent, an antihistamine, an antihelminth agent, an anti-hyperkeratosis agent, an anti-infective agent, an antiinflammatory agent, an antiirritant, an antilipemic agent, an antimicrobial agent, an antimycotic agent, an antioxidant, an antiparasitic agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an anti-yeast agent, an astringent, a beta-hydroxy acid, benzoyl peroxide, a cardiovascular agent, a chemotherapeutic agent, a corticosteroid, an immunogenic substance, a dicarboxylic acid, a disinfectant, an estrogen, a fungicide, a hair growth regulator, a haptene, a hormone, a hydroxy acid, an immunosuppressant, an immunoregulating agent, an immunomodulator, an immunostimulant, an insecticide, an insect repellent, a keratolytic agent, a lactam, a local anesthetic agent, a lubricating agent, a masking agent, a metal, a metal oxide, a mitocide, a neuropeptide, a non-steroidal anti-inflammatory agent, an oxidizing agent, a pediculicide, a peptide, a pesticide, a progesterone, a protein, a photodynamic therapy agent, a radical scavenger, a refatting agent, a retinoid, a sedative agent, a scabicide, a self tanning agent, a skin protective agent, a skin whitening agent, a steroid, a steroid hormone, a vasoactive agent, a vasoconstrictor, a vasodilator, a vitamin, a vitamin A, a vitamin A derivative, a vitamin B, a vitamin B derivative, a vitamin C, a vitamin C derivative, a vitamin D, a vitamin D derivative, a vitamin D analog, a vitamin F, a vitamin F derivative, a vitamin K, a vitamin K derivative, a wound healing agent and a wart remover. According to a further embodiment the active agent is a tetracycline antibiotic. In certain embodiments the tetracycline is minocycline. In certain embodiments the tetracycline is doxycycline. In certain embodiments the agent is selected from a group consisting of calcitriol, mometasone fuorate, calcitriol and lidocaine. As is known to one skilled in the art, in some instances a specific active agent may have more than one activity, function or effect. According to a further embodiment the active agent is chemically stable for at least two months and where the active agent is compatible with the other ingredients. According to a further embodiment the active agent is chemically stable for at least six months; or for at least nine months for at least twelve months; or for at least fifteen months; or for at least eighteen months; or for at least twenty one months; or for at least twenty four months.

Encapsulation of an Active Agent

In one or more embodiments, the active agent is encapsulated in particles, microparticles, nanoparticles, microcapsules, microspheres, nanocapsules, nanospheres, liposomes, niosomes, polymer matrix, silica-gel, graphite, nanocrystals or microsponges. Such particles can have various functions, such as (1) protection of the drug from degradation; (2) modification of the drug release rate from the composition; (3) control of skin penetration profile; and (4) mitigation of adverse effects, due to the controlled release of the active agent from the encapsulation particles.

Solubility of an Active Agent

Solubility of the steroid is an important factor in the development of a stable composition according to the present invention.

For definition purposes, in the context of the present invention, the descriptive terminology for solubility according to the US Pharmacopoeia (USP 23, 1995, p. 10), the European Pharmacopoeia (EP, $5^{th}$ Edition (2004), page 7) and several other textbooks used in the art of pharmaceutical sciences (see for example, Martindale, The Extra Pharmacopoeia, $30^{th}$ Edition (1993), page xiv of the Preface; and Remington's Pharmaceutical Sciences, $18^{th}$ Edition (1990), page 208) is adapted:

| Descriptive Term | Parts of Solvent Required for 1 Part of Solute |
|---|---|
| Very soluble | Less than 1 |
| Freely soluble | From 1 to 10 |
| Soluble | From 10 to 30 |
| Sparingly soluble | From 30 to 100 |
| Slightly soluble | From 100 to 1,000 |
| Very slightly soluble | From 1,000 to 10,000 |
| Practically insoluble or Insoluble | 10,000 and over |

In preferred embodiments of the present invention, the active agent, which constitutes the first rheology modulator is not soluble or is partially soluble and all or part thereof, is suspended in the composition. Thus, in one or more embodiments, the active agent is present in the composition in a concentration which is higher than prescribed in the above table for such an active agent.

Yet, in one or more embodiments, the active agent is insoluble i.e., "requires 10,000 parts or more of a solvent to be solubilized", in the composition.

In certain embodiments it is desirable that the active agent is maximally soluble in the composition, because solubility of the active agents is expected to increase its bioavailability.

Yet, in additional embodiments it is desirable that the active agent is insoluble in the composition, because its degradation is enhanced when it is dissolved. In such cases, the hydrophobic solvent is selected by (1) testing the solubility of said active agent in various hydrophobic solvents, followed by (2) inclusion in the composition of such solvents that do not solubilize the active agent. In one or more embodiments the active agent is presented as a suspension. In one or more further embodiments the active agent is micronized, which can assist in delivery into the skin, mucosal membrane and body cavity surfaces and also aid homogenous distribution within the formulation. In effect, part of the active agent is presented to a target in soluble form and part is presented in insoluble form. As the soluble part is absorbed it may help to form a gradient in which insoluble agent replaces absorbed agent. In one or more embodiments insoluble agent is suspended. In one or more embodiments the suspension is homogenous. In certain embodiments the formulation is readily resuspended and homogenous on shaking. In certain embodiments the agent is soluble.

Exemplary Groups of Active Agents

Active agents, which constitute the first viscosity modulators are not soluble or are partially soluble and all or part thereof is suspended in the composition. It is known that every chemical compound has different solubility in different solvents or compositions, and therefore it is not possible to provide a general list compounds that fulfill such a distinction. However, an active agent, as exemplified in the lists below, is suitable as a first viscosity modulator according to the present invention if it is not soluble or is partially soluble or is suspended in the oleaginous composition.

Antibiotics

In the context of the present disclosure, an antibiotic agent is a substance, that has the capacity to inhibit the growth of or to destroy bacteria and other microorganisms.

In one or more embodiments, the antibiotic agent is selected from the classes consisting beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinolones, antibiotic steroides, sulfonamides, tetracycline, dicarboxylic acids, antibiotic metals including antibiotic metal ions, oxidizing agents, a periodate, a hypochlorite, a permanganate, substances that release free radicals and/or active oxygen, cationic antimicrobial agents, quaternary ammonium compounds, biguanides, triguanides, bisbiguanides and analogs and polymers thereof, naturally occurring antibiotic compounds, including antibiotic plant oils and antibiotic plant extracts and any one of the following antibiotic compounds including non classified antibiotic compound analogs, derivatives, salts, ions, complexes and mixtures thereof.

Tetracyclines

According to some embodiments, the antibiotic agent is a tetracycline. The tetracyclines (also referred to herein as "tetracycline antibiotics") are a group of antibacterials, originally derived from certain *Streptomyces* spp., having the same tetracyclic nucleus, naphthacene, and similar properties. They are usually bacteriostatic but act by interfering with protein synthesis in susceptible organisms. Tetracycline antibiotics are susceptible to degradation by oxidation.

Tetracyclines include, but are not limited to, dihydrosteffimycin, demethyltetracycline, aclacinomycin, akrobomycin, baumycin, bromotetracycline, cetocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Chlortetracycline, oxytetracycline, tetracycline, demeclocycline are all natural products that have been isolated from *Streptomyces* spp. The more recent tetracyclines, namely methacycline, doxycycline, and minocycline, are semisynthetic derivatives. Methacycline, like demeclocycline, has a longer half-life than tetracycline.

Tetracyclines are typically insoluble or partially soluble in many hydrophobic solvents.

Minocycline

Minocycline is active against some tetracycline-resistant bacteria, including strains of staphylococci. Both doxycycline and minocycline are more lipid-soluble than the other tetracyclines and they penetrate well into tissues. They are thus more suitable for incorporating into oily or emollient containing formulations. However, they have a place in the treatment of chlamydial infections, rickettsial infections such as typhus and the spotted fevers, mycoplasmal infections such as atypical pneumonia, pelvic inflammatory disease, Lyme disease, brucellosis, tularaemia, plague, cholera, periodontal disease, and acne. The tetracyclines have also been useful in the treatment of penicillin-allergic patients suffering from venereal diseases, actinomycosis, bronchitis, and leptospirosis. Minocycline may sometimes be used in multidrug regimens for leprosy. Doxycycline may be used for the treatment and prophylaxis of malaria; it is also used in the management of anthrax.

In an embodiment the active ingredient may be any one of the following non limiting examples chlortetracycline, demeclocycline, doxycycline, lymecycline, meclocycline, methacycline, minocycline, oxytetracycline, rolitetracycline, tetracycline. In a preferred embodiment they are doxycyline or minocycline.

Tetracycline antibiotics can be incorporated into the formulations of the present invention to treat, ameliorate or prevent a multitude of disorders responsive to tetracycline antibiotics. The formulations can be applied topically to the skin or to the genitals or to mucosal membranes and on and around the eye, sub-gingival and can be applied into a wide range of body cavities, including aural, digestive, oral, nasal, urethra, penal, endocervical, rectum, respiratory, and vaginal and tooth pocket. Non limiting examples of applications include eye infections, blepharitis, dry eye, inclusion conjunctivitis, glaucoma, inflammatory ocular conditions where bacterial infection or a risk of bacterial ocular infection exists, neuropathic atrophy (in diabetes), abrasions, injuries, wounds, burns, ulcers, pyoderma, furunculosis, granuloma inguinale, periodontitis, rosacea, post-operation infections and tissue reconstruction, trachoma, lymphogranuloma venereum, granuloma inquinale, acne, inflammation, sinusitis, neuro-protection, washing out, disinfection, and stabilization of body cavities, at on around or in the site of an operation, which for example can provide multiple therapeutic effects, such as, inhibition of post operation adhesions, anti infection, neuro-protection.

Whether delivered as a foam, gel, ointment or suspension the active pharmaceutical tetracycline can be present by weight in the range of about 0.01% to about 20%, about 0.2% to about 20%, or at about 0.01%, at about 0.1%, at about 0.2%, at about 0.3%, at about 0.4%, at about 0.5%, at about 0.6%, at about 0.7%, at about 0.8%, at about 0.9%, at about 1%, at about 1.5%, at about 2%, at about 2.5%, at about 3%, at about 3.5% at about 4%, at about 4.5%, at about 5%, at about 6%, at about 7%, at about 8%, at about 9%, at about 10%, at about 12%, or at about 14%, at about 16%, at about 18%, or at about 20%.

Tetracyclines and Skin Infections

Tetracyclines have been used in ophthalmic ointments for the prevention or treatment of infections of the eye caused by susceptible bacteria. Although minor skin infections and wounds usually heal without treatment, some minor skin wounds do not heal without therapy and it is impossible to determine at the time of injury which wounds will be self-healing. Therefore, some experts believe that, by reducing the number of superficial bacteria, topical anti-infectives are useful for preventing infection in minor skin injuries (e.g., cuts, scrapes, burns).

Tetracycline hydrochloride may be used topically in the prevention or treatment of inflammatory acne vulgaris. Tetracyclines are usually bacteriostatic in action, but may be bactericidal in high concentrations or against highly susceptible organisms.

Tetracyclines appear to inhibit protein synthesis in susceptible organisms primarily by reversibly binding to 30S ribosomal subunits, thereby inhibiting binding of aminoacyl transfer-RNA to those ribosomes. In addition, tetracyclines appear to reversibly bind to 50S ribosomal subunits. There is preliminary evidence that tetracyclines also alter cytoplasmic membranes of susceptible organisms resulting in leakage of nucleotides and other intracellular components from the cell. At high concentrations, tetracyclines also inhibit mammalian protein synthesis.

The exact mechanisms by which tetracyclines reduce lesions of acne vulgaris have not been fully elucidated; however, the effect appears to be partly the result of the antibacterial activity of the drugs. Following topical application to the skin of a 0.22% solution of tetracycline hydrochloride in a vehicle containing n-decyl methyl sulfoxide (Topicycline®; no longer commercially available in the US), the drug inhibits the growth of susceptible organisms (principally Propionibacterium acnes) on the surface of the skin and reduces the concentration of free fatty acids in sebum. The reduction in free fatty acids in sebum may be an indirect result of the inhibition of lipase-producing organisms which convert triglycerides into free fatty acids or may be a direct result of interference with lipase production in these organisms. Free fatty acids are comedogenic and are believed to be a possible cause of the inflammatory lesions (e.g., papules, pustules, nodules, cysts) of acne. However, other mechanisms also appear to be involved because clinical improvement of acne vulgaris with topical tetracyclines does not necessarily correspond with a reduction in the bacterial flora of the skin or a decrease in the free fatty acid content of sebum. (Martindale Electronic Version 2007).

Tetracyclines, Solubility and Stability

Tetracyclines are known to be unstable in the presence of water, as well as numerous types of formulation excipients, such as protic solvents, various surfactants and certain oils. It was surprisingly discovered in U.S. Provisional Application No. 61/248,144 filed Oct. 2, 2009 and titled "Surfactant-Free Water-Free Foamable Compositions, Breakable Foams And Their Uses," and to U.S. Provisional Application No. 61/322,148 filed Apr. 8, 2010 and titled "Surfactant-Free Water-Free Foamable Compositions, Breakable Foams And Gels And Their Uses," that the inclusion of tetracyclines in a composition comprising a hydrophobic solvent and a foamer complex described therein results in a stable product, with extended stability of the tetracycline. In an embodiment a hydrophobic solvent is selected by (1) testing the solubility of said active agent in various hydrophobic solvents, (2) identifying those that do not solubilize the active agent followed by (3) inclusion in the composition of such solvents that do not solubilize the active agent. In preferred embodiments the tetracycline is insoluble in the composition.

Doxycyline

According to some embodiments, the tetracycline is doxycycline. Doxycycline is a tetracycline antibiotic and also has anti-inflammatory and immunomodulatory effects. Doxycycline is a semisynthetic tetracycline antibiotic derived from oxytetracycline. In addition to antimicrobial activity, the drug has anti-inflammatory and immunomodulatory effects. It is available as Doxycycline calcium, doxycycline hyclate and doxycycline monohydrate. Doxycycline hyclate and doxycycline monohydrate occur as yellow, crystalline powders. The hyclate is soluble in water and slightly soluble in alcohol; the monohydrate is very slightly soluble in water and sparingly soluble in alcohol. Doxycycline calcium is formed in situ during the manufacturing process. Following reconstitution of doxycycline hyclate powder for IV administration with sterile water for injection, solutions have a pH of 1.8-3.3.

The mechanism(s) by which doxycycline reduces inflammatory lesions (papules and pustules) in patients has not been elucidated, but these effects may result at least in part from the anti-inflammatory actions of the drug; other mechanisms may be involved Doxycycline is used for the treatment of rosacea treatment or prophylaxis of anthrax (including inhalational anthrax [postexposure]), treatment of presumed or confirmed rickettsial infections, including Rocky Mountain spotted fever (RMSF), fever, ehrlichiosis, and anaplasmosis, and for the treatment of Bartonella infections, for the treatment of brucellosis, for the treatment of Burkholderia Infections, Chlamydial Infections, Lymphogranuloma venereum Psittacosis, Ehrlichiosis and Anaplasmosis, Gonorrhea and Associated Infections, Epididymitis, Proctitis, Granuloma Inguinale (Donovanosis,) Legionella Infections, Leptospirosis, Lyme Disease, Prophylaxis of Lyme Disease, Erythema Migrans, Early Neurologic Lyme Disease, Lyme Carditis, or Borrelial Lymphocytoma, Lyme Arthritis, Malaria, and prevention, Mycobacterial Infections, Mycobacterium marinum Infections, Pelvic Inflammatory Disease, Parenteral Regimens, Plague, pleural Effusion, Rickettsial Infections, Q Fever, Syphilis, Tularemia, Treatment, Postexposure Prophylaxis When reconstituted and diluted with 0.9% sodium chloride or 5% dextrose, doxycycline hyclate IV solutions containing 0.1-1 mg of doxycycline per mL are stable for 48 hours at 25° C.; when reconstituted and diluted with Ringer's, 10% invert sugar, Normosol-M® in D5W, Normosol-R® in D5W, Plasma-Lyte® 56 in 5% dextrose, or Plasma-Lyte® 148 in 5% dextrose, doxycycline hyclate IV solutions containing 0.1-1 mg/mL are stable for 12 hours at room temperature. The manufacturer states that doxycycline hyclate solutions prepared with any of these infusion solutions are stable for 72 hours at 2-8° C. when protected from direct sunlight and artificial light; however, after storage in this manner, infusion of these solutions must be completed within 12 hours Doxycycline hyclate IV solutions diluted to a concentration of 0.1-1 mg/mL with lactated Ringer's injection or 5% dextrose in lactated Ringer's injection must be infused within 6 hours to ensure stability. During infusion, all doxycycline hyclate IV solutions must be protected from direct sunlight. (Martindale 2007 Electronic Version). Thus it can be seen that Doxycycline is not stable for more than short periods of a matter of hours.

Preparations of doxycycline hyclate have an acid pH and incompatibility may reasonably be expected with alkaline preparations or with drugs unstable at low pH.

Doxycycline is more active than tetracycline against many bacterial species including *Streptococcus pyogenes*, enterococci, *Nocardia* spp., and various anaerobes. Cross-resistance is common although some tetracycline-resistant *Staphylococcus aureus* respond to doxycycline. Doxycycline is also more active against protozoa, particularly *Plasmodium* spp.

Doxycycline is a tetracycline derivative with uses similar to those of tetracycline. It may sometimes be preferred to other tetracyclines in the prevention or treatment of susceptible infections because of its fairly reliable absorption and its long half-life that permits less frequent (often once daily) dosing. It also has the advantage that it can be given (with care) to patients with renal impairment. However, relatively high doses may need to be given for urinary-tract infections because of its low renal excretion.

For relapsing fever and louse-borne typhus, for the prophylaxis of leptospirosis, for periodontiti, for Lymphatic filariasis, for Musculoskeletal and joint disorders and for the treatment of acne.

Minocycline

According to some embodiments, the tetracycline is minocycline. Minocycline hydrochloride is a semisynthetic tetracycline antibiotic derived from tetracycline. The drug is usually bacteriostatic in action; it exerts its antimicrobial activity by inhibiting protein synthesis. It is a yellow crystalline powder that is sparingly soluble in water; slightly soluble in alcohol; practically insoluble in chloroform and in ether; soluble in solutions of alkali hydroxides and carbonates. pH of a solution in water containing the equivalent of minocycline 1% is between 3.5 and 4.5. Preparations of minocycline hydrochloride have an acid pH and incompatibility may reasonably be expected with alkaline preparations or with drugs unstable at low pH.

Minocycle is highly sensitive and should be stored in airtight containers and protected from light to prevent degradation. Therefore use in foamable formulations stored in airtight sealed containers under pressure with propellant may contribute to preserving stability subject to selection of compatible canisters and accessories.

Photosensitivity, manifested as an exaggerated sunburn reaction on areas of the body exposed to direct sunlight or ultraviolet light, has occurred with tetracyclines and Minocycline has been associated with pigmentation of the skin and other tissues.

Minocycline has a spectrum of activity and mode of action similar to that of tetracycline but it is more active against many species including *Staphylococcus aureus*, streptococci, *Neisseria meningitidis*, various enterobacteria, *Acinetobacter, Bacteroides, Haemophilus, Nocardia*, and some mycobacteria, including *M. leprae*. Partial cross-resistance exists between minocycline and other tetracyclines but some strains resistant to other drugs of the group remain sensitive to minocycline, perhaps because of better cell-wall penetration. Minocycline is a tetracycline derivative with uses similar to those of tetracycline. It is also a component of multidrug regimens for the treatment of leprosy and has been used in the prophylaxis of meningococcal infection to eliminate the carrier state, but the high incidence of vestibular disturbances means that it is not the drug of choice for the latter. It has neuroprotective properties. It is being investigated for motor neurone disease, for the management of Huntington's chorea. It is used in the treatment of rheumatoid arthritis and in the prevention or treatment of various skin disorders, including acne.

Steroids

In an embodiment, the active agent is a steroid. In certain embodiments the steroid is a corticosteroid, including but not limited to, hydrocortisone, hydroxyltriamcinolone, alpha-methyl dexamethasone, dexamethasone-phosphate, beclomethsone dipropionate, clobetasol valemate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortmate, mepreddisone, paramethasone, prednisolone, prednisone, beclomethasone dipropionate, triamcinolone, as well as analogs, derivatives, salts, ions and complexes thereof.

Many steroids are typically insoluble or partially soluble in various hydrophobic solvents.

In certain embodiments, the steroid is a hormone or a vitamin or an anti-infective agent, as exemplified by pregnane, cholestane, ergostane, aldosterone, androsterone, calcidiol, calciol, calcitriol, calcipotriol, clomegestone, cholesterol, corticosterone, cortisol, cortisone, dihydrotestosterone, ergosterol, estradiol, estriol, estrone, ethinylestradiol, fusidic acid, lanosterol, prednisolone, prednisone, progesterone, spironolactone, timobesone and testosterone, as well as analogs, derivatives, salts, ions and complexes thereof. For substances like calcitriol, very low amounts such as about 0.0001% to about 0.005% by weight of foam formulation or gel or ointment or suspension, or about 0.0001%, about 0.0002%, about 0.0003%, about 0.0004%, about 0.0005%, about 0.0006%, about 0.0007%, about 0.0008%, about 0.0009%, about 0.001%, about 0.0011%, about 0.0012%, about 0.0013%, about 0.0014%, about 0.0015%, about 0.0016%, about 0.0017%, about 0.0018%, about 0.0019%, about 0.002%, about 0.003%, about 0.004%, about 0.005% by weight are effective. In some embodiments the active pharmaceutical agent is delivered by more than one route, for example, topically and body cavity.

In an embodiment, the steroid is mometasone furoate. In certain embodiments it can be used topically to treat psoriasis and dermatitis. In certain other embodiments it can be applied in nasal administration to treat disorders, such as, allergic rhinitis and asthma.

NSAID

In an embodiment, the active agent is a non-steroidal anti-inflammatory agent. In the context a nonsteroidal anti-inflammatory agent (also termed herein "NSAID") is a pharmaceutically active compound, other than a corticosteroid, which affects the immune system in a fashion that results in a reduction, inhibition, prevention, amelioration or prevention of an inflammatory process and/or the symptoms of inflammation and/or the production pro-inflammatory cytokines and other pro-inflammatory mediators, thereby treating or preventing a disease that involves inflammation.

In one or more embodiments, the NSAID is an inhibitor of the cyclooxygenase (COX) enzyme. Two forms of cyclooxygenase are known today: the constitutive cyclooxygenase (COX-1); and the inducible cyclooxygenase (COX-2), which is pro-inflammatory. Thus, in one or more embodiments, the NSAID is selected from the group consisting of a COX-1 inhibitor, a COX-2 inhibitor or a non-selective NSAID, which simultaneously inhibits both COX-1 and COX-2.

In one or more embodiments, the NSAID is salicylic acid a salicylic acid derivatives. Exemplary salicylic acid derivative include, in a non limiting fashion, aspirin, sodium salicylate, choline magnesium trislicylate, salsalate, diflunisal, salicylsalicylic acid, sulfasalazine, olsalazine, esters of salicylic acid with a carboxylic acid, esters of salicylic acid with a dicarboxylic acid, esters of salicylic acid with a fatty acid, esters of salicylic acid with a hydroxyl fatty acid, esters of salicylic acid with an essential fatty acid, esters of salicylic acid with a polycarboxylic acid, and any compound wherein salicylic acid is linked to an organic moiety through a covalent bond.

In one or more embodiments, the NSAID is para-aminophenol (e.g., acetaminophen) and salts and derivatives thereof.

In one or more embodiments, the NSAID is an indole or an indole-acetic acid derivative (e.g., indomethacin, sulindac, etodolac) and salts and derivatives thereof.

In one or more embodiments, the NSAID is an aryl acetic acids (e.g., tolmetin, diclofenac, ketorolac) and salts and derivatives thereof.

In one or more embodiments, the NSAID is an arylpropionic acid and salts and derivatives thereof. Exemplary arylpropionic acid derivative include, in a non limiting fashion, are ibuprofen, naproxen, flubiprofen, ketoprofen, fenoprofen, oxaprozin.

In one or more embodiments, the NSAID is anthranilic acids or an anthranilic acid derivative, also termed "fenamates" (e.g., mefenamic acid, meclofenamic acid) and salts and derivatives thereof.

In one or more embodiments, the NSAID is selected from the group of enolic acids, enolic acid salts, enolic acid esters, amides, anhydrides and salts and derivatives thereof. Non-limiting examples of enolic acid derivatives include oxicams (piroxicam, tenoxicam) and pyrazolidinediones (phenylbutazone, oxyphenthratrazone)

Yet, in additional embodiments, the NSAID is an alkanone (e.g., nabumetone).

Selective COX-2 Inhibitors include, in an exemplary manner diaryl-substituted furanones (e.g., Rofecoxib); diaryl-substituted pyrazoles (e.g., Celecoxib); indole acetic acids (e.g., Etodolac); and sulfonanilides (e.g., Nimesulide) and salts and derivatives thereof.

Many NSAIDs are typically insoluble or partially soluble in hydrophobic solvents.

Local Anesthetic Agents

In an embodiment, the active agent is a local anesthetic agent. Without limiting the scope, the anesthetic agent can be selected from the group consisting of benzocaine, lidocaine, bupivacaine, chlorprocaine, dibucaine, etidocaine, mepivacaine, tetracaine, dyclonine, hexylcaine, procaine, cocaine, ketamine, pramoxine, phenol, any pharmaceutically acceptable salts thereof and mixtures of such anesthetic agents. Any mixture of synergistically beneficial anesthetic agents is contemplated.

Keratolytically Active Agents

A keratolytic agent may be included as an active agent of the composition. The term "keratolytically active agent" as used herein includes a compound that loosens and removes the stratum corneum of the skin, or alters the structure of the keratin layers of skin. Keratolytically active agents are used in the prevention or treatment of dermatological disorders that involve dry skin, hyperkeratinization (such as psoriasis), skin itching (such as xerosis), acne and rosacea.

Suitable keratolytically active agents include phenol and substituted phenolic compounds. Such compounds are known to dissolve and loosen the intracellular matrix of the hyperkeratinized tissue. As such, they are used in the prevention or treatment of dermatological disorders. Dihydroxybenzene and derivatives thereof have been recognized as potent keratolytic agents. Resorcinol (m-dihydroxybenzene) and derivatives thereof are used in anti-acne preparations. In addition to hydroquinone (p-dihydroxybenzene) having anti-pigmentation properties, hydroquinone is also known to be keratolytic. These compounds also exhibit antiseptic properties. Cresols also possess bactericidal and keratolytic properties.

Vitamin A and vitamin A derivatives, also termed herein "retinoids", such as retinoic acid, isoretinoic acid, retinol and retinal, as well as adapalene, tazarotene, isotretinoin, acitretin and additional retinoids known in the art of pharmaceuticals and cosmetics are another class of keratolytically active agents.

Another group of keratolytically active agents include alpha-hydroxy acids, such as lactic acid and glycolic acid and their respective salts and derivatives; and beta-hydroxy acids, such as salicylic acid (o-hydroxybenzoic acid) and salicylic acid salts and pharmaceutically acceptable derivatives.

Another class of keratolytically active agents includes urea and urea derivatives.

Immunomodulators

In an embodiment, the active agent is an immunomodulator. Immunomodulators are chemically or biologically-derived agents that modify the immune response or the functioning of the immune system. Immunomodulators suitable for use according to the present invention include, among other options, cyclic peptides, such as cyclosporine, tacrolimus, tresperimus, pimecrolimus, sirolimus, verolimus, laflunimus, laquinimod and imiquimod, as well as analogs, derivatives, salts, ions and complexes thereof. Such compounds, delivered in the foam, are especially advantageous in skin disorders such as psoriasis, eczema and atopic dermatitis, where the large skin areas are to be treated.

Retinoids

In an embodiment, the active agent is a retinoid. Retinoids suitable for use according to the present invention include, among other options, retinol, retinal, retinoic acid, isotretinoin, tazarotene, adapalene, 13-cis-retinoic acid, acitretin all-trans beta carotene, alpha carotene, lycopene, 9-cis-beta-carotene, lutein and zeaxanthin, as well as any additional retinoids known in the art of pharmaceuticals and cosmetics; and analogs, derivatives, salts, ions and complexes thereof.

Anti-Acne and Anti-Rosacea Active Agents

In an embodiment, the active agent is an anti-acne or an anti-rosacea agent. The anti-acne agent can be selected from the group consisting of resorcinol, sulfur, salicylic acid and salicylates, alpha-hydroxy acids, nonsteroidal anti-inflammatory agents, benzoyl peroxide, retinoic acid, isoretinoic acid and other retinoid compounds, adapalene, tazarotene, azelaic acid and azelaic acid derivatives, antibiotic agents, such as erythromycin and clyndamycin, coal tar, zinc salts and complexes, and combinations thereof, in a therapeutically effective concentration.

Antipsoriasis Agents

In an embodiment, the active agent is an anti-psoriasis agent. Such anti-psoriasis agents can be selected, among other options, from the group of keratolytically-active agents, salicylic acid, coal tar, anthralin, corticosteroids, vitamin D and derivatives and analogs thereof, including vitamin D3 analogs such as calcitriol, calcipotriol; retinoids, and photodynamic therapy agents.

Antiinfective Agents

In an embodiment, the active agent is an anti-infective agent. Such anti-infective agent can be selected from the group of an antibiotic agent, an antibacterial agent, an antifungal agent, an agent that controls yeast, an antiviral agent and an antiparasitic agent. Exemplary antiinfective agents are exemplified by beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quaternary ammonium compound, a biguanide, chlorohexidine, a triguanide, a bisbiguanide, a polymeric biguanide and a naturally occurring antibiotic compound, as well as analogs, derivatives, salts, ions and complexes thereof.

The Composition Essential Ingredients as Active Agents

In certain embodiments, a hydrophobic solvent possesses therapeutic properties on its own and therefore, it can be regarded as "active agent." For example, some essential oils kill microorganisms and can be effective in the treatment or prevention of conditions that involve microbial infection, such as bacterial, fungal and viral conditions. Additionally, the occlusive effect of hydrophobic solvents is useful for the treatment of conditions which involve damaged skin, such as psoriasis or atopic dermatitis. The combination of a hydrophobic solvent and a therapeutically effective fatty alcohol or fatty acid may afford a synergistic beneficial effect in conditions characterized, for example, by infection and/or inflammation.

Combination of Active Agents

Several disorders involve a combination of more than one etiological factor; and therefore, the use of more that one active agents is advantageous. For example, psoriasis involves excessive cell proliferation and inadequate cell differentiation as well as inflammation. Atopic dermatitis involves keratinocyte growth abnormality, skin dryness and inflammation. Bacterial, fungal and viral infections involve pathogen colonization at the affected site and inflammation. Hence, in many cases, the inclusion of a combination of active agents in the pharmaceutical composition can be desirable. Thus, in one or more embodiments, the composition further includes at least two active agents, in a therapeutically effective concentration.

In an embodiment one of the active agents is a vitamin, a vitamin derivative or analogue thereof. In a preferred embodiment the vitamin, vitamin derivative or analogue thereof is oil soluble.

Microsponges

Microsponges (or microspheres) are rigid, porous and sponge-like round microscopic particles of cross-linked polymer beads (e.g., polystyrene or copolymers thereof), each defining a substantially non-collapsible pore network. Microsponges can be loaded with an active ingredient and can provide a controlled time release of the active ingredient to skin or to a mucosal membrane upon application of the formulation. The slow release is intended to reduce irritation by the active. Microsponge® delivery technology was developed by Advanced Polymer Systems. In one or more embodiments the composition comprises one or more active agents loaded into Microsponges with a waterless carrier described herein, which may also comprise a modulating agent.

Fields of Applications

The carrier of the present disclosure is suitable for treating any inflicted surface or preventing onset of an anticipated disorder or disease or for achieving a period of remission. In one or more embodiments, carrier is suitable for administration to the skin, a body surface, a body cavity or mucosal surface, e.g., the cavity and/or the mucosa of the nose, mouth, eye, respiratory system, vagina, urethra, rectum and the ear canal (severally and interchangeably termed herein "target site").

The foamable carrier of the present disclosure is also suitable for preventing a disorder or disease prior to its onset. The foamable composition comprising for example a tetracycline may be applied to a body surface or a body cavity to try and prevent apoptosis, a disorder or disease prior to onset thereof. For example, prior to an anticipated inflammatory reaction or risk thereof, or prior to an anticipated onset of apoptosis or a risk thereof, or prior to an anticipated onset of inflammatory cytokines or risk thereof, prior to a medical procedure requiring intervention such as chemo therapy; radiotherapy, photodynamic therapy, laser therapy, etc. In an embodiment the composition is applied to prevent or reduce the risk of spreading.

According to an embodiment a none limiting of list of disorders where a tetracycline antibiotic might be used to prevent a disease or disorder includes prophylaxis of gonococcal and chlamydial ophthalmia, neonatal conjunctivitis, periodontal disease, postoperative tetracycline, prophylaxis in pregnancy termination, for prevention of skin rash/acneiform skin eruption during cancer therapy, intraoperative topical tetracycline sclerotherapy following mastectomy for prevention of postoperative mastectomy seromas etc.

By selecting a suitable active agent, or a combination of at least two active agents, the composition of the present disclosure is useful in alleviating or treating an animal or a human patient having or anticipated to have any one of a variety of dermatological diseases or disorders, or where such agent or agents have shown proficiency in preventative therapy in preventing such diseases or disorders, including, but not limited to a bacterial infection, a benign tumor, a bullous disease, a burn, a chlamydia infection, a condition which respond to hormone therapy, a cut, a dermatitis, a dermatophyte infection, a dermatose, a disorder of a body cavity, a disorder of cornification, a disorder of the nose, a disorder of the penile urethra or ear canal, a disorder of the rectum, a disorder of the respiratory system, a disorder of the vagina, a disorder which responds to hormone replacement therapy, a disorder which responds to transdermal nicotine administration, a disorders of hair follicles, a disorders of sebaceous glands, a disorders of sweating, a fungal infection, a gonorrhea infection, a gynecological disorders that respond to hormonal therapy, a malignant tumor, a non-dermatological disorder which responds to topical or transdermal delivery of an active agent, a parasitic infection, a pelvic inflammation, a pigmentation disorder, a scaling papular diseases, a sexual dysfunction disorder, a sexually transmitted disease, a vaginal disorder, a viral infection, a vulvar disorder, a vulvovaginal infection, a wound, a yeast infection, abscess, acne, acne conglobata, acne fulminans, acne scars, acne vulgaris, actinic keratosis, acute and chronic salpingitis, acute febrile neutrophilic dermatosis, acute lymphangitis, acute pelvic inflammatory disease, acute soft tissue injury, albinism, allergic contact dermatitis, alopecia, alopecia areata, alopecia totalis, alopecia universalis, an allergy, an anal abscess or fistula, an anal and rectal disease, an anal disorder, an anal fissure, an anal wart, an ear disorder, an hormonal disorder, an inflammatory reaction, an intra-vaginal or rectal sexually-transmitted and non-sexually-transmitted infectious disease, anal cancer, anal excoriation, anal fissures, anal itch, anal pruritus, anal soreness, anal warts, angiomas, arthritis, athlete's foot, atopic dermatitis, back pain, bacterial skin infections, bacterial vaginosis, baldness, basal cell carcinoma, benign tumors, blisters, bromhidrosis, bullous diseases, bullous pemphigoid, burn, calluses, calluses candidiasis, cancer of the cervix, cancer of the vagina, cancer of the vulva, candidal vaginitis, candidiasis, carbuncles, cellulitis, cervical cancer, cervicitis, chancroid, chemical burns, chicken pox, chloasma, cholesteatoma, cholinergic urticaria, chronic dermatitis, chronic effects of sunlight, cold sores, cold urticaria, comedones, constipation, contact dermatitis, corns, creeping eruption, Crohn's disease, cutaneous abscess, cutaneous larva migrans, cutaneous myiasis, dark spots, delusional parasitosis, Dercum disease, dermatitis, dermatitis herpetiformis, dermatofibroma, dermatological inflammation, dermatological pain, dermatophytoses, dermographism, diaper rash, drug eruptions and reactions, drug-induced hyperpigmentation, dyshidrotic eczema, dysmenorrhea, dyspareunia, dysplastic nevi, ecthyma, ectodermal dysplasia, ectopic pregnancy, eczema, endometriosis, endometritis, epidermal necrolysis, epidermoid cyst, erysipelas, erythema multiforme, erythema nodosum, erythrasma, exfoliative dermatitis, fallopian tube cancer and gestational trophoblastic disease, fecal incontinence, female orgasmic disorder, folliculitis, fungal nail infections, fungal skin infections, furuncles, gangrene, generalized exfoliative dermatitis, genital cancer, genital herpes, genital ulcer, genital warts, granuloma annulare, granuloma inguinale, gynecological neoplasms including endometrial cancer, head lice, hemorrhoids, hepatitis B, herpes, herpes simplex, hidradenitis suppurativa, hirsutism, HIV/AIDS, hives, human papillomavirus (HPV), hyperhidrosis, hyperpigmentation melasma, hypertrichosis, hypohidrosis, hypopigmentation, ichthyosis, impetigo, inflammatory acne, inflammatory reactions, ingrown nails, intertrigo, irritant contact dermatitis, ischemic necrosis, itching, jock itch, joint pain, Kaposi's sarcoma, keloid, keratinous cyst, keratoacanthoma, keratosis pilaris, lichen planus, lichen sclerosus, lichen simplex chronicus, linear immunoglobulin A disease, lipomas, localized pain in general, lymphadenitis, lymphangitis, lymphogranuloma venereum, male pattern baldness, malignant melanoma, malignant tumors, mastocytosis, measles, melanoma, midcycle pain, midcycle pain due to ovulation, miliaria, mittelschmerz, moles, molluscum contagiosum, MRSA, mucopurulent cervicitis (MPC), muscle pain, necrotizing fasciitis, necrotizing myositis, necrotizing subcutaneous infection, necrotizing subcutaneous infections, nodular papulopustular acne, nongonococcal urethritis (NGU), non-inflammatory acne, nummular dermatitis, oophoritis, oral herpes, osteoarthritis, ostheoarthritis, ovarian cancer, ovarian cysts and masses, paget's disease of the nipples, panniculitis, papules, parapsoriasis paronychia, parasitic infections, parasitic skin infections, paronychial infection, pediculosis, pelvic congestion syndrome, pelvic inflammatory disease, pelvic pain, pemphigus, perianal pruritus, perianal thrush, perioral dermatitis, photo-allergy, photodamage, photo-irritation, photosensitivity, pigmentation disorders, pimples, pityriasis Lichenoides, pityriasis rosea, pityriasis rubra pilaris, poison ivy, poison oak, polyps of the colon and rectum, postinflammatory hyperpigmentation, postinflammatory hypopigmentation, post-operative or post-surgical skin conditions, premenstrual syndrome, pressure sores, pressure ulcers, pressure urticaria, pruritis, pruritus ani, pseudofolliculitis barbae, psoriasis, PUPPP, purpura, pustules, pyogenic granuloma, rash, reactions to sunlight, rectal abscess, rectal fistula, rheumatic pain, ringworm, rosacea, roseola, rubella, salpingitis, scabies, scalded skin syndrome, scaling papular diseases, scarring, scleroderma, sebaceous cyst, seborrheic dermatitis, seborrheic keratoses, seborrheic keratosis, sexual arousal disorder, shingles, skin aging, skin cancer, skin neoplasia, skin neoplasms, skin rash, skin tags, skin ulcers, sports injuries, squamous cell carcinoma, staphylococcal scalded skin syndrome, stasis dermatitis, Stevens-Johnson syndrome, sun spots, sunburn, thermal burns, tinea corporis, tinea cruris, tinea pedis, tinea versicolor, toxic epidermal necrolysis, trauma or injury to the skin, trichomonas vaginalis, trichomoniasis, vaginal cancer, vaginal dryness, vaginismus, varicella zoster virus, viral skin infections, vitamin D deficiency, vitiligo, vulvar cancer, vulvar disorders, vulvar dystrophy, vulvar intraepithelial neoplasia (VIN), vulvar pain, vulvodynia, warts, water hives, wrinkles, xerosis, yeast skin infections, zoster.

Likewise, the composition of the present disclosure is suitable for preventing or treating or alleviating a disorder or anticipated disorder of a body cavity or mucosal surface, e.g., the mucosa of the nose, mouth, eye, ear, respiratory system, vagina, urethra, or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranuloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment of the present disclosure, the composition is useful for the treatment of an infection. In one or more embodiments, the composition is suitable for the treatment or prevention of an infection, selected from the group of a bacterial infection, a fungal infection, a yeast infection, a viral infection and a parasitic infection.

In an embodiment of the present disclosure, the composition is useful for the treatment of wound, ulcer and burn. This use is particularly important since the composition of the present disclosure creates a thin, semi-occlusive layer, which coats the damaged tissue, while allowing exudates to be released from the tissue.

The composition of the present disclosure is also suitable for administering a hormone to the skin or to a mucosal membrane or to a body cavity, in order to deliver the hormone into the tissue of the target organ, in any disorder that responds to treatment with a hormone.

In one embodiment the disorder is an inflammation, skin inflammation, acne, rosacea, actinic keratosis, skin cancer, a local pain, joint pain and ostheoarthritis; the active agent is a nonsteroidal anti-inflammatory drug, given at a therapeutically effective concentration.

In light of the hygroscopic nature of the composition, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam is particularly advantageous because foam can expand in the body cavity and penetrate into hidden areas that cannot be reached by any other alternative means of administration.

Cosmetic Use

In one or more embodiments, the composition may be used for cosmetic use. For example it may be used as part of a cosmetic formulation to prevent a cosmetic disorder or to improve the skin. Alternatively it may be used with cosmetic effect for example as a cosmetic remover. It can be dispensed in small quantities targeted to a surface and applied locally with mechanical force causing the foam or gel to break.

Route of Administration

In one or more embodiments the formulations are prepared without propellant and are applied as a gel or ointment, for example, with the tetracycline as a suspension. Alternatively, in one or more embodiments the formulations are prepared with a propellant and are applied as a foam.

In one or more embodiments, the gel is capable of forming a foamable composition when packaged into an aerosol canister, equipped with a valve and pressurized with a liquid or pressurized gas propellant and is capable of releasing a foam of quality that is breakable upon application of shear force but is not thermolabile at about or close to body temperature (about 36° C.).

In one or more embodiments, upon addition of between about 8% to about 12% propellant, the formulations 238P, 238A, 238B, 238C, 238D, 244A, 244B, 244P in Examples 4, 6 and 7 provided a foam of good or excellent quality that had a collapse time in excess of 3 minutes.

Application can be hourly, 2 hourly, 3 hourly, four hourly, six hourly or eight hourly, twelve hourly, daily, alternate-day or intermittent, as necessary. For reasons of compliance less frequent applications, where possible are preferable such as twice-daily or daily single applications. In cases where prolonged or long term treatment is required a higher initial dose is provided followed by a gradual reduction to a lower maintenance dose, which can be increased if further outbreaks occur.

The formulations are suitable for administration directly or indirectly to an inflicted area, in need of treatment, through the following routes of administration:
1. Topical administration: for local effect, it is applied directly where its action is desired;
2. Enteral: when the desired effect is systemic (non-local), it is given via the digestive tract; and
3. Parenteral: when the desired effect is systemic, it is given by other routes than the digestive tract The following list more specifically exemplifies some routes of administration.
1. Topical Topical administration is any form of administration that reaches a body organ topically, such as epicutaneous administration (application onto the skin), inhalation, enema, eye drops (onto the conjunctiva), ear drops, intranasal (into the nose) and vaginal.

Exemplary dosage forms that are suitable for topical administration of the stable tetracycline formulations include cream, gel, liniment, lotion, ointment, paste, spray, foam, mousse, lacquer (e.g., for nail treatment) and transdermal patch. Additionally, topical vaginal dosage forms may include a douche, an intrauterine device, a pessary (vaginal suppository), a vaginal ring and a vaginal tablet. Rectal dosage forms include enema and suppositories. Inhaled dosage forms include aerosol inhalers, metered dose inhalers and solutions for nebulizer. Ophthalmic dosage forms include eye drop (solution or suspension), ophthalmic gel and ophthalmic ointment. In another embodiment the dosage form is a foam that is quickly breaking (non thermally stable) or breakable under shear force which allows comfortable application and well directed administration to the target area.

2. Enteral

Enteral is any form of administration that involves any part of the gastrointestinal tract by mouth (orally), as buccal or sublingual tablets, capsules, suspensions, solutions, powder or drops; by gastric feeding tube, duodenal feeding tube, or gastrostomy; and rectally, in suppository or enema form.

3. Parenteral by Injection or Infusion

Intravenous (into a vein); intraarterial (into an artery); intramuscular (into a muscle); intracardiac (into the heart); subcutaneous (under the skin); intraosseous infusion (into the bone marrow); intradermal, (into the skin itself); intrathecal (into the spinal canal); and intraperitoneal (into the peritoneum).

4. Other Parenteral

Transdermal (diffusion through the intact skin); transmucosal (diffusion through a mucous membrane), e.g. insufflation (snorting), sublingual, buccal (absorbed through cheek near gumline) and vaginal; and inhalational; epidural (synonym: peridural) (injection or infusion into the epidural space); and intravitreal.

EXAMPLES

The invention is described with reference to the following examples, in a non-limiting manner. The following examples exemplify the compositions and methods described herein. The examples are for the purposes of illustration only and are not intended to be limiting. Many variations will suggest themselves and are within the full intended scope.

Example 1—General Manufacturing Procedures

The following procedures are used to produce gel and foam samples described in the examples below, in which only the steps relevant to each formulation are performed depending on the type and nature of ingredients used.

Step 1: Hydrophobic solvent are heated to 60-70° C.

Step 2: Fatty alcohols if present, fatty acids if present, surfactants if present are added to the hydrophobic solvent and the formulation is mixed until complete melting.

Step 3: The formulation is cooled down to 30-40° C., active ingredients if present are added and the formulation is mixed until homogeneity is obtained.

Step 4—for Gels: The formulation is cooled down to room temperature under mixing and packaged into suitable containers.

Step 4—for Foams: The formulation is packaged in aerosol canisters which are crimped with a valve, pressurized with propellant and equipped with an actuator suitable for foam dispensing. Optionally a metered dosage unit can utilized, to achieve delivery of repeatable measured doses of foam.

Materials

TABLE 1

Exemplary possible ingredients suitable for the production of gels and/or foamable compositions disclosed herein. Equivalent materials from other manufacturers can also be used satisfactorily.

| Chemical Name | Function | Commercial Name | Supplier |
|---|---|---|---|
| Alpha-tocopherol | Antioxidant | Alpha-tocopherol | Sigma-Aldrich |
| Beeswax white | Foam adjuvant | Beeswax white | Henry Lamotte |
| Behenyl alcohol | Foam adjuvant | Lanette 22 | Cognis |
| Benzoyl peroxide | Active agent | Benzoyl peroxide | Spectrum |
| BHA | Antioxidant | Butylhydroxyanisole | Merk |
| BHT | Antioxidant | Butylated Hydroxitoluene | Spectrum |
| C12-C15 alkyl benzoate | Solvent | C12-C15 alkyl benzoate | Finetex |
| Castor oil | Solvent | Castor oil | Fluka |
| Ceteareth-20 | Surfactant | Sympatens acs 200G | Colb |
| Cetearyl octanoate | Solvent | Luvitol EHO | BASF |
| Ceteth-2 | Surfactant | Lipocol C-2 | Lipo |
| Cetostearyl alcohol | Foam adjuvant | Speziol C16-C18 | Cognis |
| Cetyl alcohol | Foam adjuvant | Speziol C16 | Cognis |
| Cholesterol | Wax | Cholesterol | Spectrum |
| Cocoglycerides | Solvent | Novata A | Cognis |
| Coconut oil | Solvent | Coconut oil | Henry Lamotte |
| Cyclomethicone-5 | Solvent | ST-cyclomethicone-5 | Dow |
| Diclofenac Sodium | Active agent | Diclofenac Sodium | Spectrum |
| Diethylene glycol monoethyl ether | Solvent | Transcutol | Gattefosse |
| Dimethyl Isosorbide | Solvent | Dimethyl Isosorbide | Dotticon |
| Dimethyl Sulfoxide | Solvent | Dimethyl Sulfoxide | Fluka |
| Diisopropyl adipate | Solvent | Isoadipate | Symrise GmbH |
| Doxycycline Hyclate | Active agent | Doxycycline Hyclate | Yangzhou |
| Ethanol Absolute | Solvent | Ethanol Absolute | J. T. Baker |
| Ethylcellulose | Polymer | EC-Ethocel 100 cP FP | Colorcon Dow |
| Gelled mineral oil | Solvent | Versagel M 750 | Penreco |
| PPG-20 Methyl Glucose Ether Distearate | Humectant | Glucam P20 Distearate | Lubrizol |
| Glycerin | Solvent | Glycerin | Cognis |
| Glyceryl monostearate | Surfactant | Cutina GMS V PH | Cognis |
| Hard Fat | Wax | Softisan 378 | Sasol |
| Heavy Mineral Oil | Solvent | Paraffin oil liquid heavy | Gadot |
| Hexylene Glycol | Solvent | Hexylene Glycol | Sigma-Aldrich |
| Hydrogenated castor oil | Foam adjuvant | Cutina HR | Cognis |
| Isododecane | Solvent | AB117128 | ABCR GmbH & Co. KG |
| Isopropyl myristate | Solvent | Isopropyl Myristate Ph. | Cognis |
| Isostearic acid | Foam adjuvant | Isostearic acid | Stearinerie Dubois |
| Isostearyl alcohol | Solvent | Prisorine 3515 | Croda |
| Lanolin | Foam adjuvant | Lanolin | Spectrum |
| Lareth-4 | Surfactant | Dehydol LS 4 DEO N | Cognis |
| Light Mineral Oil | Solvent | Pioner 2076P | Hansen & Rosenthal |
| MCT Oil | Solvent | Captex 355 | Abitec |
| Menthol | Additive | Menthol | Premium Ingredients Int. |
| Methyl glucose sesquistearate | Surfactant | Tego Care PS | Evonik Goldcshmidt |
| Metronidazole | Active agent | Metronidazole | Galdetma |
| Minocycline HCl | Active agent | Minocycline HCl | Hovione |
| Mometasone furoate | Active agent | Mometasone furoate | Sicor de Mexico |
| Cetearyl alcohol & coconut alcohol | Surfactant | Montanov S | Seppic |
| Myristyl alcohol | Foam adjuvant | Speziol C14 | Cognis |
| Octyldodecanol | Solvent | Eutanol G | Cognis |
| Oleic acid | Solvent | Oleic acid | Spectrum |
| Oleth-20 | Surfactant | Emulgin O 0 S | Cognis |
| Oleyl alcohol | Solvent | HD Eutanol V PH | Cognis |
| Palmitic acid | Foam adjuvant | Edenor C16 98-100GW | Cognis |
| Paraffin wax 42-44 | Wax | Paraffin 42-44 | Merck |
| Paraffin wax 51-53 | Wax | Paraffin 51-53 | Merck |
| Paraffin wax 58-62 | Wax | Paraffin 58-62 | Merck |
| PEG-40 Hydrogenated castor oil | Surfactant | Emulgin HRE 40 | Cognis |

TABLE 1-continued

Exemplary possible ingredients suitable for the production of gels and/or foamable compositions disclosed herein. Equivalent materials from other manufacturers can also be used satisfactorily.

| Chemical Name | Function | Commercial Name | Supplier |
| --- | --- | --- | --- |
| Polyethylene glycol-200 | Solvent | PEG 200 | Merck |
| Polyethylene glycol-400 | Solvent | PEG 400 | Sigma-Aldrich |
| PEG-75 Lanolin | Surfactant | SOLULAN 75 | Lubrizol |
| PEG-100 Stearate | Surfactant | Myrj 59 P | Croda |
| PEG-150 distearate | Surfactant | Emulgin EO 33 | Cognis |
| Permethrin | Active agent | Permethrin | Sigma |
| Petrolatum | Carrier | Sofmetic LMP | Sofmetic |
| Pimecrolimus | Active agent | Pimecrolimus | — |
| PPG 15 stearyl ether | Solvent | Arlamol E | Uniqema |
| PPG-20-methyl glucose ether | Humectant | Glucam P-20 | Lubrizol |
| Propane/Isobutane/Butane (20:78:2) | Propellant | A-46 | Aeropress |
| Propane/Isobutane/Butane (55:18:27) | Propellant | AP-70 | Aeropress |
| Propyl gallate | Antioxidant | Propyl gallate | Sigma-Aldrich |
| Propylene glycol | Solvent | Propylene glycol | Gadot |
| Salicylic acid | Active agent | Salicylic acid | Merck |
| Silicon dioxide | Dispersant | Aerosil R 972 PH | Evonik-Goldschmidt GmbH |
| Sorbitan sesquistearate | Surfactant | Tego care PS | Degussa |
| Soybean oil | Solvent | Soybean oil | Spectrum |
| Sorbitan monopalmitate | Surfactant | SPAN 40 | Spectrum |
| Sorbitan monostearate | Surfactant | SPAN 60 | Uniqema |
| Steareth-2 | Surfactant | Brij 72 | Spectrum |
| Steareth-21 | Surfactant | Brij 721 | Spectrum |
| Stearic acid | Foam adjuvant | Edenol ST1M | Cognis |
| Stearyl Alcohol | Foam adjuvant | Speziol C18 | Cognis |
| Sucrose stearic acid estersD1803 | Surfactant | Surfhope SE D1803 | Mitsubishi |
| Sucrose stearic acid estersD1807 | Surfactant | Surfhope SE D1807 | Mitsubishi |
| Sucrose stearic acid estersD1811 | Surfactant | Surfhope SE D1811 | Mitsubishi |
| Sucrose stearic acid estersD1813 | Surfactant | Surfhope SE D1813 | Mitsubishi |
| Terbinafine HCl | Active agent | Terbinafine HCl | Taro |
| Tetracycline HCl | Active agent | Tetracycline HCl | Xian lijun |
| Titanium dioxide | — | Kemira AFDC | Kermira |
| Polysorbate 20 | Surfactant | Tween 20 | Merck |
| Polysorbate 60 | Surfactant | Tween 60 | Merck |
| Urea | Active agent | Urea | Gadot |
| Vitamin E | Antioxydant | Tocopherol | Sigma |
| White Petrolatum (hard) | Carrier | Vaseline codex GAL | Aiglon |
| White Petrolatum (soft) | Carrier | Sofmetic LMF | MMP |
| 1,3-Butandiol | Solvent | Butylene Glycol | Sigma-Aldrich |
| C12-15 Alkyl Lactate | Emollient | C12-15 Alkyl Lactate | A&E Connock |

Canisters Filling and Crimping

Each aerosol canister is filled with the bulk formulation) and crimped with valve using vacuum crimping machine. The process of applying a vacuum will cause most of the oxygen present to be eliminated. Addition of hydrocarbon propellant may, without being bound by any theory, further help to reduce the likelihood of any remaining oxygen reacting with the active ingredient. It may do so, without being bound by any theory, by one or more of dissolving in, to the extent present, the oil or hydrophobic phase of the formulation, by dissolving to a very limited extent in the aqueous phase, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing & Propellant Filling

Pressurizing is carried out using a hydrocarbon gas or gas mixture. Canisters are filled and then warmed for 30 seconds in a warm bath at 50° C. and well shaken immediately thereafter.

By way of non-limiting example, tests are briefly set out below as would be appreciated by a person of the art.

Viscosity is measured with Brookfield LVDV-II+PRO with spindle SC4-25 at ambient temperature and 20, 10, 5 and/or 1 RPM. Viscosity is usually measured at 10 RPM or 20 RPM. However, at about the apparent upper limit for the spindle of ~>50,000 CP, the viscosity at 1 RPM may be measured, although the figures are of a higher magnitude.

Chemical Stability: the amount of active agent present is analyzed chromatographically. Analysis is carried out after formulation preparation and at appropriate time intervals thereafter. The samples are typically stored in controlled temperature incubators at one or more of 5° C., 25° C. and 40° C. for several weeks or months. At appropriate time intervals samples are removed from the incubators and the concentration of active agent and/or a degradation product is measured.

Example 2—Oleaginous Formulations with Low Viscosity

The different hydrophobic solvents suitable for use in topical pharmaceutical compositions are generally liquid oils that have a low viscosity. When these oils are used as-is for active agents topical delivery, they have inter alia two non desirable properties: (1) because of their low viscosity, they tend to drop and to be runny and therefore not easy for the patient to apply onto the skin, (2) they have poor suspending properties leading to the rapid sedimentation of non-dissolved active ingredients (APIs), as described in Table 2.

TABLE 2

Low viscosity oleaginous preparations

| | Formulations | | | | | |
|---|---|---|---|---|---|---|
| | 001P % w/w | 001 % w/w | 002P % w/w | 002 % w/w | 008P % w/w | 008 % w/w |
| Ingredients | | | | | | |
| Heavy mineral oil | 75.00 | 75.00 | — | — | — | — |
| Light mineral oil | 25.00 | 25.00 | — | — | — | — |
| Soybean oil | — | — | 100 | 100 | — | — |
| Petrolatum | — | — | — | — | 50 | 50 |
| C12-C15 alkyl benzoate | — | — | — | — | 50 | 50 |
| Total | 100.00 | 100.00 | 100.00 | 100.00 | 100.00 | 100.00 |

TABLE 2-continued

Low viscosity oleaginous preparations

| | Formulations | | | | | |
|---|---|---|---|---|---|---|
| | 001P % w/w | 001 % w/w | 002P % w/w | 002 % w/w | 008P % w/w | 008 % w/w |
| Minocycline HCl | — | 0.1 | — | 0.1 | — | 0.1 |
| Results | | | | | | |
| Viscosity at 10 rpm (cP) | 96 | 92 | 47 | 49 | 488 | 303 |

As shown in formulations 001P and 002P, mixtures of mineral oils and soybean oil have a low viscosity. Formulations 001 and 002 show that after the addition of Minocycline HCl, the viscosity of the formulation remains unchanged and that the active ingredient sediments (as observed visually).

Similarly, as shown in formulations 008P and 008, the viscosity of mixtures of petrolatum and alkyl benzoate remains unchanged after the addition of Minocycline HCl.

Example 3—Oleaginous Formulations with High Viscosity

The influence of the combination of a tetracycline with fatty alcohols, fatty acids and waxes on formulation viscosity was assessed, as described in Table 3a. Formulations were prepared containing petrolatum or coconut oil, alone or in combination with fatty alcohols or fatty acids, and their viscosity was measured before and after the addition of 0.1% of a tetracycline, namely Minocycline HCl. Table 3 below presents the results of formulation viscosity before and after the addition of a tetracycline, as well as the percentage of viscosity increase due to the addition of the active ingredient. Apparently, as observed in this experiment, when the viscosity of the composition without minocycline is high, such as about or more than 25,000 cPs, the synergistic effect between the minocycline (at a low level of 0.1%) and the second rheology modifying agent is not discernable or is not expressed or does not prevail.

TABLE 3

High viscosity oleaginous preparations

| | Formulations | | | | | |
|---|---|---|---|---|---|---|
| | 018 % w/w | 019 % w/w | 020 % w/w | 021 % w/w | 022 % w/w | 023 % w/w |
| Ingredients | | | | | | |
| Petrolatum | 100 | 90 | 90 | 90 | — | — |
| Coconut oil | — | — | — | — | 100 | 90 |
| Stearyl alcohol | — | 10 | — | 5 | — | 10 |
| Stearic acid | — | — | 10 | 5 | — | — |
| Total | 100.00 | 100.00 | 100.00 | 100.00 | 100.00 | 100.00 |
| Viscosity Results at 10 rpm (cP) | | | | | | |
| Without Minocycline HCl | 17692 | 24347 | 21611 | 41511 | 20604 | 24571 |
| With 0.1% Minocycline HCl | 20252 | 21499 | 22011 | 40151 | 19340 | 22459 |
| % Viscosity Change | +14% | −12% | +2% | −3% | −6% | −9% |

Example 4—Mineral Oil-Based Formulations with Controlled Viscosity

Part A—Combination of a Tetracycline with a Fatty Alcohol, a Fatty Acid or a Wax The influence of the combination of a tetracycline with fatty alcohols, fatty acids and waxes on formulation viscosity was assessed, as described in Table 4a. Formulations containing a mixture of mineral oils with fatty alcohols, fatty acids, waxes and combinations thereof were prepared, and their viscosity was measured before and after the addition of a tetracycline, namely Minocycline HCl. Table 4a below presents the results of formulation viscosity before and after the addition of a tetracycline, as well as the percentage of viscosity increase due to the addition of the active ingredient.

TABLE 4a

Combination of a tetracycline with fatty alcohols, fatty acid and waxes

| | Formulations | | | | | | |
|---|---|---|---|---|---|---|---|
| | 003 % w/w | 004 % w/w | 005 % w/w | 024 % w/w | 027 % w/w | 036 % w/w | 028 % w/w |
| Ingredients | | | | | | | |
| Heavy mineral oil | 65 | 65 | 65 | 65 | 65 | 65 | 65 |
| Light mineral oil | 25 | 25 | 25 | 30 | 25 | 25 | 25 |
| Stearyl alcohol | 10 | — | — | — | 5 | — | 5 |
| Stearic acid | — | 10 | — | — | — | 5 | — |
| Beeswax | — | — | 10 | — | — | — | 2.5 |
| Hydrogenated castor oil | — | — | — | 5 | 5 | 5 | 2.5 |
| Total | 100.00 | 100.00 | 100.00 | 100.00 | 100.00 | 100.00 | 100.00 |
| Viscosity Results at 10 rpm (cP) | | | | | | | |
| Without Minocycline HCl | 951 | 1858 | 942 | 848 | 10718 | 6719 | 5823 |
| With 0.1% Minocycline HCl | 2652 | 8142 | 1695 | 6223 | 38936 | 26762 | 16924 |
| % Viscosity Change | +179% | +338% | +80% | +634% | +263% | +298% | +191% |

Surprisingly, it was discovered that the addition of minocycline HCl to mineral oil-based formulations 003 to 005 led to a substantial increase in viscosity, despite the very low concentration of minocycline HCL used, namely 0.1%. These totally unexpected results show that the combination of a tetracycline, even at very low concentrations, with fatty alcohols, or fatty acids or waxes has a strong synergistic effect on oleaginous formulation viscosity. Without being bound by any theory it seems that tetracyclines can interact with fatty acids or fatty alcohols to produce a rheology viscosity effect and may interact to form —without being bound by any theory a complex of some sort in the formulation, which provides for the rheology effect observed.

As shown in formulations 027, 036 and 028, the same effect of low concentrations of tetracycline on formulation viscosity is observed when the oleaginous composition contains a combination of a fatty alcohol or fatty acid with hydrogenated castor oil, with or without beeswax.

The results also indicate a strong role for hydrogenated caster oil as a rheology modulator in combination with minocycline as well as on its own to a lesser extent.

Part B—Combination of a Tetracycline with Different Fatty Alcohols

The influence of the combination of a tetracycline with different fatty alcohols on formulation viscosity was assessed, as described in Table 4b. Formulations containing a mixture of mineral oils with different fatty alcohols were prepared, and their viscosity was measured before and after the addition of a tetracycline, namely minocycline HCl. Table 4b below presents the results and shows, the percentage of viscosity change due to the addition of the active ingredient.

TABLE 4b

Combination of a tetracycline with different fatty alcohols

| | Formulations | | | |
|---|---|---|---|---|
| | 037 % w/w | 038 % w/w | 039 % w/w | 041 % w/w |
| Ingredients | | | | |
| Heavy mineral oil | 65 | 65 | 65 | 65 |
| Light mineral oil | 25 | 25 | 25 | 25 |

TABLE 4b-continued

Combination of a tetracycline with different fatty alcohols

| | Formulations | | | |
|---|---|---|---|---|
| | 037 % w/w | 038 % w/w | 039 % w/w | 041 % w/w |
| Myristyl alcohol | 10 | — | — | — |
| Cetyl alcohol | — | 10 | — | — |
| Stearyl alcohol | — | — | 10 | — |
| Behenyl alcohol | — | — | — | 10 |
| Total | 100.00 | 100.00 | 100.00 | 100.00 |
| Viscosity Results at 10 rpm (cP) | | | | |
| Without Minocycline HCl | 336 | 1808 | 960 | 5679 |
| With 0.1% Minocycline HCl | 1040 | 5775 | 4591 | 6527 |
| % Viscosity Change | +210% | +219% | +378% | +15% |

The results indicate that an increase in formulation viscosity upon addition of Minocyclineminocycline HCl is observed with myristyl alcohol, cetyl alcohol and stearyl alcohol. However, in this experiment the corresponding effect of behenyl alcohol alone (with low minocycline concentration) is lower.

Part C—Formulation with Increased Viscosity and Various Concentrations of Minocycline The influence of the combination of different concentrations of a tetracycline with fatty alcohols, fatty acids, waxes and combinations thereof on formulation viscosity was assessed, as described in Table 4c. Formulations containing a mixture of mineral oils with fatty alcohols, fatty acids, waxes and combinations thereof were prepared, and their viscosity was measured before and after the addition of different concentrations of a tetracycline, namely minocycline HCl.

TABLE 4c

Formulation with increased viscosity and various concentrations of Minocycline

| | Formulations | | | | |
|---|---|---|---|---|---|
| | 014 % w/w | 015 % w/w | 016 % w/w | 017 % w/w | 024 % w/w |
| Ingredients | | | | | |
| Heavy mineral oil | 65 | 65 | 65 | 65 | 65 |
| Light mineral oil | 30 | 30 | 30 | 30 | 30 |
| Stearyl alcohol | 5 | — | — | 2.5 | 1.25 |
| Stearic acid | — | 5 | — | — | 1.25 |
| Beeswax | — | — | — | — | 1.25 |
| Hydrogenated castor oil | — | — | 5 | 2.5 | 1.25 |
| Total | 100.00 | 100.00 | 100.00 | 100.00 | 100.00 |
| Viscosity Results at 10 rpm (cP) | | | | | |
| Without Minocycline HCl | 152 | 135 | 848 | 4527 | 2815 |
| With 0.1% Minocycline HCl | 234 | 779 | 6223 | 7007 | 4191 |
| % Viscosity Change | +54% | +477% | +634% | +55% | +49% |
| Without Minocycline HCl | 152 | 135 | 848 | 4527 | 2815 |
| With 0.5% Minocycline HCl | 1212 | 1107 | 14973 | 12717 | 9054 |
| % Viscosity Change | +697% | +720% | +1666% | +181% | +222% |
| Without Minocycline HCl | 152 | 135 | 848 | 4527 | 2815 |
| With 1.0% Minocycline HCl | 878 | 819 | 20108 | 10510 | 7806 |
| % Viscosity Change | +478% | +507% | +2271% | +132% | +177% |

Surprisingly, it was discovered that the addition of minocycline HCl to mineral oil-based formulations 014 to 017 and 024, containing as low as 5% of a fatty alcohol, a fatty acid a wax and combinations thereof, led to a very substantial increase in viscosity, where the increase in viscosity is dependent of the concentration of the active ingredient. It was noticed that formulations having a higher concentration of active ingredient have a higher viscosity.

Therefore, the combination of a tetracycline with a fatty alcohol, a fatty acid and/or a wax has a strong synergistic effect in the viscosity of oleaginous formulation. The results may indicate that subject to the second rheology agent used the effect of a certain concentration of tetracycline may reach a plateau or peak beyond which increasing the amount of minocycline will not significantly increase the rheology effect as reflected in the viscosity measurements.

A first glass vial was filed with a placebo of formulation 016, and a second glass vial was filed with formulation 016 containing 0.1% minocycline HCl. As depicted in FIG. 2, both vials were photographed in horizontal and vertical position showing that the placebo formulation is a liquid which freely flows, while the formulation containing 0.1% minocycline HCl is a semi-solid gel-like. Therefore, the addition of an amount as small as 0.1% minocycline HCl to said formulation has an outstanding effect both of the formulation viscosity and on the formulation physical state which changes from a liquid to a semi-solid.

The influence of the addition of different concentrations of a tetracycline on a mineral oils-based formulation was then studied when the active ingredient is combined with a mixture of mineral oils, fatty alcohols, fatty acids and waxes, as described in Table 4d and 4e.

TABLE 4d

Oleaginous stock formulation

| Ingredients | Stock Formulation 238P % w/w |
|---|---|
| Heavy mineral oil | 59.25 |
| Light mineral oil | 25.00 |
| Cyclomethicone | 5.00 |
| Stearyl alcohol | 1.50 |
| Beeswax | 2.00 |
| Stearic acid | 2.00 |
| Hydrogenated castor oil | 1.50 |
| Behenyl alcohol | 1.00 |
| Cetostearyl alcohol | 2.50 |
| Silicon dioxide | 0.25 |
| Total | 100.00 |

TABLE 4e

Oleaginous preparations with increased viscosity

| | Formulations | | | | |
|---|---|---|---|---|---|
| | 238P % w/w | 238A % w/w | 238B % w/w | 238C % w/w | 238D % w/w |
| Ingredients | | | | | |
| Stock Formulation 238P | 100.00 | 99.90 | 99.80 | 99.50 | 99.00 |
| Minocycline HCl | — | 0.10 | 0.20 | 0.50 | 1.00 |
| Viscosity Results at 10 rpm (cP) | 6639 | 15789 | 18476 | 20876 | 20748 |
| % Viscosity Change | — | +138% | +178% | +214% | +213% |

The combination of a tetracycline with a mixture of mineral oils, fatty alcohols, fatty acids and waxes has a strong synergistic effect and increases the formulation viscosity. The viscosity of a formulation containing 0.50% minocycline HCl is about three times higher than the viscosity of the placebo formulation. The effect on the formulation viscosity is clearly related to the concentration of the tetracycline: the higher the tetracycline concentration, the higher the viscosity of the formulation. In formulation 238, it appears that the viscosity increasing effect of Minocycline HCl reaches a plateau when the active ingredient is present at a concentration of about 0.50%.

In one or more embodiments, there is provided an oleaginous formulation containing mineral oils and a tetracycline in synergistic combination with a fatty alcohol, and/or a fatty acid and/or a wax, wherein the viscosity of the formulation is increased by the addition of the active ingredient by more than about 50%, more than about 100%, more than about 200%, more than about 300%, or more than about 500%.

In one or more embodiments, there is provided an oleaginous formulation containing hydrophobic solvents, an active ingredient in synergistic combination with a second rheology modulator, wherein the viscosity of the formulation is increased by the addition of the active ingredient by more than about 50%, more than about 100%, more than about 200%, more than about 300%, or more than about 500%.

In one or more embodiments, the increase in the formulation viscosity is related to the concentration of the active agent.

In one or more embodiments, the viscosity of the formulation is proportional to the concentration of the active agent: the higher the concentration of the active ingredient, the higher the formulation viscosity.

In one or more embodiments, the viscosity increasing effect of the active ingredient reaches a plateau when the concentration of the active ingredient is increased.

In one or more embodiments, the viscosity of the formulation containing the active ingredient is at least twice the viscosity of the sample formulation without the active ingredient when the active ingredient when present is present at a concentration of less than about 10%, less than about 5%, less than about 1%, less than about 0.5%, less than about 0.1%, less than about 0.05%, or less than about 0.01%.

Example 5—Mixture of Petrolatum and Mineral Oil-Based Formulations with Increased Viscosity In formulation based on petrolatum and various amounts of mineral oil, the influence of the combination of a tetracycline with fatty alcohols on formulation viscosity was assessed, as described in Table 5. Formulations containing a mixture of petrolatum and light mineral oil with a fatty alcohol were prepared, and their viscosity was measured before and after the addition of a tetracycline, namely minocycline HCl.

TABLE 5

Petrolatum and Mineral oil-based formulations with increased viscosity

| | Formulations | | | | |
|---|---|---|---|---|---|
| | 009 % w/w | 010 % w/w | 011 % w/w | 012 % w/w | 013 % w/w |
| Ingredients | | | | | |
| Petrolatum | 90 | 65 | 40 | 15 | 10 |
| Light Mineral oil | — | 25 | 50 | 75 | 90 |
| Stearyl alcohol | 10 | 10 | 10 | 10 | 10 |
| Total | 100.00 | 100.00 | 100.00 | 100.00 | 110.00 |
| Viscosity Results at 10 rpm (cP) | | | | | |
| Without Minocycline HCl | 26234 | 10510 | 3263 | 378 | 341 |
| With 0.1% Minocycline HCl | 28058 | 12254 | 5039 | 1204 | 1307 |
| % Viscosity Change | +7% | +17% | +54% | +219% | +283% |

When the viscosity of the placebo formulation is high, as in formulation 009, and the concentration of minocyline is low (e.g. 0.1%) no significant increase in viscosity was noticed. Formulation 010, which contains low amounts of mineral oil, exhibited a minor increase in viscosity upon the addition of 0.1% minocycline HCl (which with higher amounts of minocycline could have been more substantial). However, very surprisingly, it was observed that the addition of a very low amount of minocycline HCl greatly increases formulation viscosity, when the viscosity of the placebo formulation is lower, as in formulations 011, 012 and 013, which contain increasingly higher amounts of mineral oil.

As shown in FIG. 1, the percentage of change in viscosity by the addition of Minocycline HCl is exponentially related to the viscosity of the formulation placebo.

In one or more embodiments, there is provided an oleaginous formulation containing hydrophobic solvents and a tetracycline in synergistic combination with a fatty alcohol, wherein the viscosity of the formulation is increased by the addition of the active ingredient by more than about 50%, more than about 100%, more than about 200%, more than about 300%, more than about 500%.

In one or more embodiments, the lower the viscosity of the placebo formulation, the greater the increase in formulation viscosity after addition of the active ingredient.

Example 6—Other Oils-Based Formulations with Increased Viscosity

The influence of the addition of a tetracycline on vegetable oils-based formulations was then studied when the active ingredient is combined with a mixture of vegetable oils, fatty alcohols, fatty acids and waxes, as described in Table 6.

TABLE 6

Formulation based on vegetable oils with increased viscosity

| Ingredients | 244P % w/w | 244B % w/w | 244A % w/w |
| --- | --- | --- | --- |
| Soybean oil | 50.00 | 50.00 | 50.00 |
| Coconut oil | 23.60 | 23.60 | 23.60 |
| Light Mineral oil | 5.55 | 4.40 | 0.95 |
| Cyclomethicone | 5.00 | 5.00 | 5.00 |
| Cetostearyl alcohol | 3.50 | 3.50 | 3.50 |
| Stearic acid | 3.00 | 3.00 | 3.00 |
| Myristyl alcohol | 2.50 | 2.50 | 2.50 |
| Hydrogenated castor oil | 2.00 | 2.00 | 2.00 |
| Beeswax | 2.00 | 2.00 | 2.00 |
| Stearyl alcohol | 1.50 | 1.50 | 1.50 |
| Behenyl alcohol | 1.10 | 1.10 | 1.10 |
| Silicon dioxide | 0.25 | 0.25 | 0.25 |
| Total | 100.00 | 100.00 | 100.00 |
| Minocycline HCl | — | 1.15 | 4.60 |
| Viscosity Results at 10 rpm (cP) | 7214 | 14429 | 17084 |
| % Viscosity Change | — | +100% | +137% |

The combination of a tetracycline with a mixture of vegetable oils, fatty alcohols, fatty acids and waxes has a strong synergistic effect and increases the formulation viscosity. The viscosity of a formulation containing 1.15% minocycline HCl is about twice higher than the viscosity of the placebo formulation. Moreover, the effect on the formulation viscosity is directly related to the concentration of the tetracycline: the higher the tetracycline concentration, the higher the viscosity of the formulation. Formulation 244 is a solid gel which spreads easily upon application of shear force.

In one or more embodiments, there is provided an oleaginous formulation containing vegetable oils and a tetracycline in synergistic combination with a fatty alcohol, a fatty acid and a wax, wherein the viscosity of the formulation is increased by the addition of the active ingredient by more than about 50%, more than about 100%, more than about 200%, more than about 300%, or more than about 500%.

Example 7—Stability of a Tetracycline in Viscosity Controlled Formulations

Tetracycline antibiotics are known to be very unstable active agents that are degraded by a wide range of commonly used pharmaceutical excipients. For example, it has been found that minocycline is degraded in 1 to 2 days in the presence of various hydrophilic solvents (such as water, glycerin, sodium PCA, propylene glycol and polyethylene glycols), by water dispersed polymers (such as xanthan gum, poloxamers, carbomers, methocel, sodium carboxymethylcellulose) and by surfactants (such as polysorbates, sorbitan esters, polyoxyalkyl esters and lanolin-based surfactants). Thus, the achievement of a long term stable formulation of tetracycline antibiotics described herein, was a major challenge and required both extensive research and creativity.

The following example illustrates the chemical stability of Minocycline HCl (MCH) in an oleaginous formulation as described in Tables 7a. In an accelerated stability study, samples were stored at 40° C., and the concentration of Minocycline HCl was determined by chromatographic methods. The stability test results following, 3 weeks and 6 months of storage at 40° C. are shown in Table 7b.

TABLE 7a

Composition of formulation incubated at 40° C.

| Ingredients | Formulations 244B % w/w |
| --- | --- |
| Soybean oil | 50.00 |
| Coconut oil | 23.60 |
| Light Mineral oil | 4.40 |
| Cyclomethicone | 5.00 |
| Cetostearyl alcohol | 3.50 |
| Stearic acid | 3.00 |
| Myristyl alcohol | 2.50 |
| Hydrogenated castor oil | 2.00 |
| Beeswax | 2.00 |
| Stearyl alcohol | 1.50 |
| Behenyl alcohol | 1.10 |
| Silicon dioxide | 0.25 |
| Total | 100.00 |
| Minocycline HCl | 1.11 |

TABLE 7b

Analytical Stability results of composition 244B containing Minocycline HCl

| | T0 | after 3 weeks at 40° C. | after 6 months at 40° C. |
| --- | --- | --- | --- |
| Minocycline content (%) | 101.5% | 99.1% | 95.3% |

Very surprisingly, and despite the known instability of tetracycline antibiotics, the accelerated stability results of formulation 244B after 3 weeks and 6 months at 40° C. showed minimal degradation of the active agent in the formulations. The formulations disclosed herein thus show an extended accelerated stability for the tetracycline antibiotic active agent, an outstanding physical stability, wherein the viscosity of the formulation is substantially increased by the addition of the active ingredient.

In another experiment, a sample of formulation 244B was stored during 6 months at 40° C. and tested for active ingredient content uniformity and physical stability. It was found that minocycline HCl was homogeneously dispersed into formulation even after prolonged incubation at 40° C. Furthermore, it was found that the formulation remained as a homogeneous gel after 6 months of incubation at 40° C.

In one or more embodiments, there is provided a formulation wherein the active ingredient is homogeneously dispersed in the formulation and remains homogeneously dispersed after 6 months of incubation at 40° C.

Example 8—Formulations with Improved Viscosity and Various Active Ingredients Formulation with different active ingredients were prepared as described in Table 8a, to study the influence of the combination of various active ingredients with a fatty alcohol on formulation viscosity.

TABLE 8a

Formulations of fatty alcohol and oil with improved viscosity with various active ingredients

| | Formulations | | | | |
|---|---|---|---|---|---|
| | 029 % w/w | 030 % w/w | 031 % w/w | 032 % w/w | 033 % w/w |
| Ingredients | | | | | |
| Heavy Mineral oil | 65 | 65 | 65 | 65 | 65 |
| Light mineral oil | 25 | 25 | 25 | 25 | 25 |
| Stearyl alcohol | 10 | 10 | 10 | 10 | 10 |
| Total | 100.00 | 100.00 | 100.00 | 100.00 | 100.00 |
| Minocycline HCl micronized | 0.05 | — | — | — | — |
| Minocycline HCl non micronized | — | 0.10 | — | — | — |
| Tetracycline HCl | — | — | 0.10 | — | — |
| Cholesterol | — | — | — | 0.10 | — |
| Benzoyl peroxide | — | — | — | — | 0.10 |
| Viscosity Results at 10 rpm (cP) | | | | | |
| Placebo | 1152 | 1152 | 1152 | 1152 | 1152 |
| With Active ingredient | 2655 | 2128 | 2655 | 1888 | 2112 |
| % Viscosity Change | +130% | +85% | +130% | +64% | +83% |

It was found that the increase in viscosity observed after the addition of the active ingredient minocycline is also observed with other active ingredients. A strong increase in formulation viscosity was observed with tetracycline HCl which is another compound of the tetracycline class. To a lesser extent, an increase in formulation viscosity was observed with Cholesterol which is also a 4-ring compound and with benzoyl peroxide. It can be note that the strongest effect was observed with tetracycline compounds, such as Minocycline HCl and Tetracycline HCl. It can be further noted that even at concentrations as low as 0.05%, the addition of Minocycline HCl to the formulations more than doubled the viscosity. It is further noted that micronized preparations appear to have a more pronounced effect. Without being bound by any theory a possible explanation might be that the rheology change is improved when smaller particles are used providing a higher surface area exposure of the active therapeutic, which facilitates more interactions within the composition.

Formulation with different active ingredients were prepared as described in Table 8b and Table 8c, to study the influence of the combination of various active ingredients with a wax on formulation viscosity.

TABLE 8b

Formulations of wax and oil with improved viscosity with various active ingredients
(continued)

| | Formulations | | | | | | | |
|---|---|---|---|---|---|---|---|---|
| | 042 % w/w | 043 % w/w | 044 % w/w | 045 % w/w | 046 % w/w | 047 % w/w | 048 % w/w | 049 % w/w |
| Ingredients | | | | | | | | |
| Heavy Mineral oil | 65 | 65 | 65 | 65 | 65 | 65 | 65 | 65 |
| Light mineral oil | 30 | 30 | 30 | 30 | 30 | 30 | 30 | 30 |
| Hydrogenated Castor oil | 5 | 5 | 5 | 5 | 5 | 5 | 5 | 5 |
| Total | 100.00 | 100.00 | 100.00 | 100.00 | 100.00 | 100.00 | 100.00 | 100.00 |
| Minocycline HCl micronized | 0.10 | — | — | — | — | — | — | — |
| Minocycline HCl non micronized | — | 0.10 | — | — | — | — | — | — |
| Tetracycline HCl | — | — | 0.10 | — | — | — | — | — |
| Cholesterol | — | — | — | 0.10 | — | — | — | — |
| Benzoyl peroxide | — | — | — | — | 0.10 | — | — | — |
| Mometasone Furoate | — | — | — | — | — | 0.10 | — | — |
| Doxycycline Hyclate | — | — | — | — | — | — | 0.10 | — |
| Salicylic acid | — | — | — | — | — | — | — | 0.10 |
| Viscosity Results at 10 rpm (cP) | | | | | | | | |
| Placebo | 816 | 816 | 816 | 816 | 816 | 816 | 816 | 816 |
| With Active ingredient | 3343 | 13357 | 8126 | 2415 | 7039 | 10606 | 7566 | 8974 |
| % Viscosity Change | +310% | +1537% | +896% | +196% | +763% | +1200% | +827% | +1000% |

TABLE 8c

Formulations of wax and oil with improved viscosity with various active ingredients
(further continued)

| | Formulations | | | | | | |
|---|---|---|---|---|---|---|---|
| | 050 % w/w | 051 % w/w | 052 % w/w | 053 % w/w | 054 % w/w | 055 % w/w | 056 % w/w |
| Ingredients | | | | | | | |
| Heavy Mineral oil | 65 | 65 | 65 | 65 | 65 | 65 | 65 |
| Light mineral oil | 30 | 30 | 30 | 30 | 30 | 30 | 30 |
| Hydrogenated Castor oil | 5 | 5 | 5 | 5 | 5 | 5 | 5 |
| Total | 100.00 | 100.00 | 100.00 | 100.00 | 100.00 | 100.00 | 100.00 |
| Vitamin E | 0.10 | — | — | — | — | — | — |
| Diclofenac | — | 0.10 | — | — | — | — | — |
| Urea | — | — | 0.10 | — | — | — | — |
| Terbinafine | — | — | — | 0.10 | — | — | — |
| Permethrin | — | — | — | — | 0.10 | — | — |
| Metronidazole | — | — | — | — | — | 0.10 | — |
| Pimecrolimus | — | — | — | — | — | — | 0.10 |
| Viscosity Results at 10 rpm (cP) | | | | | | | |
| Placebo | 816 | 816 | 816 | 816 | 816 | 816 | 816 |
| With Active ingredient | 7310 | 5663 | 5551 | 12733 | 6623 | 11246 | 12909 |
| % Viscosity Change | +796% | +594% | +580% | +1461% | +712% | +1278% | +1482% |

It was noted that after various active ingredient were added separately to an oil and wax oleaginous formulation a viscosity increase is observed over a wide range of active ingredients.

Example 9—Formulation with Beeswax Alone in Mineral Oil

The influence of a low concentration of tetracycline with beeswax on formulation viscosity was compared in Table 9.

TABLE 9

| Oleaginous preparations | |
|---|---|
| | Formulations 005 % w/w |
| Ingredients | |
| Heavy mineral oil | 65 |
| Light mineral oil | 25 |
| Beeswax | 10 |
| Total | 100.00 |
| Viscosity Results at 10 rpm (cP) | |
| Without Minocycline HCl | 942 |
| With 0.1% Minocycline HCl | 1695 |
| % Viscosity Change | +80% |

Example 10—Compatibility Study

Procedure: Minocycline hydrochloride ("MCH") was incubated as a suspension with various excipients at 25° C. and 40° C. for maximum of sixty days or to the point where degradation was suspected. The ratio between MCH and the tested excipient is detailed below. Visual inspection was the major criterion for indication of compatibility. The color of intact MCH suspension is pale yellow; and any change of color (e.g., to dark orange, red, green, brown and black) indicates oxidation or degradation.

Hydrophilic solvents were tested for compatibility with MCH at a ratio of MCH: excipient of 1:250. Dimethyl Isosorbide, Glycerin, Ethanol, Propylene glycol, Butylene Glycol, PEG 200, Hexylene Glycol, PEG 400, Dimethyl Sulfoxide and Diethylene glycol monoethyl ether were found to be incompatible with MCH.

Oily emollients and waxes were tested for compatibility with MCH at a ratio of MCH: excipient of 1:250 for Oily emollients and 1:50 for waxes. Hydrogenated castor oil, Castor oil, Cocoglycerides, Disopropyl adipate, Mineral oil light, Coconut oil, Beeswax, MCT oil, Cyclomethicone, Isododecane, Cetearyl octanoate, Gelled mineral oil, Isopropyl myristate, PPG 15 stearyl ether, Mineral oil heavy, Octyl dodecanol, White Petrolatum, Petrolatum (Sofmetic), Paraffin 42-44, Paraffin 51-53, Paraffin 56-62, Calendula oil, Shea butter, Grape seed oil, Almond oil, Jojoba oil, Avocado oil, Peanut oil, Wheat germ oil and Hard Fat were found to be compatible with MCH. Pomegranate seed oil was found to be incompatible with MCH.

The compatibility of MCH with hydrophobic surfactant was tested following solubilization of the surfactant in mineral oil (mineral oil was previously shown to be compatible with MCH). Surfactants were tested for compatibility with MCH at a ratio of MCH: excipient of 1:50. PEG 150 distearate, Laureth 4, PEG 40 hydrogenated castor oil, PEG 75 lanolin, Glucam P20 distearate, PEG 100 stearate, Glyceryl monostearate, PEG 40 stearate, Montanov S (Cocoyl Alcohol (and) C12-20 Alkyl Glucoside)), Alkyl lactate, Benton gel, SPAN 60, Sorbitan sesquistearate, SPAN 40, Tween 20, Ceteth 2, Sucrose stearic acid esters D1813, Ceteareth 20, Steareth 2/Steareth 21, Methyl glucose sesquistearate, Oleth 20, PPG 20 methyl glucose ether, Tween 60 were found to be incompatible with MCH. Sucrose stearic acid esters D1803, Sucrose stearic acid esters D1807 and Sucrose stearic acid esters D1811 were found to be compatible with MCH; however, not all of them dissolved in oil (e.g. 1811, 1813).

Foam adjuvants were tested for compatibility with MCH at a ratio of MCH: excipient of 1:50. Isostearyl alcohol, Behenyl alcohol, Stearyl alcohol, Cetyl alcohol, Oleyl alcohol, Myristyl alcohol, Cetostearyl alcohol, Palmitic acid, Stearic acid and Oleic acid were found to be compatible with MCH. Isostearic acid was not compatible with MCH.

Additives were tested for compatibility with MCH at a ratio of MCH: excipient of 1:50. Aerosil and Menthol were found to be compatible with MCH. Titanium dioxide and Ethocel were not compatible with MCH.

Additives were tested for compatibility with MCH. Minimal quantities of water (100 µL) were added to MCH, suspended in excipients that had demonstrated compatibility to examine whether water can enhance oxidation/degradation in the absence or presence of antioxidant. In parallel, antioxidants were added to the MCH suspensions comprising water. Antioxidants were also added to excipients which were found to be non compatible with MCH. Addition of water caused prompt degradation of MCH. Addition of the antioxidants alpha-tocopherol, BHA/BHT and propyl gallate did not prevent MCH degradation. Compatible excipients became incompatible in the presence of water. Addition of antioxidants did not alter this result.

What is claimed is:

1. An oleaginous foam composition comprising:
   a) a combination of at least one fatty alcohol and at least one wax; or a combination of at least one fatty alcohol, at least one fatty acid, and at least one wax;
   b) at least one hydrophobic solvent; and
   c) a minocycline at a concentration between about 1% and about 4% by weight of the composition;
   wherein the composition is free of surfactant;
   wherein the composition is essentially waterless;
   wherein the ratio of (1) fatty alcohol to wax or (2) fatty alcohol and fatty acid to wax is between about 1:3 and about 3:1; and
   wherein the wax comprises a mixture of beeswax and hydrogenated castor oil.

2. The composition of claim 1, wherein the minocycline is present in a free base form, a hydrate form, a salt form, or a complex form.

3. The composition of claim 1, further comprising a tetracycline, an oxytetracycline, a demeclocycline, a doxycycline, a lymecycline, a meclocycline, a methacycline, a rolitetracycline, a chlorotetracycline, a tigecycline, or a mixture of two or more thereof.

4. The composition of claim 1, further comprising a doxycycline.

5. The composition of claim 1, wherein the concentration of the minocycline is about 4% by weight of the composition.

6. The composition of claim 1, wherein the concentration of the minocycline is about 1% by weight of the composition.

7. The composition of claim 1, wherein the at least one fatty alcohol comprises 14 carbon atoms in its backbone.

8. The composition of claim 1, wherein the fatty alcohol comprises stearyl alcohol, cetostearyl alcohol, behenyl alcohol, and/or myristyl alcohol.

9. The composition of claim 1, wherein the at least one fatty alcohol is present at a concentration from about 0.1% to about 20% by weight of the composition.

10. The composition of claim 1, wherein the at least one wax and/or the at least one fatty acid is present at a concentration from about 0.1% to about 20% by weight of the composition.

11. The composition of claim 1, wherein the hydrophobic solvent comprises soybean oil, coconut oil, cyclomethicone, and/or mineral oil.

12. The composition of claim 1, wherein the hydrophobic solvent is present at a concentration from about 60% to about 95% by weight of the composition.

13. The composition of claim 1, further comprising a retinoid.

14. The composition of claim 13, wherein the retinoid comprises tazarotene, adapalene, and/or isotretinoin.

15. The composition of claim 1, further comprising a silicon dioxide.

16. The composition of claim 1, further comprising a benzoyl peroxide.

17. The composition of claim 1, wherein the wax comprises a mixture of beeswax and hydrogenated castor oil at a ratio of about 1:1.

18. The composition of claim 1, wherein the concentration of the minocycline is about 3% by weight of the composition.

* * * * *